(12) United States Patent
Wu et al.

(10) Patent No.: US 8,987,474 B2
(45) Date of Patent: *Mar. 24, 2015

(54) INHIBITION OF SHP2/PTPN11 PROTEIN TYROSINE PHOSPHATASE BY NSC-87877, NSC-117199 AND THEIR ANALOGS

(75) Inventors: Jie Wu, Tampa, FL (US); Nicholas J. Lawrence, Tampa, FL (US); Said M. Sebti, Tampa, FL (US); Harshani R. Lawrence, Tampa, FL (US)

(73) Assignees: University of South Florida, Tampa, FL (US); H. Lee Moffitt Cancer Center and Research Institute, Inc., Tampa, FL (US)

( * ) Notice: Subject to any disclaimer, the term of this patent is extended or adjusted under 35 U.S.C. 154(b) by 427 days.

This patent is subject to a terminal disclaimer.

(21) Appl. No.: 11/733,023

(22) Filed: Apr. 9, 2007

(65) Prior Publication Data
US 2008/0176309 A1 Jul. 24, 2008

Related U.S. Application Data

(60) Provisional application No. 60/744,431, filed on Apr. 7, 2006.

(51) Int. Cl.
*A61K 31/404* (2006.01)
*A61K 31/405* (2006.01)
*C07D 209/40* (2006.01)

(52) U.S. Cl.
CPC ............ *A61K 31/405* (2013.01); *C07D 209/40* (2013.01)
USPC .......................................... 548/492; 514/419

(58) Field of Classification Search
CPC ...................................................... C07D 209/40
USPC .................................. 514/183, 419; 548/492
See application file for complete search history.

(56) References Cited

U.S. PATENT DOCUMENTS

2003/0004351 A1* 1/2003 Davis et al. ................... 546/200

FOREIGN PATENT DOCUMENTS

WO 2007117699 A2 10/2007

OTHER PUBLICATIONS

Frank D. Popp, Synthesis of potential antineoplastic agents. XX. Compounds related to the 3-o-Nitrophenylhydrazone of Isatin. 1969, Journal of Medicinal Chemistry, vol. 12, No. 1, pp. 182-184.*
Alonso A, et al (2004) Protein tyrosine phosphatases in the human genome. *Cell* 117(6):699-711.
Andersen JN, et al. (2001) Structural and evolutionary relationships among protein tyrosine phosphatase domains. *Mol Cell Biol* 21(21):7117-7136.
Bennett AM, (1996) Multiple requirements for SHPTP2 in epidermal growth factor-mediated cell cycle progression. *Mol Cell Biol* 16(3):1189-1202.
Bentires-ALJ M, et al. (2004) Activating mutations of the noonan syndrome-associated SHP2/PTPN11 gene in human solid tumors and adult acute myelogenous leukemia. *Cancer Res* 64(24):8816-8820.
Bialy L and Waldmann H (2005) Inhibitors of protein tyrosine phosphatases: next-generation drugs? *Angew Chem Int Ed Engl* 44(25):3814-3839.
Carroll MP and May WS (1994) Protein kinase C-mediated serine phosphorylation directly activates Raf-1 in murine hematopoietic cells. *J Biol Chem* 269(2):1249-1256.
Chan RJ, et al. (2005) Human somatic PTPN11 mutations induce hematopoietic-cell hypersensitivity to granulocyte-macrophage colony-stimulating factor. *Blood* 105(9):3737-3742.
Cunnick JM, et al. (1998) Reversible regulation of SHP-1 tyrosine phosphatase activity by oxidation. *Biochem Mol Biol Int* 45(5):887-894.
Cunnick JM, et al (2001) Phosphotyrosines 627 and 659 of Gab1 constitute a bisphosphoryl tyrosine-based activation motif (BTAM) conferring binding and activation of SHP2. *J Biol Chem* 276(26):24380-24387.
Cunnick JM, et al (2002) Regulation of the mitogen-activated protein kinase signaling pathway by SHP2. *J Biol Chem* 277(11):9498-9504.
Deb TB, et al. (1998) A common requirement for the catalytic activity and both SH2 domains of SHP-2 in mitogen-activated protein (MAP) kinase activation by the ErbB family of receptors. A specific role for SHP-2 in map, but not c-Jun amino-terminal kinase activation. *J Biol Chem* 273(27):16643-16646.
Fragale A, et al. (2004) Noonan syndrome-associated SHP2/PTPN11 mutants cause EGF-dependent prolonged GAB1 binding and sustained ERK2/MAPK1 activation. *Hum Mutat* 23(3):267-277.
Friesner RA, et al. (2004) Glide: a new approach for rapid, accurate docking and scoring. 1. Method and assessment of docking accuracy. *J Med Chem* 47(7):1739-1749.
Gu H and Neel BG (2003) The "Gab" in signal transduction. *Trends Cell Biol* 13(3):122-130.
Halgren TA, (2004) Glide: a new approach for rapid, accurate docking and scoring. 2. Enrichment factors in database screening. *J Med Chem* 47(7):1750-1759.

(Continued)

*Primary Examiner* — James D Anderson
*Assistant Examiner* — Meghan Finn
(74) *Attorney, Agent, or Firm* — Robert J. Varkonyi; Smith & Hopen, P.A.

(57) ABSTRACT

Compounds and associated methods for inhibiting a protein tyrosine phosphatase. By a combination of experimental and virtual screenings of the NCI Diversity Set chemical library, NSC-87877 and NSC-117199 have been identified as Shp2 PTP inhibitors. Significantly, NSC-87877 is active in cell-based assays and has no detectable off-target effects in the EGF-stimulated Erk 1/2 activation pathway. Additionally, a number of analogs of NSC-117199 have been produced. These analogs exhibit enhanced protein tyrosine phosphatase inhibition and are found to be potent and/or selective inhibitors of Shp1 and/or Shp2 protein tyrosine phosphatases.

11 Claims, 8 Drawing Sheets

(56) References Cited

OTHER PUBLICATIONS

Hatakeyama M (2004) Oncogenic mechanisms of the Helicobacter pylori CagA protein. *Nat Rev Cancer* 4(9):688-694.
Hof P, et al. (1998) Crystal structure of the tyrosine phosphatase SHP-2. *Cell* 92(4):441-450.
Huang P, et al. (2003) Structure-based design and discovery of novel inhibitors of protein tyrosine phosphatases. *Bioorg Med Chem* 11(8):1835-1849.
Keilhack H, et al. (2005) Diverse biochemical properties of SHP2 mutants. Implications for disease phenotypes. *J Biol Chem* 280(35):30984-30993.
Kolch W, et al. (1993) Protein kinase C alpha activates RAF-1 by direct phosphorylation. *Nature* 364(6434):249-252.
Kratz CP, et al. (2005) The mutational spectrum of PTPN11 in juvenile myelomonocytic leukemia and Noonan syndrome/myeloproliferative disease. *Blood* 106(6):2183-2185.
Lazo JS, et al. (2002) Identification of a potent and selective pharmacophore for Cdc25 dual specificity phosphatase inhibitors. *Mol Pharmacol* 61(4):720-728.
Maroun CR, et al. (2000) The tyrosine phosphatase SHP-2 is required for sustained activation of extracellular signal-regulated kinase and epithelial morphogenesis downstream from the met receptor tyrosine kinase. *Mol Cell Biol* 20(22):8513-8525.
McCain DF, et al. (2004) Suramin derivatives as inhibitors and activators of protein-tyrosine phosphatases. *J Biol Chem* 279(15):14713-14725.
Mohl MG, et al. (2005) Prognostic, therapeutic, and mechanistic implications of a model of leukemia evoked by Shp2 (PTPN11) mutations. *Cancer Cell* 7(2):179-191.
Neel BG, Gu H and Pao L (2003) The 'Shp'ing news: SH2 domain-containing tyrosine phosphatases in cell signaling. *Trends Biochem Sci* 28(6):284-293.
Nishida K and Hirano T (2003) The role of Gab family scaffolding adapter proteins in the signal transduction of cytokine and growth factor receptors. *Cancer Sci* 94(12):1029-1033.
O'Reilly AM and Neel BG (1998) Structural determinants of SHP-2 function and specificity in Xenopus mesoderm induction. *Mol Cell Biol* 18(1):161-177.
Oka T, et al. (2002) Gene silencing of the tyrosine phosphatase SHP1 gene by aberrant methylation in leukemias/lymphomas. *Cancer Res* 62(22):6390-6394.
Ren Y, et al. (2004) Roles of Gab1 and SHP2 in paxillin tyrosine dephosphorylation and Src activation in response to epidermal growth factor. *J Biol Chem* 279(9):8497-8505.
Schubbert S, et al. (2005) Functional analysis of leukemia-associated PTPN11 mutations in primary hematopoietic cells. *Blood* 106(1):311-317.
Shen K, et al. (2001) Acquisition of a specific and potent PTP1B inhibitor from a novel combinatorial library and screening procedure. *J Biol Chem* 276(50):47311-47319.
Stein CA (1993) Suramin: a novel antineoplastic agent with multiple potential mechanisms of action. *Cancer Res* 53(10 Suppl):2239-2248.
Tartaglia M and Gelb BD (2005) Germ-line and somatic PTPN11 mutations in human disease. *Eur J Med Genet* 48(2):81-96.
Tartaglia M, et al. (2003) Somatic mutations in PTPN11 in juvenile myelomonocytic leukemia, myelodysplastic syndromes and acute myeloid leukemia. *Nat Genet* 34(2):148-150.
Yamauchi K, et al. (1995) Protein-tyrosine-phosphatase SHPTP2 is a required positive effector for insulin downstream signaling. *Proc Natl Acad Sci U S A* 92(3):664-668.
Yang J, et al. (1998) Crystal structure of the catalytic domain of protein-tyrosine phosphatase SHP-1. *J Biol Chem* 273(43):28199-28207.
Yang J, et al. (2003) Crystal structure of human protein-tyrosine phosphatase SHP-1. *J Biol Chem* 278(8):6516-6520.
Zhang ZY (2002) Protein tyrosine phosphatases: structure and function, substrate specificity, and inhibitor development. *Annu Rev Pharmacol Toxicol* 42:209-234.
International Search Report for PCT/US2009/042305 dated Nov. 11, 2010.
Robinett et al. The Discovery of Substituted 4-(3-hydroxyanilino)-quinolines as Potent RET Kinase Inhibitors, Bioorganic & Medicinal Chemistry Letters, 2007, vol. 17, No. 21, pp. 5886-5893.
Dubois et al. 2006. "The SHP-1 Protein Tyrosine Phosphatase Negatively Modulates Glucose Homeostasis." Nat. Med. vol. 12. No. 5. pp. 549-556.
Zhang et al. 2009. "Targeting Cancer with Small Molecule Kinase Inhibitors." Nature. vol. 9. pp. 28-39.

\* cited by examiner

NSC 87877

NSC 117199

INHIBITION OF SHP2/PTPN11 PROTEIN TYROSINE PHOSPHATASE BY NSC-87877, NSC-117199 AND THEIR ANALOGS

CROSS REFERENCE TO RELATED APPLICATIONS

This application claims priority to currently pending U.S. Provisional Patent Application 60/744,431, entitled, "Shp2 Protein Tyrosine Phosphatase Inhibitor", filed Apr. 7, 2006, the contents of which are herein incorporated by reference.

STATEMENT OF GOVERNMENT INTEREST

This invention was made with Government support under Grant No. CA077467 awarded by the National Cancer Institute. The Government has certain rights in the invention.

FIELD OF INVENTION

This invention relates to cancer therapy. More specifically, this invention relates to compounds useful in inhibiting Shp2/PTPN11 protein tyrosine phosphatase activity.

BACKGROUND OF THE INVENTION

Shp2, encoded by the PTPN11 gene, is a non-receptor PTP with two Src homology-2 (SH2) domains (N-SH2, C-SH2) (Alonso et al., 2004; Neel et al., 2003). Molecular biology and genetic studies has shown that Shp2 mediates cell signaling by growth factors and cytokines, such as epidermal growth factor (EGF), hepatocyte growth factor, and interleukin-6. In particular, Shp2 is involved in activation of Erk1/2 MAP kinase by EGF (Deb et al., 1998).

Shp2 is basally inactive due to auto-inhibition by its N-SH2 domain (Hof et al., 1998). In growth factor- and cytokine-stimulated cells, Shp2 binds to tyrosine-phosphorylated docking proteins through its SH2 domains, resulting in its activation (Cunnick et al., 2001). It has been shown that Shp2 binds to Gab1 (or Gab2) in cells stimulated with EGF, HGF, or interleukin-6 (Cunnick et al., 2001; Gu and Neel, 2003; Maroun et al., 2000; Nishida and Hirano, 2003). Gab1-Shp2 interaction as well as Shp2 PTP activity are necessary for Erk1/2 activation by these growth factors (Cunnick et al., 2002; Neel et al., 2003). While the mechanism by which growth factors activate Shp2 has been elucidated, those by which Shp2 produces downstream signals to activate Ras-Erk1/2 MAP kinase pathway and possibly other pathways are less clear and may be growth factor- and cell context-dependent (Mohi et al., 2005).

Besides its role in growth factor and cytokine signaling, Shp2 has been implicated in pathogenicity of *H. pylori*. Cytotoxin-associated antigen A (CagA)-positive strains of *H. pylori* are strongly associated with gastritis and gastric cancer. After injected into host cells, CagA is retained on the plasma membrane and recruits Shp2 to induce transformation of gastric epithelial cells (Hatakeyama, 2004).

Remarkably, PTPN11 mutations have been found in Noonan syndrome, juvenile myelomonocytic leukemia (JMML), and several types of human malignancies (Bentires-Alj et al., 2004; Tartaglia and Gelb, 2005). Noonan syndrome is a developmental disorder characterized by facial anomalies, short stature, heart disease, skeletal defects, and hematological disorders (Tartaglia and Gelb, 2005). Germline PTPN11 mutations are responsible for causing 50% of cases of Noonan syndrome. Some children with Noonan syndrome also develop JMML (Tartaglia et al., 2003). JMML is a progressive myelodysplastic/myeloproliferative disorder characterized by overproduction of tissue-infiltrating myeloid cells. Approximately 50% of cases of JMML have activating Ras mutations or homozygotic inactivation of the NF1 gene that encodes a Ras-GTPase activating protein, neurofibromin. Somatic mutations in PTPN11 account for about 35% of JMML patients who do not have Ras or neurofibromin mutations (Kratz et al., 2005). It was reported recently that JMML-associated Shp2 mutants could transform murine bone marrow and fetal liver cells (Chan et al., 2005; Mohi et al., 2005; Schubbert et al., 2005) and caused fatal JMML-like disorder in Balb/c mice (Mohi et al., 2005). While molecular etiologies of Noonan syndrome and JMML are becoming clear, several mechanistic issues regarding how Shp2 mutants cause Noonan syndrome and JMML remain unanswered. Importantly, all Shp2 mutants found in Noonan syndrome and JMML are gain-of-function mutations, mostly resulting from weaker autoinhibition of the N-SH2 domain (Fragale et al., 2004; Keilhack et al., 2005).

In short, accumulated molecular biology and genetic evidence has suggested that Shp2 is an important signaling component of growth factors, cytokines, and oncogenic bacteria. Gain-of-function Shp2 mutations are linked to childhood developmental disorder and juvenile leukemias. Therefore, Shp2 PTP is an important target for controlling growth factor receptor signaling and a potential target for development of novel therapies for Noonan syndrome, JMML, and possibly other Shp2-associated cancers.

PTP inhibitor development is an emerging area in the field of drug development (Bialy and Waldmann, 2005). Most efforts of PTP inhibitor discovery and design have so far been focused on PTP1B and Cdc25 inhibitors (Lazo et al., 2002; Zhang, 2002). No systematic effort to identify Shp2-selective PTP inhibitors has been reported. While PTP1B inhibitors that cross-inhibit Shp2 have been found (Huang et al., 2003; Shen et al., 2001), none of them has demonstrated in vivo activity in cell cultures.

SUMMARY OF INVENTION

The present invention provides compounds and associated methods for inhibiting a protein tyrosine phosphatase. By a combination of experimental and virtual screenings of the NCI Diversity Set chemical library, NSC-87877 and NSC-117199 have been identified as Shp2 PTP inhibitors. Significantly, NSC-87877 is active in cell-based assays and has no detectable off-target effects in the EGF-stimulated Erk1/2 activation pathway. Additionally, a number of analogs of NSC-117199 have been produced. These analogs exhibit enhanced protein tyrosine phosphatase inhibition and are found to be potent inhibitors of Shp1 and Shp2.

In a first aspect the present invention provides a method of inhibiting a protein tyrosine phosphatase in a cell comprising the step of contacting the cell with an effective amount of a compound having the formula (I):

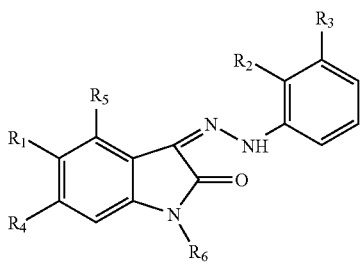

(I)

wherein each $R_1$ through $R_5$ are independently hydrogen, halogen, phenyl, nitro, sulfo, carboalkoxy, carboxyamide, benzylcarboxamide, straight chained, branched or cyclic alkyl, $CO_2H$, $SO_3H$, $CO_2NH_2$, $SO_2NH_2$, $PO_3H$, $CF_2PO_3H$, $(CH_2)_nCO_2H$, $(CH_2)_nCO_2H$, $(CH_2)_nSO_3H$, $(CH_2)_nCO_2NH_2$, $(CH_2)_nSO_2NH_2$, $(CH_2)_nPO_3H$, $O(CH_2)_nCO_2H$, $O(CH_2)_nSO_3H$, $O(CH_2)_nCO_2NH_2$, $O(CH_2)_nSO_2NH_2$, $O(CH_2)_nPO_3H$, $NH(CH_2)_nCO_2H$, $NH(CH_2)_nSO_3H$, $NH(CH_2)_nCO_2NH_2$, $NH(CH_2)_nSO_2NH_2$, $NH(CH_2)_nPO_3H$,

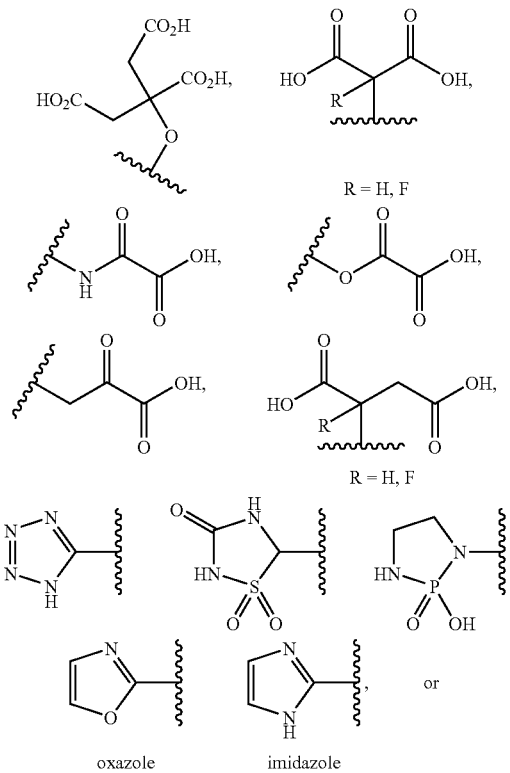

hydrogen, wherein n=1 to 5; and $R_6$ is hydrogen, halogen, phenyl, benzyl, nitro, sulfo, carboalkoxy, carboxyamide, straight chained, branched or cyclic alkyl.

In certain embodiments at least two of $R_1$, $R_4$ and $R_5$ are hydrogen. In further embodiments the protein tyrosine phosphatase is a Shp protein tyrosine phosphatase selected from the group consisting of Shp1 protein tyrosine phosphatase and Shp2 protein tyrosine phosphatase. In still further embodiments Shp protein tyrosine phosphatase can be selective inhibitor of the Shp protein tyrosine phosphatase. The present invention further provides compounds of formula (I).

In a second aspect the present invention provides a method of inhibiting a protein tyrosine phosphatase in a cell comprising the step of contacting the cell with an effective amount of a compound having the formula (II):

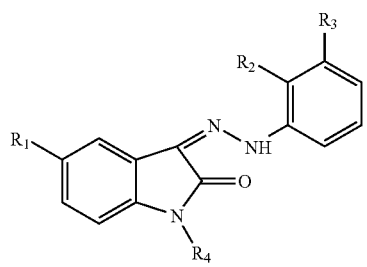

(II)

wherein $R_1$ is $SO_3H$, $CO_2H$, $SO_2NH^iPR$, $SO_2NHCH_2C_6H_5Cl$ or $SO_2NHCH_2C_6H_5Cl$;

each of $R_2$ and $R_3$ are independently hydrogen, nitro, carboxy; and $R_4$ is hydrogen.

In some embodiments the protein tyrosine phosphatase is a Shp protein tyrosine phosphatase selected from the group consisting of Shp1 protein tyrosine phosphatase and Shp2 protein tyrosine phosphatase. In further embodiments Shp protein tyrosine phosphatase can be selective inhibitor of the Shp protein tyrosine phosphatase. The present invention further provides compounds of formula (II).

In a third aspect the present invention provides a method of inhibiting a protein tyrosine phosphatase comprising the step of contacting the cell with an effective amount of a compound having the formula (III):

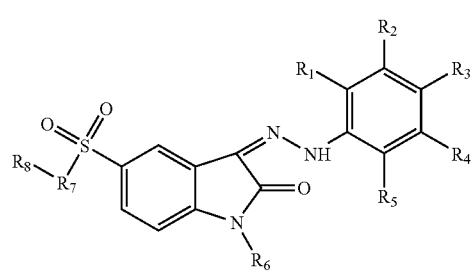

(III)

wherein each $R_1$ through $R_5$ are independently hydrogen, halogen, phenyl, nitro, sulfo, carboalkoxy, carboxyamide, benzylcarboxamide, straight chained, branched or cyclic alkyl;

$R_6$ is hydrogen, halogen, phenyl, benzyl, nitro, sulfo, carboalkoxy, carboxyamide, straight chained, branched or cyclic alkyl;

$R_7$ is oxygen or nitrogen; and $R_8$ is hydrogen, halogen, phenyl, nitro, sulfo, carboalkoxy, carboxyamide, benzylcarboxamide, straight chained, branched or cyclic alkyl, $So_2NH^iPR$, $SO_2NHCH_2C_6H_5Cl$ or $SO_2NHCH_2C_6H_5Cl$.

In some embodiments the protein tyrosine phosphatase is a Shp protein tyrosine phosphatase selected from the group consisting of Shp1 protein tyrosine phosphatase and Shp2 protein tyrosine phosphatase. In further embodiments Shp protein tyrosine phosphatase can be selective inhibitor of the Shp protein tyrosine phosphatase. The present invention further provides compounds of formula (III).

In a fourth aspect the present invention provides a method of treating a disease in a subject characterized by elevated protein tyrosine phosphatase activity comprising the step of administering to the subject in need thereof an effective amount of a compound having the formula (IV):

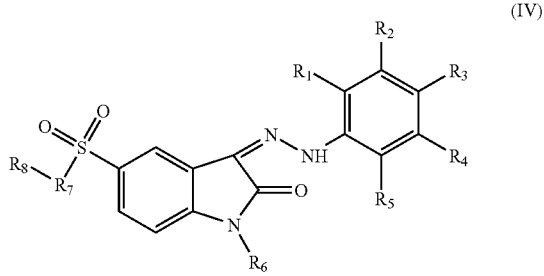

(IV)

wherein each $R_1$ through $R_5$ are independently hydrogen, halogen, phenyl, nitro, sulfo, carboalkoxy, carboxyamide, benzylcarboxamide, straight chained, branched or cyclic alkyl;
  $R_6$ is hydrogen, halogen, phenyl, benzyl, nitro, sulfo, carboalkoxy, carboxyamide, straight chained, branched or cyclic alkyl;
  $R_7$ is oxygen or nitrogen; and
  $R_8$ is hydrogen, halogen, phenyl, nitro, sulfo, carboalkoxy, carboxyamide, benzylcarboxamide, straight chained, branched or cyclic alkyl, $SO_2NH^iPR$, $SO_2NHCH_2C_6H_5Cl$ or $SO_2NHCH_2C_6H_5Cl$.

In certain embodiments the elevated protein tyrosine phosphatase activity is associated with a disease selected from the group consisting of Noonan syndrome, juvenile myelomonocytic leukemia, Noonan-like disorder with multiple giant cell lesion syndrome, LEOPARD syndrome, acute lymphoblastic leukemia, and acute myelogenous leukemia.

In a fifth aspect the present invention provides a method of inhibiting a protein tyrosine phosphatase comprising the step of contacting the cell with an effective amount of a compound having the formula (V):

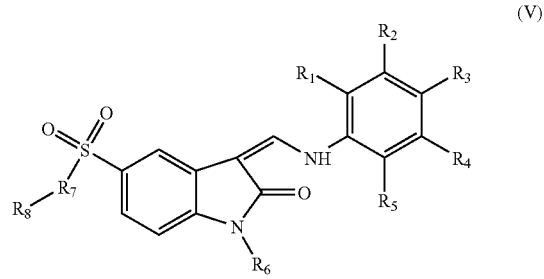

(V)

wherein each $R_1$ through $R_5$ are independently hydrogen, halogen, phenyl, nitro, sulfo, carboalkoxy, carboxyamide, benzylcarboxamide, straight chained, branched or cyclic alkyl;
  $R_6$ is hydrogen, halogen, phenyl, benzyl, nitro, sulfo, carboalkoxy, carboxyamide, straight chained, branched or cyclic alkyl;
  $R_7$ is oxygen or nitrogen; and
  $R_8$ is hydrogen, halogen, phenyl, nitro, sulfo, carboalkoxy, carboxyamide, benzylcarboxamide, straight chained, branched or cyclic alkyl, $SO_2NH^iPR$, $SO_2NHCH_2C_6H_5Cl$ or $SO_2NHCH_2C_6H_5Cl$.

In some embodiments the protein tyrosine phosphatase is a Shp protein tyrosine phosphatase selected from the group consisting of Shp1 protein tyrosine phosphatase and Shp2 protein tyrosine phosphatase. In further embodiments Shp protein tyrosine phosphatase can be selective inhibitor of the Shp protein tyrosine phosphatase. The present invention further provides compounds of formula (V).

In a sixth aspect the present invention provides a method of treating a disease in a subject characterized by elevated Shp2 protein tyrosine phosphatase comprising the step of administering to the patient an NSC-87877 (8-hydroxy-7-(6-sulfonaphthalen-2-yl)diazenyl-quinoline-5-sulfonic acid).

In certain embodiments the elevated protein tyrosine phosphatase activity is associated with a disease selected from the group consisting of Noonan syndrome, juvenile myelomonocytic leukemia, Noonan-like disorder with multiple giant cell lesion syndrome, LEOPARD syndrome, acute lymphoblastic leukemia, and acute myelogenous leukemia.

In a seventh aspect the present invention provides a method of selectively inhibiting Shp2 protein tyrosine phosphatase inhibitor in a subject comprising the steps of administering to a subject in need of such treatment NSC-87877 (8-hydroxy-7-(6-sulfonaphthalen-2-yl)diazenyl-quinoline-5-sulfonic acid).

In a eigth aspect the present invention provides a method of inhibiting a protein tyrosine phosphatase comprising the step of contacting the cell with an effective amount of a compound having the formula (VI):

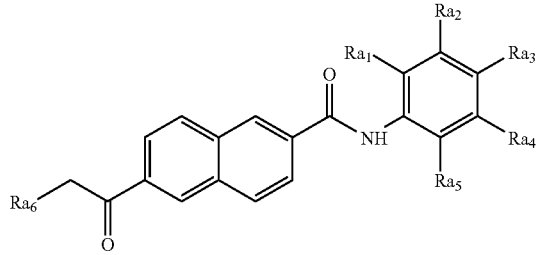

wherein each $Ra_1$ through $Ra_6$ are independently hydrogen, halogen, phenyl, nitro, sulfo, carboalkoxy, carboxyamide, benzylcarboxamide, straight chained, branched or cyclic alkyl, $CO_2H$, $SO_3H$, $CO_2NH_2$, $SO_2NH_2$, $PO_3H$, $CF_2PO_3H$, $(CH_2)_nCO_2H$, $(CH_2)_nCO_2H$, $(CH_2)_nSO_3H$, $(CH_2)_nCO_2NH_2$, $(CH_2)_nSO_2NH_2$, $(CH_2)_nPO_3H$, $O(CH_2)_nCO_2H$, $O(CH_2)_nSO_3H$, $O(CH_2)_nCO_2NH_2$, $O(CH_2)_nSO_2NH_2$, $O(CH_2)_nPO_3H$, $NH(CH_2)_nCO_2H$, $NH(CH_2)_nSO_3H$, $NH(CH_2)_nCO_2NH_2$, $NH(CH_2)_nSO_2NH_2$, $NH(CH_2)_nPO_3H$,

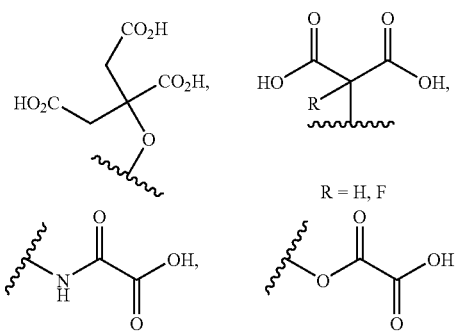

R = H, F

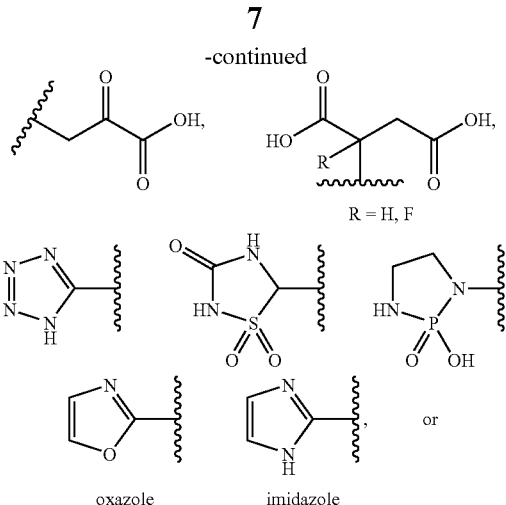

hydrogen, wherein n=1 to 5.

The present invention further provides methods of treating a disease in a subject characterized by elevated protein tyrosine phosphatase activity comprising the step of administering to the subject in need thereof an effective amount of any one of compounds (I) thorough (VI) or a combination thereof. In certain embodiments the elevated protein tyrosine phosphatase activity is associated with a disease selected from the group consisting of Noonan syndrome, juvenile myelomonocytic leukemia, Noonan-like disorder with multiple giant cell lesion syndrome, LEOPARD syndrome, acute lymphoblastic leukemia, acute myelogenous leukemia, *H. pylori*-associated gastritis and gastric cancer.

The present invention further provides methods of screening compounds for protein tyrosine phosphatase activity comprising the step of contacting a cell with the compound to be screened and measuring the protein tyrosine phosphatase activity and comparing the measured activity to the protein tyrosine phosphatase activity of a cell contacted with any one of compounds (I) thorough (VI).

BRIEF DESCRIPTION OF THE DRAWINGS

For a fuller understanding of the invention, reference should be made to the following detailed description, taken in connection with the accompanying drawings, in which:

FIG. 2 is an illustration of the molecular model of NSC-87877 binding to the Shp2 PTP domain.

FIG. 4 shows the inhibition of Shp2-dependent Erk1/2 activation by NSC-87877.

FIG. 6 is a series of histograms and immunoblots showing the inhibitory effects of NSC-87877 in EGF-stimulated MDA-MB-468 cells.

DETAILED DESCRIPTION OF THE PREFERRED EMBODIMENT

Figure 1A:
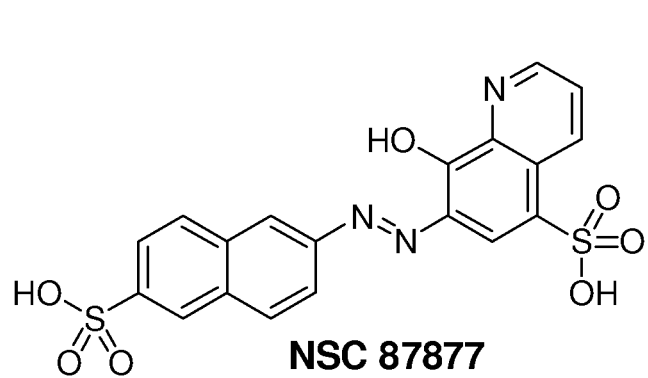
FIG. 1A is an illustration of the chemical structure of NSC-87877 (8-hydroxy-7-(6-sulfonaphthalen-2-yl)diazenyl-quinoline-5-sulfonic acid).

Shp2 is a non-receptor protein tyrosine phosphatase (PTP) encoded by the PTPN11 gene. It is involved in growth factor-induced activation of mitogen-activated protein (MAP) kinases Erk1 and Erk2 (Erk1/2) and has been implicated in the pathogenicity of the oncogenic bacterium *Helicobactor pylori* (*H. pylori*). Moreover, gain-of-function Shp2 mutations have been found in childhood leukemias and Noonan syndrome. Thus, small molecule Shp2 PTP inhibitors are much needed reagents for evaluation of Shp2 as a therapeutic target and for chemical biology studies of Shp2 function. By screening the National Cancer Institute (NCI) Diversity Set chemical library, NSC-87877 was identified as a potent Shp2 PTP inhibitor. Site-directed mutagenesis and molecular modeling studies suggested that NSC-87877 binds to the catalytic cleft of Shp2 PTP. NSC-87877 cross-inhibited Shp1 in vitro, but it was selective for Shp2 over other PTPs (PTP1B, HePTP, DEP1, CD45, and LAR). Importantly, NSC-87877 inhibited EGF-induced activation of Shp2 PTP, Ras, and Erk1/2 in cell cultures but did not block EGF-induced Gab1 tyrosine phosphorylation or Gab1-Shp2 association. Furthermore, NSC-87877 inhibited Erk1/2 activation by a Gab1-Shp2 chimera but did not affect the Shp2-independent Erk1/2 activation by phorbol 12-myristate 13-acetate (PMA). These results identified NSC-87877 as the first PTP inhibitor capable of inhibiting Shp2 PTP in cell cultures without a detectable off-target effect. This provides the first pharmacological evidence that Shp2 mediates EGF-induced Erk1/2 MAP kinase activation.

Definitions

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

As used herein, "treatment" refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, preventing or delaying spread (e.g., metastasis) of the cancer, preventing or delaying occurrence or recurrence of cancer, delay or slowing of cancer progression, amelioration of the cancer state, and remission (whether partial or total). The methods of the invention contemplate any one or more of these aspects of treatment.

A "subject in need of treatment" is a mammal with cancer that is life-threatening or that impairs health or shortens the lifespan of the mammal.

A "pharmaceutically acceptable" component is one that is suitable for use with humans and/or animals without undue adverse side effects (such as toxicity, irritation, and allergic response) commensurate with a reasonable benefit/risk ratio.

A "safe and effective amount" refers to the quantity of a component that is sufficient to yield a desired therapeutic response without undue adverse side effects (such as toxicity, irritation, or allergic response) commensurate with a reasonable benefit/risk ratio when used in the manner of this invention.

A "pharmaceutically acceptable carrier" is a carrier, such as a solvent, suspending agent or vehicle, for delivering the compound or compounds in question to the animal or human. The carrier may be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The invention is described below in examples which are intended to further describe the invention without limitation to its scope.

EXAMPLE 1

Identification of NSC-87877 as a Shp2 PTP Inhibitor.

Figure 1B:
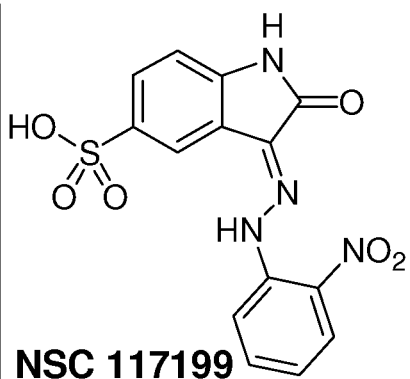
FIG. 1B is an illustration of the chemical structure of NSC-117199.

The NCI Diversity Set chemical library that contains 1981 compounds was screened for Shp2 PTP inhibitors using a GST-fusion protein of rodent Shp2 (GST-Shp2ΔN). Confirmed hits (>50% inhibition at 10 μM) that were either 1) organometallic agents, 2) arsenic compounds, 3) previously identified PTP inhibitors (NSC-668394, NSC-5069) (Lazo et al., 2002), 4) potential carcinogens, 5) with lower $IC_{50}$ for Shp1 than that for Shp2 in the initial analyses, 6) a nonspecific protein binding agent, or 7) polymers were excluded from further analysis. Authentic compounds of the remaining seven hits were either obtained from independent sources or synthesized in house and then compared to the samples from the NCI Diversity Set library for inhibition of GST-Shp2. Only one of these compounds, NSC-87877 (FIG. 1), showed a similar or greater potency than the sample of the same chemical identification obtained from NCI.

The PTP inhibitory activity of NSC-87877 was then assessed against several human PTPs in vitro. As shown in Table I, NSC-87877 potently inhibited Shp2 with an $IC_{50}$ of 0.318±0.049 (μM). NSC-87877 appeared to have no selectivity between human Shp2 and Shp1 in vitro. NSC-87877 showed approximately 5-, 24-, 206-, 266-, and 475-fold selectivity for Shp2 over PTP1B, HePTP, DEP1, CD45, and LAR (Table I).

EXAMPLE 2

NSC-87877 binds to the Shp2 Catalytic Cleft.

Figure 2A:
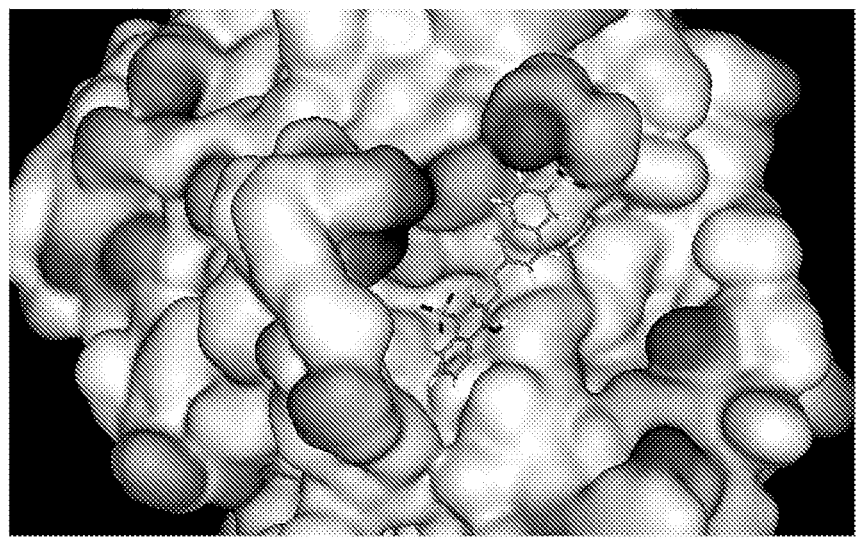
In FIG. 2A the protein surface of Shp2 PTP domain is shaded according to electrostatic potential.
Figure 2B:
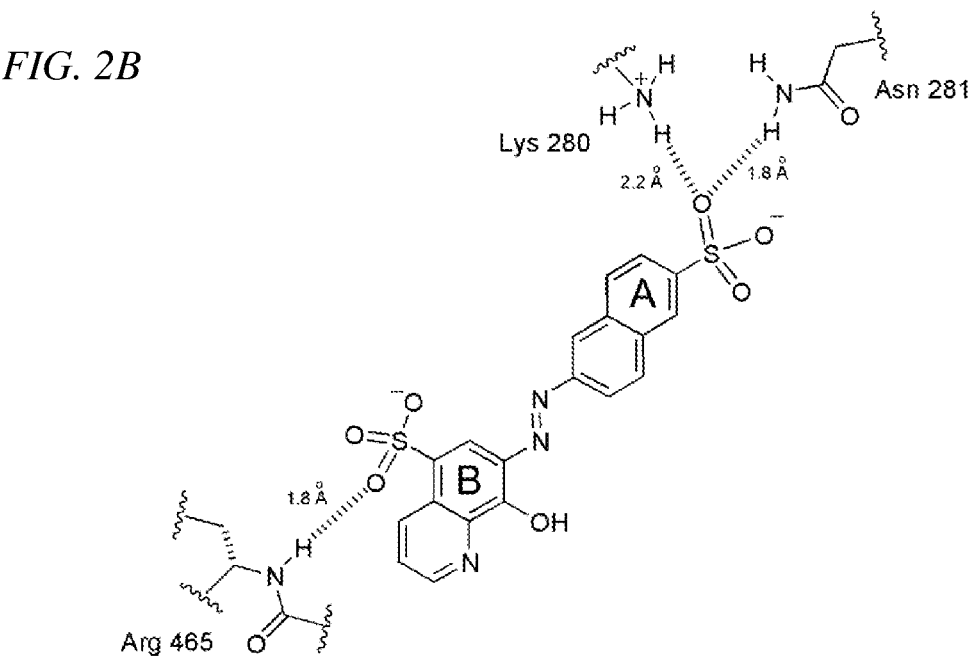
In FIG. 2B there is provided an illustration of the hydrogen bonds formed between the NSC-87877 and the protein, via Arg-465, Lys-280 and Asn-281 are shown schematically but not to scale. The hydrogen bonds are defined with a minimum donor angle of 900 and minimum acceptor angle of 60° and maximum length of 2.5 Å.

NSC-87877 ranked among top 10% ($175^{th}$) of the compounds with the best GLIDE scores for the docking to the human Shp2 PTP domain in our virtual screening of 2368 3D structures derived from the NCI Diversity Set. Computer docking of NSC-87877 (FIG. 2) suggested that the B-ring sulfonic acid group forms hydrogen bond with the backbone NH group of Arg-465. Arg-465 is a conserved residue in the PTP signature motif (motif 9) VHCSXGXGR[T/S]G located at the base of the PTP catalytic cleft (Andersen et al., 2001). The A-ring sulfonic acid forms hydrogen bonds with the side-chain $NH_3$ group of Lys-280 and the side-chain $NH_2$ group of Asn-281. Lys-280/Asn-281 are non-conserved PTP residues located adjacent to the phosphotyrosine recognition loop (motif 1) (Andersen et al., 2001). The interaction between aromatic rings of the compound and the protein contributes to the binding through hydrophobic stabilization.

Figure 8:
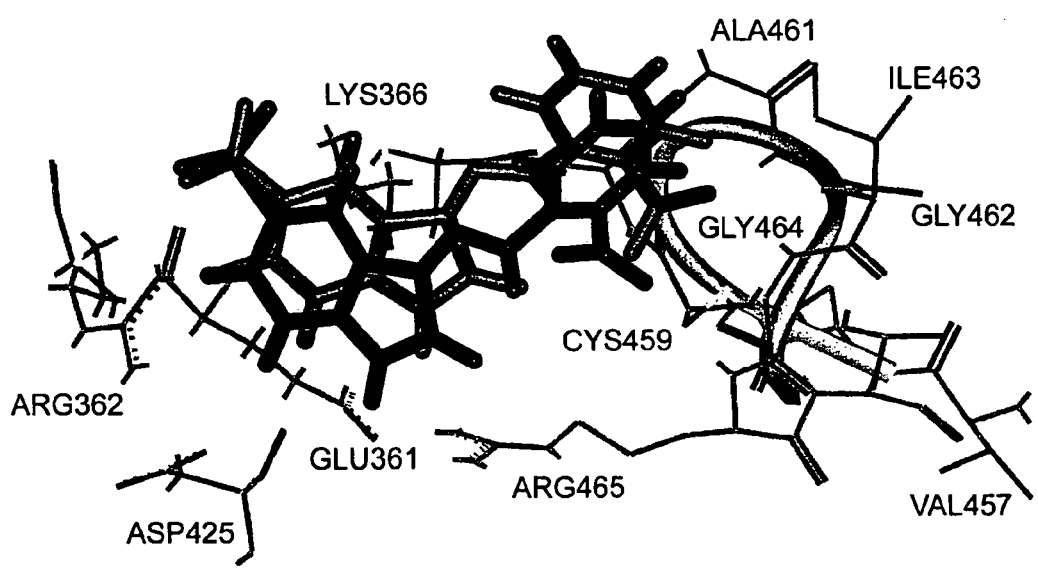
FIG. 8 is an illustration of an overlay of NSC-117199 (dark-shaded chemical structure) and HL2-052-2 (light-shaded chemical structure) in the SHP2 active site.

NSC-117199 was docked to the catalytic site of Shp2 in the same way (See FIG. 8). The docked structure, along with the analog HL2-052-2 (see Table II) is shown in FIG. 8. This formed the basis of the design of the library of NSC-117199 analogs (with the isatin core) as shown in the compound Table (Table II). The anionic goups on the isatin bind to the phosphate binding site of the PTP loop (shown as the grey tube in FIG. 8) and to Arg262, Lys364 and Lys 366.

TABLE I

Inhibition of PTPs by NSC-87877 in vitro

| PTP | $IC_{50}$* (μM) | Selectivity (fold) |
| --- | --- | --- |
| Shp2 | 0.318 ± 0.049 (N = 11) | 1 |
| Shp1 | 0.355 ± 0.073 (N = 5) | 1 |
| PTP1B | 1.691 ± 0.407 (N = 4) | 5 |
| HePTP | 7.745 ± 1.561 (N = 4) | 24 |
| DEP1 | 65.617 ± 4.120 (N = 3) | 206 |
| CD45 | 84.473 ± 16.185 (N = 3) | 266 |
| LAR | 150.930 ± 9.077 (N = 4) | 475 |
| Shp2V280 | 1.110 ± 0.136 (N = 6) | 3 |
| Shp2RD | 1.087 ± 0.162 (N = 6) | 3 |

To evaluate this molecular model, we made two Shp2 PTP mutants containing changes in the Lys-280 and Asn-281 residues predicted to interact with NSC-87877. One (Shp2V280) mutant contained a Lys-280 to Val-280 mutation and the other (Shp2RD) mutant contained dual Lys-280/Asn-281 to Arg-280/Asp-281 mutations. In silico prediction gave both Shp2V280 and Shp2RD mutants a 0.6 kcal/mole increase (destabilization) in the GLIDE docking score. Sensitivity of mutated and wild-type Shp2 to NSC-87877 inhibition was then compared experimentally by the PTP assay. As shown in Table I, Shp2V280 and Shp2RD were approximately 3-fold less sensitive to NSC-87877 inhibition (p=0.0015 for comparison of $IC_{50s}$ between Shp2 and Shp2V280; p=0.0062 for comparison of $IC_{50s}$ between Shp2 and Shp2RD). These data suggest that Lys-280 and/or Asn-281 are involved in NSC-87877 binding to Shp2.

EXAMPLE 3

NSC-87877 Inhibits EGF-Stimulated Shp2 Activation.

Figure 3:
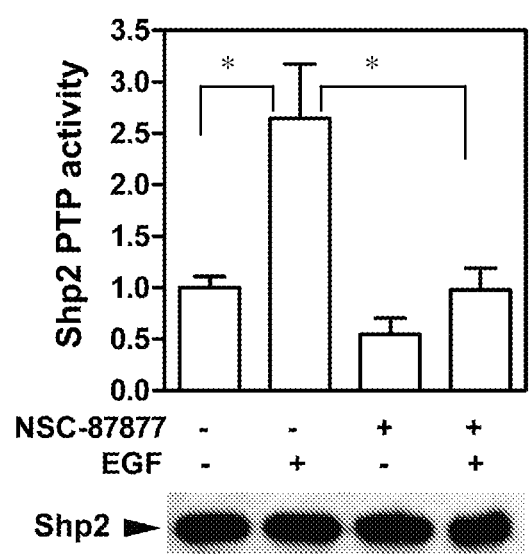
FIG. 3 is an illustration of the inhibition of EGF-stimulated Shp2 activation by NSC-87877. Serum-starved HEK293 cells were pretreated with or without NSC-87877 (50 μM), stimulated with EGF or mock-treated, and Shp2 PTP activity was determined by the immune complex Shp2 PTP assay. The relative Shp2 PTP activity is shown in the histogram. Data were from two independent experiments performed in duplicate (n=4). After determination of Shp2 PTP activity, Shp2 immunoprecipitates were analyzed by immunoblotting with an antibody to Shp2 (bottom panel beneath the histogram). *, p<0.05.

To determine if NSC-87877 is able to inhibit Shp2 in the cells, serum-starved HEK293 cells were pre-incubated with or without NSC-87877 and then stimulated with EGF or mock-treated. Shp2 was immunoprecipitated from cell lysates and Shp2 PTP activity was then determined in the immune complexes using DiFMUP as the substrate. Shp2 PTP activity increased 2.6-fold in response to EGF stimulation in the absence of NSC-87877 pretreatment (FIG. 3). Incubation of NSC-87877 alone reduced the basal Shp2 PTP activity by 45%. The EGF-stimulated Shp2 activation was inhibited by 97% when cells were pretreated with 50 μM NSC-87877 (FIG. 3).

EXAMPLE 4

NSC-87877 Inhibits EGF-Induced Erk1/2 Activation.

Figure 4A:
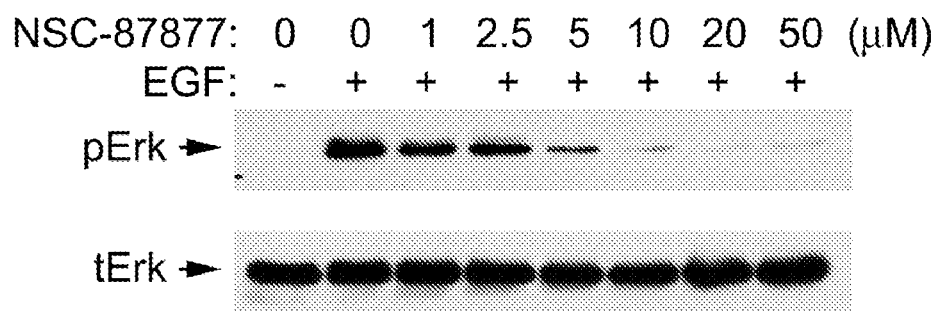
FIG. 4A is an immunoblot. Serum-starved HEK293 cells were pretreated with various concentrations of NSC-87877 (0-50 μM) for 3 h and then stimulated with EGF (1 ng/ml, 5 min). Erk1/2 activation was analyzed by immunoblotting of cell lysate supernatants (20 μg/each) with antibodies to phosphorylated, active Erk1/2 (pErk) or total Erk2 (tErk).

Molecular biology studies using overexpression of a PTP-inactive Shp2 mutant have suggested that Shp2 is involved in EGF-induced Erk1/2 activation (Deb et al., 1998). To evaluate if NSC-87877 could inhibit Shp2-dependent cell signaling in the cells, we examined the effect of NSC-87877 on EGF-stimulated Erk1/2 activation. Serum-starved HEK293 cells were pretreated with 0-50 μM NSC-87877 for 3 h and then stimulated with EGF for 5 min. Erk1/2 activation was determined by immunoblotting analysis of cell lysates with an anti-phospho-Erk1/2 antibody. As shown in FIG. 4A, NSC-87877 inhibited EGF-stimulated Erk1/2 activation in a concentration dependent manner. A 50% inhibition of EGF-stimulated Erk1/2 activation was observed at an average of 6 μM NSC-87877 in two independent experiments.

EXAMPLE 5

NSC-87877 Suppresses Erk1/2 Activation by a Gab1-Shp2 Chimera but does not Affect PMA-Induced Erk1/2 Activation.

Figure 4B:
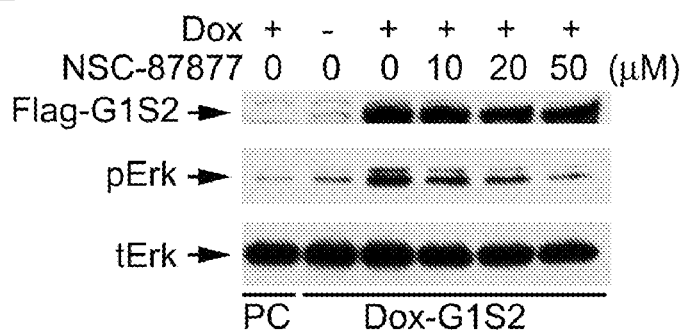
FIG. 4B is a second immunoblot. Flp-In-T-Rex-293 cell line containing dox-inducible Gab1PH-Shp2ΔN (Dox-G1S2) was incubated in serum-free medium with or without dox (2 μg/ml) in the presence of indicated concentration of NSC-87877 for 3 h. Cell lysates were analyzed by immunoblotting with antibody to Flag-tag (for detection of Gab1PH-Shp2ΔN), active Erk1/2 (pErk), or total Erk2 (tErk). PC, parental Flp-In-Rex-293 cells. Flag-G1S2, Flag-Gab1PH-Shp2ΔN cells.

It has been observed that expression of a chimeric protein (Gab1PH-Shp2ΔN) consisting of the Gab1 PH domain and a constitutively active Shp2 N-SH2 domain deletion mutant resulted in Erk1/2 activation and that the Shp2 PTP activity is necessary for Erk1/2 activation by Gab1PH-Shp2ΔN (Cunnick et al., 2002). To examine if NSC-87877 could inhibit Shp2-dependent Erk1/2 activation that bypasses the ligand-receptor interaction, HEK293-derived cell lines (dox-G1S2) containing dox-inducible Gab1PH-Shp2ΔN were established using the Flp-In-T-Rex-293 cells. FIG. 4B (top panel) shows a representative dox-G1S2 cell line that demonstrated the property of dox-inducible expression of Flag-tagged Gab1PH-Shp2ΔN. In the absence of dox, there was little, residual level of Gab1PH-Shp2ΔN in the cells and the level of active Erk1/2 was minimal. Induction of cells with dox induced Gab1PH-Shp2 AN expression and Erk1/2 activation (FIG. 4B). However, in NSC-87877 treated cells, Erk1/2 activation by Gab1PH-Shp2ΔN was inhibited. Coupled with data from FIGS. 3 and 4A, this result suggests that the mechanism by which NSC-87877 inhibits EGF-induced Erk1/2 activation is not mediated by events upstream of Shp2 such as activation of EGF receptor. Furthermore, since there was no extracellular stimulation involved in the Erk1/2 activation by Gab1PH-Shp2ΔN, the observation that NSC-87877 could inhibit Gab1PH-Shp2ΔN-induced Erk1/2 activation indicates that the target of NSC-87877 is intracellular.

Figure 4C:
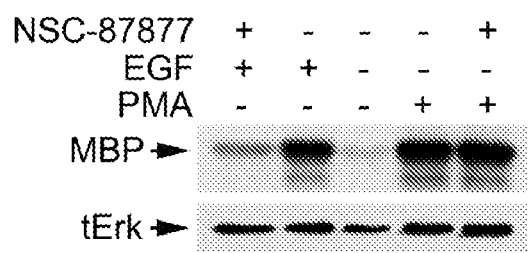
FIG. 4C is a third immunoblot. HEK293 cells were pretreated with or without NSC-87877 (20 μM, 3 h) and then stimulated with EGF (1 ng/ml, 5 min) or PMA (100 nM, 10 min). Erk1/2 was immunoprecipitated from cell lysate supernatants (100 μg/each) and Erk1/2 kinase activity was determined by phosphorylating myelin basic protein (MBP) with [γ-$^{32}$P]ATP. After the kinase reaction, reaction mixtures were separated on a SDS-polyacrylamide gel, transferred onto a nitrocellulose filter, and subjected to autoradiography. After autoradiography, the filter was used for immunoblotting analysis with an antibody to Erk2 (tErk) to examine the amounts of Erk2 in immunoprecipitates.

Previous studies have shown that PMA-induced Erk1/2 activation is not affected by overexpression of a PTP-inactive Shp2 mutant (Yamauchi et al., 1995), suggesting that the protein kinase C (PKC) activator-mediated Erk1/2 activation is Shp2-independent. We, therefore, compared the effect of NSC-87877 on EGF- and PMA-stimulated Erk1/2 activation. Consistent with data presented in FIG. 4A, EGF-stimulated Erk1/2 activation was inhibited by NSC-87877 (FIG. 4C). In contrast, NSC-87877 did not affect PMA-induced Erk1/2 activation (FIG. 4C). PKC is known to activate the Erk1/2 MAP kinase cascade by directly phosphorylating Raf-1 (Carroll and May, 1994; Kolch et al., 1993). Thus, our data that NSC-87877 inhibited EGF-induced, but not PMA-induced, Erk1/2 activation, suggest that the target of NSC-87877 is upstream of Raf-1, consistent with the notion that NSC-87877 is acting on Shp2 to inhibit Erk1/2 activation.

EXAMPLE 6

NSC-87877 does not Inhibit EGF-Induced Gab1 tyrosine phosphorylation and Gab1-Shp2 Association.

Figure 5:
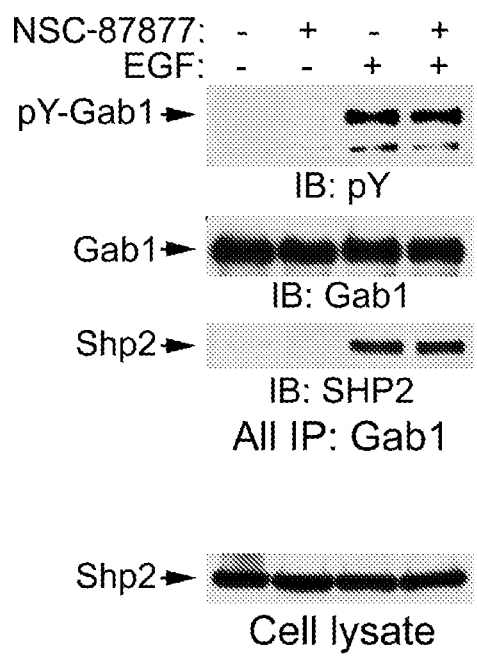
FIG. 5 shows that NSC-87877 has no apparent effect on signaling steps prior to Shp2 activation in EGF-stimulated cells. HEK293 cells were serum-starved for 18 h, pre-incubated with or without NSC-87877 (20 μM, 3 h), and then treated with EGF (5 ng/ml, 5 min) or BSA (-). Gab1 was immunoprecipitated from cell lysate supernatants. Immunoprecipitates were analyzed by immunoblotting with antibodies to phosphotyrosine (pY), Gab1, or Shp2. An aliquot of each cell lysate supernatant (30 μg) was also examined by immunoblotting with an antibody to Shp2 (bottom panel). pY-Gab1, tyrosine-phosphorylated Gab1.

Shp2 is activated in EGF-stimulated cells by binding to tyrosine-phosphorylated Gab1 (and Gab2 if it is also expressed) (Cunnick et al., 2001). To further assess if NSC-87877 has an off-target effect upstream of Shp2 activation in the EGF-stimulated cells, we analyzed EGF-induced Gab1 tyrosine phosphorylation and Gab1-Shp2 association in HEK293 cells treated with NSC-87877 and/or EGF. HEK293 cells express Gab1 but not Gab2. FIG. 5 shows that Gab1 was not tyrosine-phosphorylated and Shp2 was not detected in Gab1 immunoprecipitates in the absence of EGF stimulation. Gab1 became tyrosine-phosphorylated and Shp2 was co-immunoprecipitated with Gab1 upon stimulation of cells with EGF. FIG. 5 also shows that NSC-87877 did not inhibit EGF-stimulated Gab1 tyrosine phosphorylation and subsequent binding of Shp2 to Gab1. Immunoblotting analysis of cell lysate supernatants used for immunoprecipitation of Gab1 indicated that an equal amount of Shp2 was present in each sample (FIG. 5, bottom panel). These results indicate that NSC-87877 does not affect EGF-activated signaling steps prior to Shp2 activation.

EXAMPLE 7

NSC-87877 Inhibits EGF-Stimulated Shp2 PTP, Ras, and Erk1/2 Activation in MDA-MB-468 Cells that Co-Express Shp2 and Shp1.

Figure 6A:
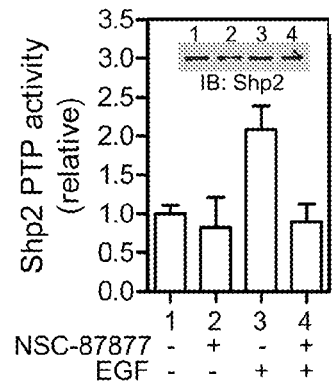
FIGS. 6A and 6B are a pair of histograms. Serum-starved MDA-MB-468 cells were treated with NSC-87877 and EGF as indicated and Shp2 (A) and Shp1 PTP activities were determined by the immune complex PTP assay. The relative PTP activities are shown (n=4).
Figure 6B:
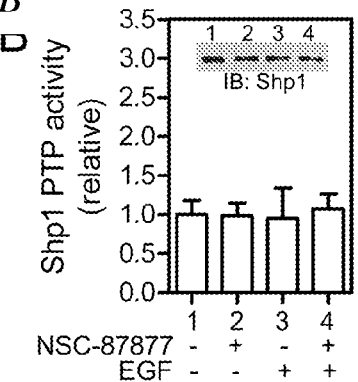

HEK293 cells express Shp2 but not Shp1. Since NSC-87877 inhibits Shp2 and Shp1 with the similar $IC_{50}$ in vitro, we next tested the inhibitory effect of NSC-87877 on EGF signaling in MDA-MB-468 cells that express both Shp2 and Shp1. Near confluent MDA-MB-468 cells were serum-starved, pretreated with NSC-87877 or solvent, and then stimulated with EGF. Shp2 and Shp1 were immunoprecipitated from cell lysates and their PTP activities were determined by the immune complex PTP assay. Similar to that observed in HE 293 cells, EGF induced Shp2 activation in MDA-MB-468 cells and NSC-87877 inhibited the EGF-induced Shp2 PTP activity in these cells (FIG. 6A). Shp1 immunoprecipitated from serum-starved MDA-MB-468 cells had a similar low basal PTP activity as that of Shp2. Interestingly, EGF did not induce Shp1 activation in repeated experiments (FIG. 6B).

Figure 6C:
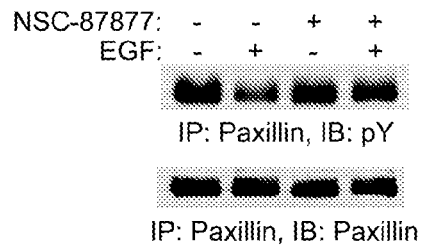
In FIG. 6C paxillin was immunoprecipitated from serum-starved MDA-MB-468 cells treated with NSC-87877 and EGF as indicated. Paxillin immunoprecipitates was analyzed by immunoblotting with antibodies to phosphotyrosine (top panel) or paxillin (bottom panel).
Figure 6D:
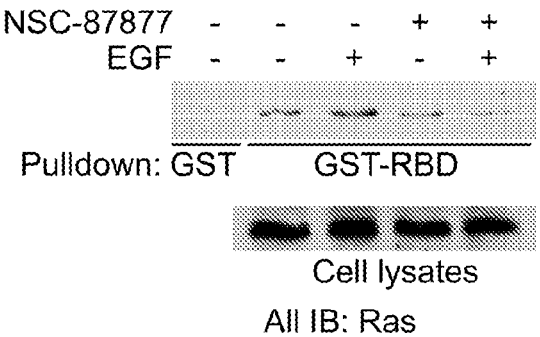
FIG. 6D is an immunoblot. Serum-starved MDA-MB-468 cells were treated with NSC-87877 and EGF as indicated. Cleared cell lysates (0.2 mg protein/each) were incubated with GST-agarose (control) or GST-RBD-agarose to pull down active-Ras-GTP, which was visualized by immunoblotting with an anti-Ras antibody (top panel). Bottom panel, immunoblotting analysis of an equal amount of cell lysates (100 μg/each) with an anti-Ras antibody.
Figure 6E:
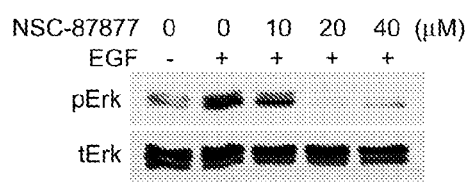
FIG. 6E is another immunoblot. Serum-starved MDA-MB-468 cells were treated with indicated concentrations of NSC-87877 for 3 h and stimulated with EGF (2 ng/ml, 10 min) or mocked treated. Cell lysates (20 μg/each) were analyzed by immunoblotting with antibodies to phospho-Erk1/2 or total Erk1/2.

Paxillin is a physiological substrate of Shp2 (Ren et al., 2004). As shown in FIG. 6C, EGF-induced paxillin dephosphorylation in MDA-MB-468 cells, which was inhibited by NSC-87877. Thus, inhibition of Shp2 PTP activity by NSC-87877 in MDA-MB-468 cells blocked dephosphorylation of its protein substrate in these cells, demonstrating a direct functional consequence of Shp2 inhibition. Shp2 functions upstream of Ras in the Ras-Erk1/2 MAP kinase pathway (Neel et al., 2003). To determine if NSC-87877 could inhibit Ras activation, EGF-induced Ras activation in MDA-MB-468 cells was analyzed by the GST-RBD pulldown assay. As shown in FIG. 6D, more active Ras was pulled down by GST-RBD in EGF-stimulated cells than that in serum-starved cells, indicating that Ras was activated in EGF-stimulated cells. However, if cells were pretreated with NSC-87877, EGF-induced Ras activation was blocked (FIG. 6D). Consistently, EGF-induced Erk1/2 activation was inhibited by NSC-87877 in MDA-MB-468 cells (FIG. 6E). Thus, NSC-87877 can inhibit EGF-stimulated Erk1/2 activation in MDA-MB-468 cells that co-express Shp2 and Shp1.

While molecular biology and genetic evidence has suggested that Shp2 plays important roles in growth factor and cytokine signaling and that Shp2 mutations are linked to human diseases, chemical biology interrogation of Shp2 function and signaling mechanisms had not been possible due to the lack of a suitable Shp2 inhibitor. NSC-87877 has been identified herein as a potent Shp2 inhibitor and has been demonstrated to inhibit Shp2 PTP activity and Shp2-mediated Erk1/2 activation in intact cell models. This represents the first successful effort of identification of a Shp2 PTP inhibitor that is effective in inhibiting Shp2-dependent Erk1/2 activation in the cells. The present invention also provides the first pharmacological evidence that Shp2 PTP is involved in growth factor-stimulated Erk1/2 activation. This important discovery opens a new avenue in Shp2 research by providing a novel tool for chemical biology exploration of Shp2 function and signaling mechanisms.

The in vitro PTP assays show that NSC-87877 inhibits Shp2 selectively over PTP1B, HePTP, DEP1, CD45, and LAR, but it inhibits Shp2 and Shp1 with a similar potency. Development of a Shp2-specific inhibitor that does not cross-inhibit Shp1 is a future aim. Nevertheless, the present invention illustrates that a Shp2 PTP inhibitor without selectivity between Shp2 and Shp1 could still be a useful reagent for targeting Shp2 over other PTP inhibitors due in part to the differential expression of Shp1 and Shp2. Unlike Shp2, which is ubiquitously expressed, Shp1 expression is limited to hematopoietic cells and certain epithelial cells. Furthermore, Shp1 is epigenetically silenced in some leukemias and lymphomas (Oka et al., 2002). Shp1 PTP inhibition activity becomes irrelevant in cells that do not express Shp1 or contain a minimal amount of Shp1. While Shp1 negatively regulates cytokine and immune receptor signaling in hematopoietic cells, the role of Shp1 in epithelial cells is less clear. Expression of exogenous wildtype or PTP-inactive Shp1 in HEK293 cells was found to have little effect on the Erk1/2-dependent Elk-1 activation by EGF (Bennett et al., 1996). Interestingly, the present data show that EGF activates Shp2 but not Shp1 in the MDA-MB-468 human breast carcinoma cells. Thus, even in certain cells where Shp1 is present, it may not play a significant role in a particular signaling pathway. Under this condition, a Shp2 inhibitor without selectivity between Shp1 and Shp2 can be used to analyze or control Shp2 function.

NSC-87877 contains two arylsulfonic acid groups, one as naphthylsulfonic acid and the other as quinolinesulfonic acid. The arylsulfonic acid moiety has been identified as a pharmacophore of PTP inhibitors (Huang et al., 2003; McCain et al., 2004). In fact, suramin, a hexasulfonated polyaromatic naphthylurea, and several polysulfonic derivatives of suramin that contain multiple naphthylsulfonic acid groups or phenylsulfonic acid groups, are PTP inhibitors in vitro (McCain et al., 2004). Although negatively charged arylsulfonic acids were thought to be unfavorable for cellular uptake, compounds containing multiple arylsulfonyl acid groups capable of entering cells are not without precedent. For instance, suramin, which has six arylsulfonic acid groups, can enter cells through an active process (Stein, 1993). Whereas the means by which NSC-87877 enters cells requires further investigation, it is possible that it may not occur by passive diffusion but rather through an active process. Consistent with this notion, we noticed that it was necessary to incubate cells with NSC-87877 for 2-3 h in order to observe the inhibitory effects of NSC-87877 in the cells, suggesting that NSC-87877 cannot rapidly diffuse into cells.

Because of the similarity between Shp1 and Shp2, development of a Shp2-specific inhibitor will be challenging but not impossible. Selectivity between Shp1 and Shp2 (either towards Shp1 or towards Shp2) was observed among several hits from the NCI Diversity Set chemical library (our unpublished data). Shp1 and Shp2 catalytic domains are known to have different substrate specificity (O'Reilly and Neel, 1998), suggesting that the catalytic cleft is not identical between Shp1 and Shp2. Furthermore, the surface electrostatic potential of the catalytic cleft is much more positive in human Shp2 than in human Shp1 (Yang et al., 1998). The PTP catalytic cleft consists of a base and four sides in the 3D structures (Hof et al., 1998; Yang et al., 2003). Although amino acid residues present at the base of Shp1 and Shp2 PTP catalytic clefts are identical, all four sides of the catalytic cleft contains one or more residues that are different between Shp1 and Shp2. These differences will provide the basis for developing an Shp2-specific PTP inhibitor in our continuing effort.

Materials and Methods

Chemical Library: The NCI Diversity Set chemical library of 1981 compounds was provided by the NCI Developmental Therapeutics Program. Information about the Diversity Set is available at http://www.dtp.nci.nih.gov/branches/dscb/diversity_exylanation.html. After the initial identification of NSC-87877 from the NCI Diversity Set, the authentic, 98% pure NSC-87877 [8-hydroxy-7-(6-sulfonaphthalen-2-yl)diazenyl-quinoline-5-sulfonic acid] was obtained from Acros for subsequent experiments.

Recombinant PTP Proteins: Plasmids for expression of glutathione S-transferase (GST)-PTP fusion proteins of human Shp2 (residues 205-593), Shp1 (residues 205-597), and PTP1B (residues 1-435) were constructed in pGEX-2T by PCR subcloning techniques. A plasmid for GST fusion protein of human HePTP (residues 1-399) was constructed in pGEX-2T-KG. GST-Shp2 PTP containing Lys-280 to Val (V280) and Lys-280/Asn-281 to Arg/Asp (R280D281) mutants were generated by PCR-based mutagenesis. All constructs were verified by DNA sequencing.

GST-PTP fusion proteins were expressed in *E. coli* DH5α and affinity purified with glutathione Sepharose. After elution from glutathione affinity column, GST-fusion proteins were dialyzed with dialysis buffer (12.5 mM Tris-Cl, pH 7.5, 25 mM NaCl, 1 mM dithiothreitol (DTT), and 0.1% β-mercaptoethanol) at 4° C. for 40 h and then stored in dialysis buffer plus 20% glycerol at −80° C. Recombinant CD45 (residues 584-1281) and LAR D1 domain were obtained from Calbiochem. Recombinant DEP1 was from Abcam. GST fusion proteins of murine Shp2 (GST-Shp2ΔN) and Shp1 have been reported (Cunnick et al., 1998; Cunnick et al., 2001) and were used in the chemical library screening and initial in vitro characterization.

PTP Activity Assay: PTP activity was measured using the fluorogenic 6,8-difluoro-4-methylumbelliferyl phosphate (DiFMUP, from Invitrogen) as the substrate. Unless otherwise specified, each reaction contained 25 mM MOPS (pH 7.0), 50 mM NaCl, 0.05% Tween-20, 1 mM DTT, 20 μM DiFMUP, 10 nM Microcystin LR, 20 nM GST-PTP, and 5 μl test compound or dimethyl sulfoxide (DMSO, solvent) in a total reaction volume of 100 μl in black 96-well plates. Reaction was initiated by addition of DiFMUP and the incubation time was 30 min at room temperature. DiFMU fluorescence signal was measured at an excitation of 355 nm and an emission of 460 nm with a Wallac Victor$^2$ 1420 plate reader. $IC_{50}$ was defined as the concentration of an inhibitor that caused a 50% decrease in the PTP activity. For $IC_{50}$ determination, 8 concentrations of NSC-87877 at ⅓ dilution (~0.5 log) were tested. The ranges of NSC-87877 concentrations used in each PTP assay were determined from preliminary trials. Each experiment was performed in triplicate and $IC_{50}$ data were derived from at least three independent experiments. The curve-fitting program Prism 4 (GraphPad Software) was used to calculate the $IC_{50}$ value.

Computer Docking: Computer docking was performed using the X-ray crystal structure of human Shp2 (PDB identification code: 2SHP) (Hof et al., 1998) using the GLIDE (Grid-Based Ligand Docking from Energetics, as part of the FirstDiscovery Suite from Schrödinger, L.L.C.) program (Friesner et al., 2004; Halgren et al., 2004). The N-SH2 domain of Shp2, which blocks the catalytic site, was removed from the 3D structure prior to the computer docking analysis. The GLIDE program relies on the Jorgensen OPLS-2001 force field. The optimal binding geometry for each model was obtained by utilization of Monte Carlo sampling techniques coupled with energy minimization.

Preparation of HEK293 Cell Line for Doxycycline-inducible Expression of a Gab1-Shp2 Chimera: Plasmid pcDNA5/FRT/TO-Gab1PH-Shp2ΔN was constructed by subcloning the coding sequence for Flag-Gab1PH-Shp2ΔN (Cunnick et al., 2002) from pcDNA3.1 into pcDNA5/FRT/TO (Invitrogen) through HindIII and ApaI sites. pcDNA5/FRT/TO-Gab1PH-Shp2ΔN and pOG44 was then co-transfected into the Flp-In-T-Rex-293 cells (Invitrogen). Transfected cells were selected in Dulbecco's modified Eagle medium (DMEM)/10% tetracycline-free fetal bovine serum (FBS) medium containing 100 μg/ml hygromycin. Individual Hygromycin-resistant cell lines were screened for dox-inducible expression of Flag-tagged Gab1PH-Shp2ΔN by immunoblotting analysis of cell lysates with an anti-Flag antibody (M2, from Sigma). Among 24 hygromycin-resistant cell lines that we have screened, 21 cell lines showed dox-inducible expression of Gab1PH-Shp2ΔN. One of these 21 cell lines was randomly selected for use in the subsequent experiments.

Cell Culture, Immunoprecipitation and Immunoblotting: Cells were cultured in DMEM/10% FBS. Sub-confluent cells were serum-starved in DMEM/0.1% BSA for 18 h prior to treatment with NSC-87877 and stimulation with EGF or PMA. Cells were lysed on ice with Lysis Buffer A (50 mM Tris-HCl, pH 7.5, 150 mM NaCl, 1 mM EDTA, 1 mM EGTA, 25 mM NaF, 5 mM sodium pyrophosphate, 1 mM DTT, 20 mM p-nitrophenyl phosphate, 1% Triton X-100). Immunoprecipitation and immunoblotting analyses of Gab1, Shp2, paxillin, and Erk1/2 were performed essentially as described (Cunnick et al., 2001; Ren et al., 2004). Erk1/2 kinase assay was performed as reported except that endogenous Erk1/2 kinase activity was measured (Cunnick et al., 2001).

Immune Complex PTP Assay: Serum-starved cells were pretreated with NSC-87877 (50 µM, 3 h) or DMSO (solvent) and then stimulated with EGF (100 ng/ml, 5 min) or left untreated. Cells were lysed in ice-cold PTP Lysis Buffer [25 mM Hepes pH7.4, 150 mM NaCl, 2 mM EDTA, 0.5% Triton X-100, 1:50 diluted protease inhibitor cocktail (Roche)]. Shp2 or Shp1 in cell lysate supernatants (0.5 mg/each) was immunoprecipitated with an antibody to Shp2 or an antibody to Shp1 (Santa Cruz) plus Protein A-Sepharose for 2 h at 4 C. Immunoprecipitates were washed twice with the PTP lysis buffer and twice with Reaction Buffer (20 mM Hepes pH 7.4, 1 mM EDTA, 5% Glycerol, 1 mM DTT) (Tartaglia et al., 2003). Each Shp2 or Shp1 immune complex was resuspended in 100 µl Reaction Buffer containing 50 µM DiFMUP and then incubated at room temperature for 20 min. After a brief centrifugation, supernatants were transferred into 96-well plates and the DiFMU fluorescence signal was measured. The remaining immune complexes were used for immunoblotting analysis of Shp2 or Shp1.

Ras Activation Assay: Active Ras in MDA-MB-468 cells was detected by means of Ras-GTP bound to a GST fusion protein of the Ras-GTP binding domain of Raf fragment (GST-RBD) (Cunnick et al., 2002) followed by immunoblotting with an anti-Ras antibody (Santa Cruz).

Statistical Analysis: Statistical analyses were performed using unpaired t test with Welch's correction using the GraphPad Prism 4 program (GraphPad Software).

Development of Additional Inhibitors of Shp2 protein tyrosine kinase.

The following is a series of compounds that were synthesized based upon the NSC87877 and NSC 117199. See Table 2 for a further listing of the compounds. Percent PTP activity and $IC_{50}$ for each of the compunds was determined as outlined above for NSC87877.

2,3-Dioxo-2,3-dihydro-1H-indole-5-sulfonyl chloride[1] (rpm121)

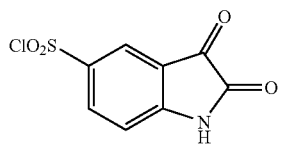 [SMILES: O=C1Nc2ccc(S(=O)(=O)Cl)cc2C1=O]

Phosphorus oxychloride (27.17 g, 177.2 mmol) was added to a mixture of 5-isatinsulfonic acid sodium salt dihydrate (10.1 g, 35.5 mmol) in of tetramethylene sulfone (50 ml). The resulting mixture was stirred at 60° C. for 3 h. After cooling to 0° C., water (120 ml) was added. The green precipitate was filtered, dissolved in ethyl acetate (200 ml) and washed with water (150 ml). The organic extracts were collected, dried over $Na_2SO_4$, filtered and the solvent removed under reduced pressure, to provide a green solid. The pure compound rpm121 was obtained after recrystallization from ethyl acetate/hexane 1:1 as yellow solid (5.9 g, 21.1 mmol, 68%). $^1$H NMR (400 MHz, $CDCl_3$:$CD_3CN$ 1:1) δ 7.22 (1H, d, J 8.4 Hz), 8.16 (1H, d, J 2.0 Hz), 8.23 (1H, dd, J 8.4, 2.0 Hz), 9.47 (1H, s), mp 200-202° C.

2,3-Dioxo-2,3-dihydro-1H-indole-5-sulfonic acid dimethylamide[1] (rpm123)

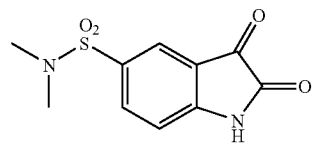

A mixture of dimethylamine (2M solution in THF) (0.668 mmol, 1.3 eq) and DIPEA (0.139 g, 1.02 mmol, 2 eq) was added to a solution of rpm121 (0.126 g, 0.514 mmol) in anhydrous THF (4 ml) at 0° C. under Ar. The reaction mixture was stirred overnight at room temperature, and the mixture was poured into water (5 ml). The product was extracted with ethyl acetate (3×10 ml). The organic extracts were collected, dried over $Na_2SO_4$ and the solvent removed under reduced pressure. The pure compound rpm123 was obtained after trituration with ethyl acetate (5 ml) as a yellow solid (0.90 g, 0.354 mmol, 68%), mp 150-152° C. (lit mp 233° C.) $^1$H NMR (400 MHz, DMSO-$d_6$) δ 2.60 (6H, s), 7.09 (1H, d, J 8.3 Hz), 7.68 (1H, d, J 2.0 Hz), 7.91 (1H, dd, J 8.3, 2.0 Hz), 11.44 (1H, s).

2,3-Dioxo-2,3-dihydro-1H-indole-5-sulfoniamide (rpm125).

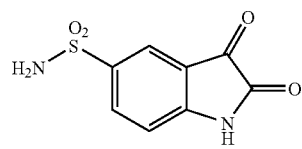 [SMILES: NS(=O)(=O)c1ccc2c(c1)C(=O)C(=O)N2]

This was obtained from rpm121 and ammonia (2 M solution in ethanol) in a similar manner as described for preparation of rpm123. The pure compound rpm125 was obtained after trituration with ethyl acetate as a yellow solid (47%), mp 200° C. (dec). $^1$H NMR (400 MHz, DMSO-$d_6$) δ 7.02 (1H, d, J 8.2 Hz), 7.38 (2H, s,), 7.82 (1H, d, J 1.8 Hz), 7.95 (1H, dd, J 8.2, 1.8 Hz), 11.35 (1H, s).

2,3-Dioxo-2,3-dihydro-1H-indole-5-sulfonic acid 4-methoxybenzylamide (rpm126).

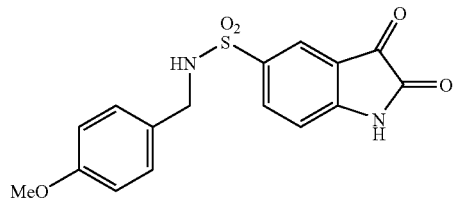 [SMILES: COc1ccc(CNS(=O)(=O)c2ccc3c(c2)C(=O)C(=O)N3)cc1]

This was obtained from rpm121 and 4-methoxybenzylamine in a similar manner as described for preparation of rpm123. The pure compound rpm126 was obtained after trituration ethyl acetate as a yellow solid (25%), mp 230° C. (dec). $^1$H NMR (400 MHz, DMSO-d$_6$) δ 3.66 (3H, s), 3.89 (2H, d, J 6.1 Hz), 6.77 (2H, d, J 8.8 Hz), 6.98 (1H, d, J 8.0 Hz), 7.08 (2H, d, J 8.8 Hz), 7.65 (1H, d, J 2.0 Hz), 7.88 (1H, dd, J 8.0, 2.0 Hz), 8.06 (1H, t, J 6.1 Hz), 11.39 (1H, s).

2,3-Dioxo-2,3-dihydro-1H-indole-5-sulfonic acid 4-chlorobenzylamide (rpm127)

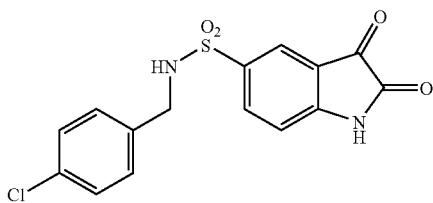 [SMILES: O=C1Nc2ccc(S(=O)(=O)NCc3ccc(Cl)cc3)cc2C1=O]

This was obtained from rpm121 and 4-chlorobenzylamine in a similar manner as described for preparation of rpm123. The pure compound rpm127 was obtained after trituration with ethyl acetate as a yellow solid (57%), mp 250° C. (dec). $^1$H NMR (400 MHz, DMSO-d$_6$) δ 3.97 (2H, d, J 6.2 Hz), 7.00 (1H, d, J 8.1 Hz), 7.20 (2H, d, J 8.4 Hz), 7.29 (2H, d, J 8.4 Hz), 7.68 (1H, d, J 1.9 Hz), 7.89 (1H, dd, J 8.1, 1.9 Hz), 8.22 (1H, t, J 6.2 Hz), 11.41 (1H, s).

2,3-Dioxo-2,3-dihydro-1H-indole-5-sulfonic acid benzylmethylamide (rpm128)

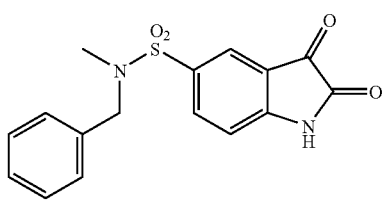 [SMILES: CN(Cc1ccccc1)S(=O)(=O)c1ccc2c(c1)C(=O)C(=O)N2]

This was obtained from rpm121 and N-methylbenzylamine in a similar manner as described for preparation of rpm123. The pure compound rpm128 was obtained after trituration with ethyl acetate as a yellow solid (47%), mp 170-172 ° C. $^1$H NMR (400 MHz, DMSO-d$_6$) δ 2.53 (3H, s), 4.13 (2H, s), 7.10 (1H, d, J 8.4 Hz), 7.25-7.37 (5H, m), 7.79 (1H, d, J 1.9 Hz), 8.01 (1H, dd, J 8.4, 1.9 Hz).

2,3-Dioxo-2,3-dihydro-1H-indole-5-sulfonic acid 3-methoxybenzylamide (rpm129)

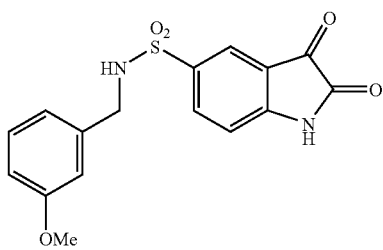 [SMILES: COc1cccc(CNS(=O)(=O)c2ccc3c(c2)C(=O)C(=O)N3)c1]

This was obtained from rpm121 and 3-methoxybenzylamine in a similar manner as described for preparation of rpm123. The pure compound rpm129 was obtained after trituration with ethyl acetate as a yellow (54%), mp 215-217° C. $^1$H NMR (400 MHz, DMSO-d$_6$) δ 3.65 (3H, s), 3.95 (2H, d, J 6.6 Hz), 6.72-6.77 (3H, m), 6.98 (1H, d, J 8.2 Hz), 7.11-715 (1H, m), 7.68 (1H, d, J 1.6 Hz), 7.89 (1H, dd, J 8.2, 1.6 Hz), 8.15 (1H, t, J 6.6 Hz), 11.39 (1H, s).

2,3-Dioxo-2,3-dihydro-1H-indole-5-sulfonic acid (thiophen-2-ylmethyl)amide (rpm130)

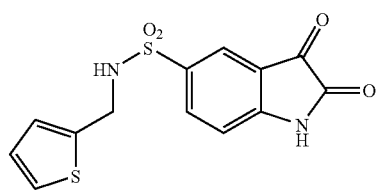 [SMILES: O=C1Nc2ccc(S(=O)(=O)NCc3cccs3)cc2C1=O]

This was obtained from rpm121 and 2-thiophenemethylamine in a similar manner as described for preparation of rpm123. The pure compound rpm130 was obtained after trituration with ethyl acetate as a yellow solid (49%), mp 180° C. (dec). $^1$H NMR (400 MHz, DMSO-d$_6$) δ 4.16 (2H, d, J 6.1 Hz), 6.86-6.88 (2H, m) 7.02 (1H, d, J 8.2 Hz), 7.37 (1H, dd, J 2.0, 4.4 Hz), 7.74 (1H, d, J 2.0 Hz), 7.92 (1H, dd, J 8.2, 2.0 Hz), 8.27 (1H, t, J 6.1 Hz), 11.40 (1H, s).

2,3-Dioxo-2,3-dihydro-1H-indole-5-sulfonic acid (2-dimethylamino-ethyl)amide (rpm131)

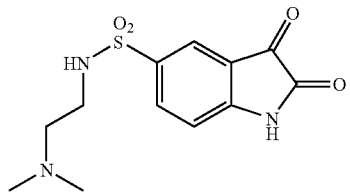 [SMILES: CN(C)CCNS(=O)(=O)c1ccc2c(c1)C(=O)C(=O)N2]

This was obtained from rpm121 and N,N-dimethylethylenediamine in a similar manner as described for preparation of rpm123. The crude product was used in the next step without further purification.

2,3-Dioxo-2,3-dihydro-1H-indole-5-sulfonic acid (2-dimethylamino-propyl)amide (HL1-096-13)

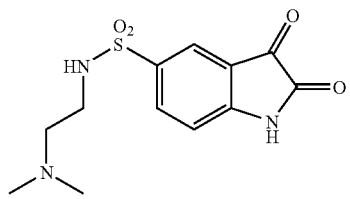 [SMILES: CN(C)CCNS(=O)(=O)c1ccc2c(c1)C(=O)C(=O)N2]

This was obtained from rpm121 and N,N-dimethylpropyldiamine in a similar manner as described for preparation of rpm123. The crude was used in the next step without further purification.

2,3-Dioxo-2,3-dihydro-1H-indole-5-sulfonic acid (pyridin-2-ylmethyl)amide (rpm133)

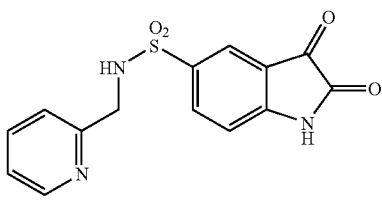 [SMILES: O=C1Nc2ccc(S(=O)(=O)NCc3ccccn3)cc2C1=O]

This was obtained from rpm121 and 2-(aminomethyl)pyridine in a similar manner as described for preparation of rpm123. The pure compound rpm133 was obtained after trituration with ethyl acetate as a yellow solid (58%), mp 140° C. (dec). $^1$H NMR (400 MHz, DMSO-$d_6$) δ 4.06 (2H, d, J 6.2 Hz), 6.99 (1H, d, J 8.4 Hz), 7.19-7.22 (1H, m), 7.32 (1H, d, J 7.7 Hz), 7.70 (1H, td, J 7.7, 1.7 Hz), 7.74 (1H, d, J 2.0 Hz), 7.91 (1H, dd, J 8.4, 2.0 Hz), 8.28 (1H, t, J 6.2 Hz), 8.39-8.40 (1H, m), 11.39 (1H, s).

2,3-Dioxo-2,3-dihydro-1H-indole-5-sulfonic acid (pyridin-4-ylmethyl)amide (rpm142)

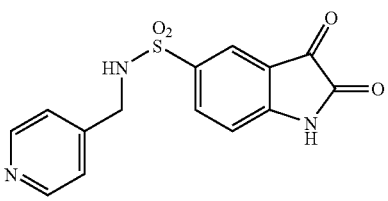 [SMILES: O=C1Nc2ccc(S(=O)(=O)NCc3ccncc3)cc2C1=O]

This was obtained from rpm121 and 4-(aminomethyl)pyridine in a similar manner as described for preparation of rpm123. The crude was used in the next step without further purification.

2,3-Dioxo-2,3-dihydro-1H-indole-5-sulfonic acid propylamide (rpm158)

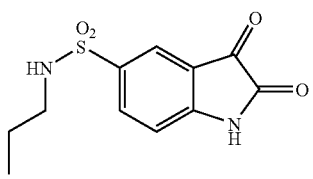 [SMILES: CCCNS(=O)(=O)c1ccc2c(c1)C(=O)C(=O)N2]

This was obtained as from rpm121 and propylamine in a similar manner as described for preparation of rpm123. The pure compound rpm158 was obtained after trituration with ethyl acetate as a yellow solid (45%), mp 242-244° C. $^1$H NMR (400 MHz, DMSO-$d_6$) δ 0.77 (3H, t, J 7.1 Hz), 1.39 (2H, sext, J 7.1 Hz), 2.65 (2H, q, J 7.1 Hz), 7.04 (1H, d, J 8.4 Hz), 7.58 (1H, t, J 6.0 Hz), 7.75 (1H, d, J 1.8 Hz), 7.92 (1H, dd, J 8.4, 1.8 Hz), 11.38 (1H, s).

2,3-Dioxo-2,3-dihydro-1H-indole-5-sulfonic acid isopropylamide (rpm159)

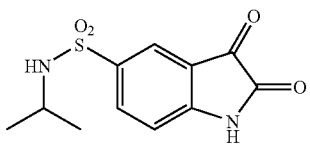 [SMILES: CC(C)NS(=O)(=O)c1ccc2c(c1)C(=O)C(=O)N2]

This was obtained from rpm121 and isopropylamine in a similar manner as described for preparation of rpm123. The pure compound rpm159 was obtained after trituration with ethyl acetate as a yellow solid (70%), mp 184-186° C. $^1$H NMR (400 MHz, DMSO-$d_6$) δ 0.94 (6H, d, J 6.8 Hz), 3.19 (1H, sept, J 6.8 Hz), 7.05 (1H, d, J 8.2 Hz), 7.58 (1H, d, J 6.8 Hz), 7.77 (1H, d, J 1.8 Hz), 7.94 (1H, dd, J 8.2, 1.8), 11.38 (1H, s).

2,3-Dioxo-2,3-dihydro-1H-indole-5-sulfonic acid (furan-2-ylmethyl)amide (rpm161)

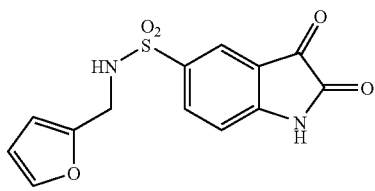 [SMILES: O=C1Nc2ccc(S(=O)(=O)NCc3ccco3)cc2C1=O]

This was obtained from rpm121 and furfurylamine in a similar manner as described for preparation of rpm123. The pure compound rpm161 was obtained after trituration with ethyl acetate ethyl acetate/hexane 3:2 as a yellow solid (95%), mp 120° C. (dec). $^1$H NMR (400 MHz, DMSO-$d_6$) δ 3.98 (2H, d, J 6.0 Hz), 6.17 (1H, d, J 3.2 Hz), 6.27 (1H, dd, J 1.6, 2.8 Hz), 6.99 (1H, d, J 8.4 Hz), 7.45 (1H, dd, J 0.8, 2.0 Hz), 7.71 (1H, d, J 2.0 Hz), 7.88 (1H, dd, J 1.8, 8.6 Hz), 8.18 (1H, t, J 6.0 Hz), 11.40 (1H, s).

2,3-Dioxo-2,3-dihydro-1H-indole-5-sulfonic acid (tetrahydrofuran-2-ylmethyl)amide (rpm166)

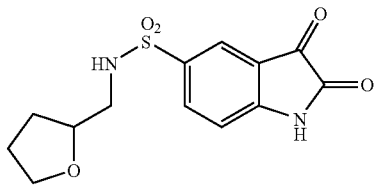 [SMILES: O=C1Nc2ccc(S(=O)(=O)NCC3CCCO3)cc2C1=O]

This was obtained from rpm121 and tetrahydrofurylamine in a similar manner as described for preparation of rpm123. The pure compound rpm166 was obtained after trituration with ethyl acetate ethyl acetate/hexane 3:2 as a yellow solid (66%), mp 180° C. (dec). $^1$H NMR (400 MHz, DMSO-d$_6$) δ 1.46-1.53 (1H, m), 1.69-1.85 (3H, m), 2.69-2.78 (2H, m), 3.51-3.67 (2H, m), 3.74-3.80 (1H, m), 7.07 (1H, d, J 8.4 Hz), 7.25 (1H, t, J 7.6 Hz), 7.48 (1H, d, J 6.8 Hz), 7.04 (1H, d, J 8.2 Hz), 7.74 (1H, t, J 6.2 Hz), 7.79 (1H, d, J 1.9 Hz), 7.93 (1H, dd, J 8.2, 1.9 Hz), 13.42 (1H, s).

2,3-Dioxo-2,3-dihydro-1H-indole-5-sulfonic acid (2-methoxy-ethyl)amide (rpm162)

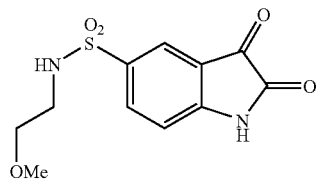 [SMILES: COCCNS(=O)(=O)c1ccc2c(c1)C(=O)C(=O)N2]

This was obtained from rpm121 and 2-methoxyethylamine in a similar manner as described for preparation of rpm123. The pure compound rpm162 was obtained after trituration with ethyl acetate:DCM (1:3, v/v) as a yellow solid (66%), mp 120° C. (dec). $^1$H NMR (400 MHz, DMSO-d$_6$) δ 2.87 (2H, q, J 5.6 Hz), 3.14 (3H, s), 3.28 (2H, t, J 5.8 Hz), 7.04 (1H, d, J 8.4 Hz), 7.75 (1H, t, J 6.0 Hz), 7.78 (1H, d, J 1.6 Hz), 7.93 (1H, dd, J 1.8, 8.2 Hz), 11.38 (1H, s).

2,3-Dioxo-2,3-dihydro-1H-indole-5-sulfonic acid sec-butylamide (rpm164).

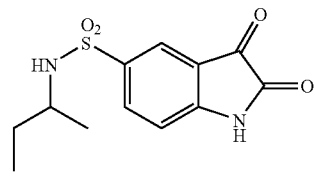 [SMILES: CCC(C)NS(=O)(=O)c1ccc2c(c1)C(=O)C(=O)N2]

This was obtained from rpm121 and sec-butylamine in a similar manner as described for preparation of rpm123. The pure compound rpm164 was obtained after trituration with ethyl acetate as a yellow solid (30%), mp 208-210° C. $^1$H NMR (400 MHz, DMSO-d$_6$): δ 0.71 (3H, t, J 7.6 Hz), 0.87 (3H, d, J 6.8 Hz), 1.29 (2H, quint, t, J 7.2 Hz), 3.01 (1H, quint, J 6.7 Hz), 7.03 (1H, d, J 8.4 Hz), 7.53 (1H, d, J 7.2 Hz), 7.75 (1H, s, H-4), 7.93 (1H, d, J 8.0 Hz), 11.36 (1H, s).

5-(Morpholine-4-sulfonyl)-1H-indole-2,3-dione[2] (rpm163)

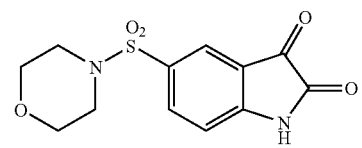 [SMILES: O=C1Nc2ccc(S(=O)(=O)N3CCOCC3)cc2C1=O]

A solution of rpm121 (0.211 g, 0.861 mmol) and morpholine (0.187 g, 2.139 mmol, 2.5 eq), in anhydrous DCM (7 ml) and anhydrous chloroform (1 ml) was stirred for 3 h at room temperature under Ar. The yellow precipitate was collected by filtration and dried under vacuum. The crude product was used in the next step without further purification.

1-Ethyl-2,3-dioxo-2,3-dihydro-1H-indole-5-sulfonic acid dimethylamide (rpm157)

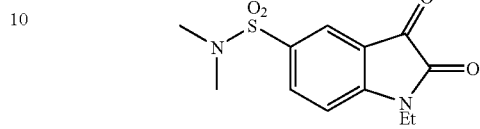

Ethyl bromide (2.51 mmol, 4 eq) was added to a solution of rpm123 (0.160 g, 0.629 mmol) and NaH (2.51 mmol, 4 eq) in anhydrous DMF (4 ml) at room temperature under Ar. After stirring overnight at room temperature under Ar, the reaction mixture was poured into water (10 ml). The mixture was extracted with ethyl acetate (3×10 ml), dried over Na$_2$SO$_4$ and the solvent was distilled off under reduced pressure. The compound was purified via chromatography on silica gel (hexanes/ethyl acetate 6:4) to give rpm157 as a red solid (0.094 g, 0.034 mmol, 52%), mp 165-167° C. $^1$H NMR (400 MHz, CDCl$_3$) δ 2.71 (3H, t, J 7.2 Hz), 2.74 (6H, s), 3.84 (2H, q, J 7.2 Hz), 7.06 (1H, d, J 8.0 Hz), 7.97 (1H, d, J 1.6 Hz), 8.02 (1H, dd, J 1.6, 8.0 Hz).

1-Methyl-2,3-dioxo-2,3-dihydro-1H-indole-5-sulfonic acid dimethylamide (rpm153)

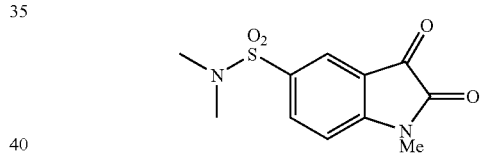

This was obtained from rpm123 and iodomethane in a similar manner as described for preparation of rpm157. The compound was purified via chromatography on silica gel (hexanes/ethyl acetate 7:3) to give rpm153 as a red solid (19%), mp 190-192° C. $^1$H NMR (400 MHz, CDCl$_3$) δ 2.74 (6H, s), 3.33 (3H, s), 7.08 (1H, d, J 8.2 Hz), 7.98 (1H, d, J 2.0 Hz), 8.05 (1H, dd, J 2.0, 8.2 Hz).

1-Benzyl-2,3-dioxo-2,3-dihydro-1H-indole-5-sulfonic acid dimethylamide (rpm155).

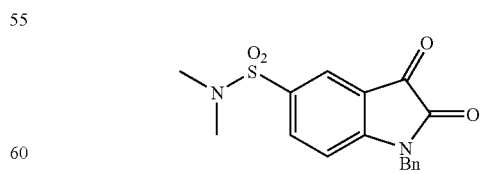

This was obtained from rpm123 and benzylbromide in a similar manner as described for preparation of rpm157. The compound was purified via chromatography on silica gel (hexanes/ethyl acetate 6:4) to give rpm153 as a red solid (41%), mp 152-154° C. $^1$H NMR (400 MHz, CDCl$_3$) δ 2.71

(6H, s), 4.98 (2H, s, CH$_2$), 6.94 (1H, d, J 8.0 Hz), 7.33-7.40 (5H, m), 7.91 (1H, dd, J 2.0, 8.0 Hz), 7.98 (1H, d, J 2.0 Hz).

3-[(2-Nitrophenyl)hydrazono]-2-oxo-2,3-dihydro-1H-indole-5-sulfonic acid dimethylamide (rpm124)

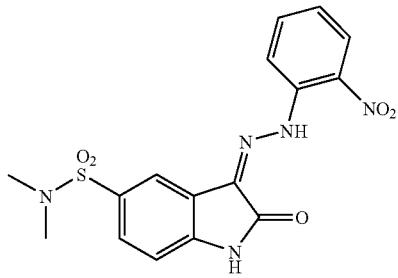 [SMILES: CN(C)S(=O)(=O)c1ccc2c(c1)/C(=N/Nc1ccccc1[N+](=O)[O-])C(=O)N2]

A solution of rpm123 (0.09 g, 0.354 mmol) and 2-nitrophenylhydrazine (0.059 g, 0.389 mmol, 1.1 eq) in ethanol (8 ml) was stirred for 4 h at 80° C. in presence of HCl (aq 4M, 4 drops). Pure compound was obtained by filtration and dried in vacuo (0.083 g, 0.213 mmol, 60%). MS (API-ES): m/z 390 (M+H)$^+$; HRMS (API-ES) m/z Found: 390.0871 (M+H)$^+$, 407.1139 (M+NH$_4$)$^+$.

3-[(2-Nitrophenyl)hydrazono]-2-oxo-2,3-dihydro-1H-indole-5-sulfonicamide (rpm134)

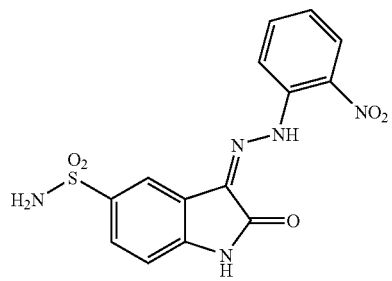 [SMILES: NS(=O)(=O)c1ccc2c(c1)/C(=N/Nc1ccccc1[N+](=O)[O-])C(=O)N2]

This was obtained as a yellow solid (58%) from rpm125 and 2-nitrophenylhydrazine in a similar manner as described for preparation of rpm124. mp>300° C. $^1$H NMR (400 MHz, DMSO-d$_6$) δ 7.03 (1H, d, J 8.4 Hz), 7.19-7.24 (1H, m), 7.30 (2H, s), 7.77 (1H, dd, J 2.0, 8.0 Hz), 7.81-785 (1H, m), 8.07 (1H, d, J 1.6 Hz), 8.21-824 (2H, m), 11.53 (1H, s), 14.24 (1H, s). MS (API-ES): m/z 362 [M+H]$^+$, 379 (M+NH$_4$)$^+$; HRMS (API-ES) m/z Found: 379.0818 (M+NH$_4$)$^+$.

3-[(2-Nitrophenyl)hydrazono]-2-oxo-2,3-dihydro-1H-indole-5-sulfonic acid (pyridin-2-ylmethyl)amide (rpm135)

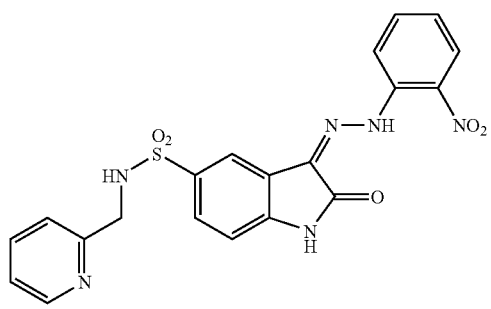 [SMILES: O=C1Nc2ccc(S(=O)(=O)NCc3ccccn3)cc2/C1=N/Nc1ccccc1[N+](=O)[O-]]

This was obtained as a yellow solid (58%) from rpm133 and 2-nitrophenylhydrazine in a similar manner as described for preparation of rpm124. MS (API-ES): r/z 453 (M+H)$^+$, 475 (M+Na)$^+$; HRMS (API-ES) m/z Found: 453.0980 (M+H)$^+$.

3-[(2-Nitrophenyl)hydrazono]-2-oxo-2,3-dihydro-1H-indole-5-sulfonic acid benzyl-methylamide (rpm136)

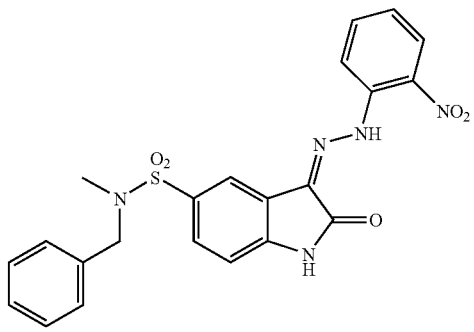 [SMILES: CN(Cc1ccccc1)S(=O)(=O)c1ccc2c(c1)/C(=N/Nc1ccccc1[N+](=O)[O-])C(=O)N2]

This was obtained as a yellow solid (54%) from rpm128 and 2-nitrophenylhydrazine in a similar manner as described for preparation of rpm124. MS (API-ES): m/z 466 (M+H)$^+$, 488 (M+Na)$^+$, HRMS (API-ES) m/z Found: 466.1180 (M+H)$^+$.

3-[(2-Nitrophenyl)hydrazono]-2-oxo-2,3-dihydro-1H-indole-5-sulfonic acid 3-methoxybenzylamide (rpm137)

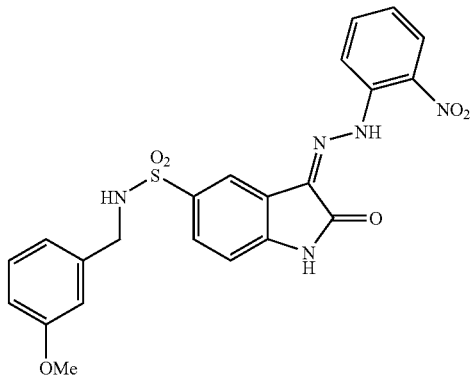 [SMILES: COc1cccc(CNS(=O)(=O)c2ccc3c(c2)/C(=N/Nc2ccccc2[N+](=O)[O-])C(=O)N3)c1]

This was obtained as a yellow solid (45%) from rpm129 and 2-nitrophenylhydrazine in a similar manner as described for preparation of rpm124. MS (API-ES): m/z 481.2 [M+H]$^+$, 499 (M+NH$_4$)$^+$, 504 (M+Na)$^+$; HRMS (API-ES) m/z Found: 499.1392 (M+NH$_4$)$^+$.

3-[(2-Nitrophenyl)hydrazono]-2-oxo-2,3-dihydro-1H-indole-5-sulfonic acid 4-methoxybenzylamide (rpm138)

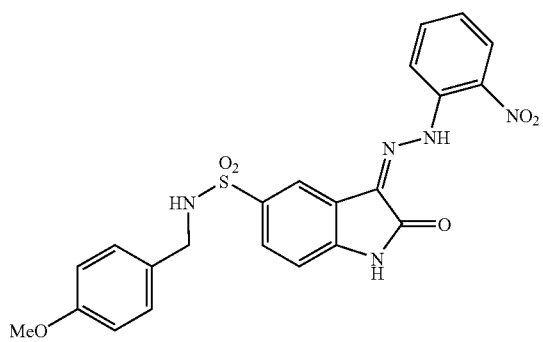 [SMILES: COc1ccc(CNS(=O)(=O)c2ccc3c(c2)/C(=N/Nc2ccccc2[N+](=O)[O-])C(=O)N3)cc1]

This was obtained as a yellow solid (57%) from rpm126 and 2-nitrophenylhydrazine in a similar manner as described for preparation of rpm124. MS (API-ES): m/z 499 [M+NH$_4$]$^+$, 504 (M+Na)$^+$; HRMS (API-ES) m/z Found: 499.1387 (M+NH$_4$)$^+$.

3-[(2-Nitrophenyl)hydrazono]-2-oxo-2,3-dihydro-1H-indole-5-sulfonic acid 4-chlorobenzylamide (rpm139).

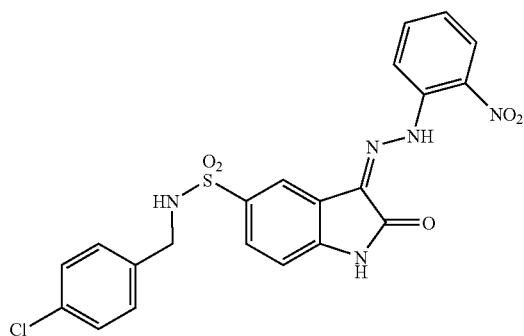 [SMILES: O=C1Nc2ccc(S(=O)(=O)NCc3ccc(Cl)cc3)cc2/C1=N/Nc1ccccc1[N+](=O)[O-]]

This was obtained as a yellow solid (43%) from rpm127 and 2-nitrophenylhydrazine in a similar manner as described for preparation of rpm124, mp>300° C. $^1$H NMR (400 MHz, DMSO-d$_6$) δ 3.98 (2H, d, J 6.4 Hz), 7.06 (1H, d, J 8.0 Hz), 7.23-7.27 (5H, m), 7.70 (1H, dd, J 1.8, 8.2 Hz), 7.82 (1H, t, J 8.4 Hz), 7.90 (1H, d, J 1.6 Hz), 8.13 (1H, t, J 6.4 Hz), 8.23 (2H, m), 11.56 (1H, s), 14.23 (1H, s). MS (API-ES): m/z 486 [M+H]$^+$, 504 (M+NH4)$^+$, 508 (M+Na)$^+$; HRMS (API-ES) m/z Found: 503.0894 (M+NH$_4$)$^+$; 486.0626 (M+H)$^+$.

3-[(2-Nitrophenyl)hydrazono]-2-oxo-2,3-dihydro-1H-indole-5-sulfonic acid (thiophen-2-ylmethyl)amide (rpm140).

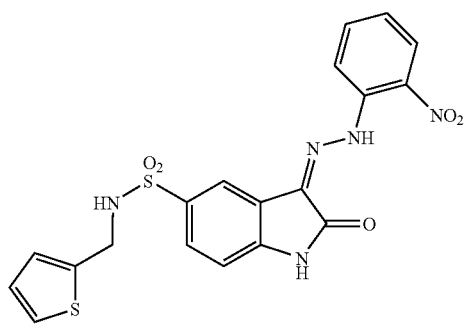 [SMILES: O=C1Nc2ccc(S(=O)(=O)NCc3cccs3)cc2/C1=N/Nc1ccccc1[N+](=O)[O-]]

This was obtained as a yellow solid (59%) from rpm130 and 2-nitrophenylhydrazine in a similar manner as described for preparation of rpm124. MS (API-ES): m/z 475 [M+NH$_4$]$^+$, 480 (M+Na)$^+$; HRMS (API-ES) m/z Found: 475.0852 (M+NH$_4$)$^+$.

3-[(2-Nitrophenyl)hydrazono]-2-oxo-2,3-dihydro-1H-indole-5-sulfonic acid (pyridin-4-ylmethyl)amide (rpm145)

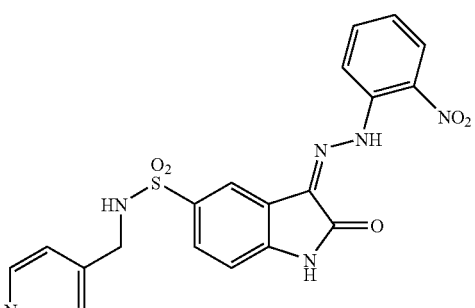

This was obtained as a yellow solid (38%) from rpm142 and 2-nitrophenylhydrazine in a similar manner as described for preparation of rpm124. MS (API-ES): m/z 453 (M+H)$^+$; HRMS (API-ES) m/z Found: 453.0978 (M+H)$^+$–.

3-[(2-Nitrophenyl)hydrazono]-2-oxo-2,3-dihydro-1H-indole-5-sulfonic acid (2-dimethylaminoethyl)amide (rpm146)

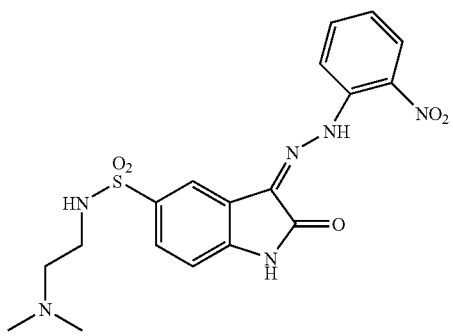 [SMILES: CN(C)CCNS(=O)(=O)c1ccc2c(c1)/C(=N/Nc1ccccc1[N+](=O)[O-])C(=O)N2]

This was obtained as a yellow solid (24%) from rpm131 and 2-nitrophenylhydrazine in a similar manner as described for preparation of rpm124. MS (API-ES): m/z 433 (M+H)$^+$; HRMS (API-ES) m/z Found: 433.1293 (M+H)$^+$.

1-Methyl-3-[(2-nitro-phenyl)-hydrazono]-2-oxo-2,3-dihydro-1H-indole-5-sulfonic acid dimethylamide (rpm154)

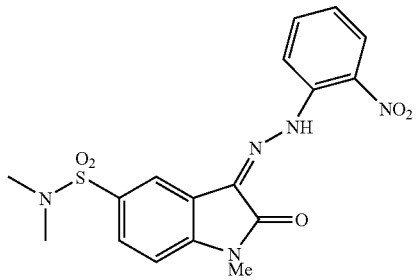 [SMILES: CN1C(=O)/C(=N\Nc2ccccc2[N+](=O)[O-])c2cc(S(=O)(=O)N(C)C)ccc21]

This was obtained as a yellow solid (36%) from rpm153 and 2-nitrophenylhydrazine in a similar manner as described for preparation of rpm124. MS (API-ES): m/z 404 [M+H]$^+$; HRMS (API-ES) m/z Found: 404.1018 (M+H)$^+$.

HL1-047. This was obtained as a yellow solid from isatin and 2-nitrophenylhydrazine in a similar manner as described for preparation of rpm124

HL1-050-1. This was obtained as a yellow solid from isatin and 2-chlorophenylhydrazine in a similar manner as described for preparation of rpm124

HL1-050-2. This was obtained as a yellow solid from isatin and 3-nitrophenylhydrazine in a similar manner as described for preparation of rpm124

HL1-056 (NSC117199). This was obtained as a yellow solid from isatin-5-sulfonic acid and 2-nitrophenylhydrazine in a similar manner as described for preparation of rpm124. HL2-056 (NSC117199): $^1$H NMR (DMSO-d$_6$, 400 MHz) δ 11.22 (s, 1H), 8.23-8.18 (m, 2H), 7.83 (s, 1H), 7.77 (t, 1H), 7.57-7.55 (dd, J=7.6 Hz, 1.2 Hz, 1H), 7.17-7.13 (m, 1H), 6.87 (d, J=8.0 Hz, 1H)

HL1-058-1. This was obtained as a yellow solid from isatin-5-sulfonic acid and 2-chlorophenylhydrazine in a similar manner as described for preparation of rpm124

3-[(2-Nitrophenyl)hydrazono]-2-oxo-2,3-dihydro-1H-indole-5-sulfonic acid (furan-2-ylmethyl)amide (rpm168)

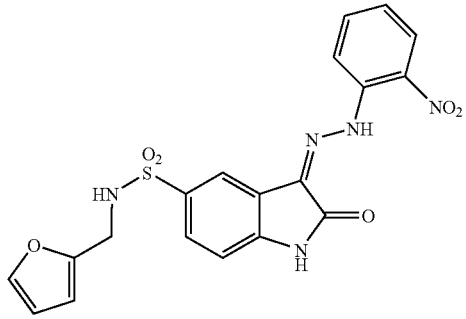 [SMILES: O=C1Nc2ccc(S(=O)(=O)NCc3ccco3)cc2/C1=N/Nc1ccccc1[N+](=O)[O-]]

A mixture of rpm161 (0.040 g, 0.114 mmol) 2-nitrophenylhydrazine (0.021 g, 0.126 mmol, 1.1 eq) and HCl (aq 4 M, 2 drops) in ethanol (3 mL) was heated in the CEM microwave at 120° C. for 15 min. After cooling to room temperature, pure product rpm168 was collected as an orange precipitate by filtration and dried in vacuo. The pure compound rpm168 was obtained without further purification (0.048 g, 0.099 mmol, 86%). MS (API-ES): m/z 459 (M+NH$_4$)$^+$; HRMS (API-ES) m/z Found: 459.1082 (M+NH$_4$)$^+$.

HL2-016-11. This was obtained as a yellow solid from rpm161 and 2-chlorophenylhydrazine in a similar manner as described for preparation of rpm168.

3-[(2-Nitrophenyl)hydrazono]-2-oxo-2,3-dihydro-1H-indole-5-sulfonic acid isopropylamide (rpm169)

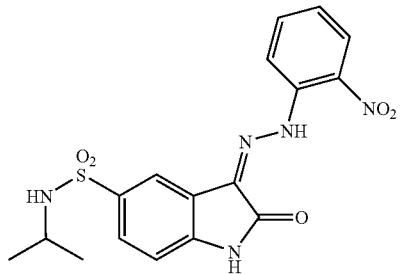 [SMILES: CC(C)NS(=O)(=O)c1ccc2c(c1)/C(=N/Nc1ccccc1[N+](=O)[O-])C(=O)N2]

This was obtained as a yellow solid (50%) from rpm159 and 2-nitrophenylhydrazine in a similar manner as described for preparation of rpm168. MS (API-ES): m/z 421 (M+NH$_4$)$^+$ (100%), 404 (M+H)$^+$(80%); HRMS (API-ES) m/z Found: 421.1285 (M+NH$_4$)$^+$; 404.1016 (M+H)$^+$.

3-[(2-Nitrophenyl)-hydrazono]-2-oxo-2,3-dihydro-1H-indole-5-sulfonic acid propylamide (rpm170)

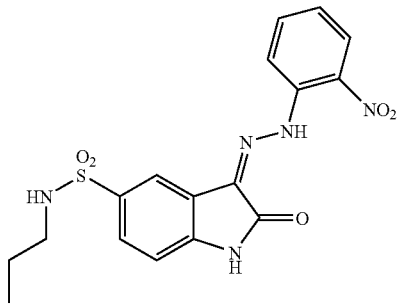 [SMILES: CCCNS(=O)(=O)c1ccc2c(c1)/C(=N/Nc1ccccc1[N+](=O)[O-])C(=O)N2]

This was obtained as a yellow solid (56%) from rpm158 and 2-nitrophenylhydrazine in a similar manner as described for preparation of rpm168. MS (API-ES): m/z 421 (M+NH$_4$)$^+$ (100%), 404 (M+H)$^+$(60%); HRMS (API-ES) m/z Found: 421.1287 (M+NH$_4$)$^+$; 404.1014 (M+H)$^+$.

HL2-016-9. This was obtained as a yellow solid from rpm158 and 2-chlorophenylhydrazine in a similar manner as described for preparation of rpm168.

3-[(2-Nitrophenyl)hydrazono]-2-oxo-2,3-dihydro-1H-indole-5-sulfonic acid (2-methoxyethyl)amide (rpm171)

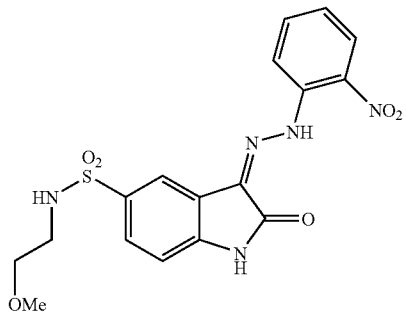 [SMILES: COCCNS(=O)(=O)c1ccc2c(c1)/C(=N/Nc1ccccc1[N+](=O)[O-])C(=O)N2]

This was obtained as a yellow solid (49%) from rpm162 and 2-nitrophenylhydrazine in a similar manner as described for preparation of rpm168. MS (API-ES): m/z 420 (M+H)$^+$ (100%); 437 (M+NH$_4$)$^+$(40%), HRMS (API-ES) m/z Found: 437.1243 (M+NH$_4$)$^+$; 420.0979 (M+H)$^+$.

HL2-016-12. This was obtained as a yellow solid from rpm162 and 2-chlorophenylhydrazine in a similar manner as described for preparation of rpm168.

3-[(2-Nitrophenyl)hydrazono]-2-oxo-2,3-dihydro-1H-indole-5-sulfonic acid (tetrahydrofuran-2-ylmethyl)amide (rpm172)

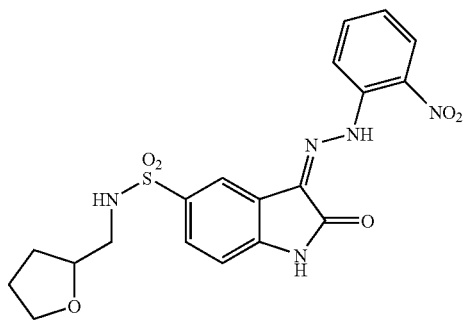 [SMILES: O=C1Nc2ccc(S(=O)(=O)NCC3CCCO3)cc2/C1=N/Nc1ccccc1[N+](=O)[O-]]

This was obtained as a yellow solid (63%) yield from rpm166 and 2-nitrophenylhydrazine in a similar manner as described for preparation of rpm168. MS (API-ES): m/z 446 (M+H)$^+$, HRMS (API-ES) m/z Found: 463.1398 (M+NH$_4$)$^+$; 446.1138(M+H)$^+$.

HL2-016-14. This was obtained as a yellow solid from rpm166 and 2-chlorophenylhydrazine in a similar manner as described for preparation of rpm168.

3-[(2-Nitrophenyl)hydrazono]-2-oxo-2,3-dihydro-1H-indole-5-sulfonic acid sec-butylamide (rpm173)

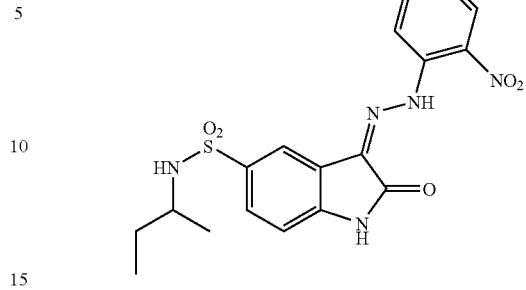

This was obtained as a yellow solid (50%) from rpm164 and 2-nitrophenylhydrazine in a similar manner as described for preparation of rpm168. MS (API-ES): m/z 418 (M+H)$^+$ (100%); 435 (M+NH$_4$)$^+$(60%); HRMS (API-ES) m/z Found: 435.1448 (M+NH$_4$)$^+$; 418.1181 (M+H)$^+$.

HL2-016-13. This was obtained as a yellow solid from rpm123 and 2-chlorophenylhydrazine in a similar manner as described for preparation of rpm168.

1-Ethyl-3-[(2-nitro-phenyl)-hydrazono]-2-oxo-2,3-dihydro-1H-indole-5-sulfonic acid dimethylamide (rpm176)

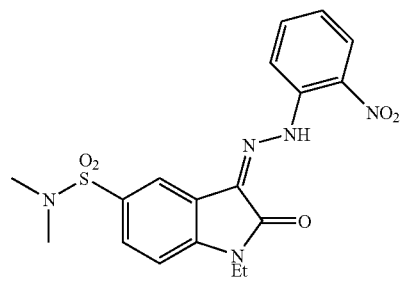

This was obtained as a yellow solid (62%) from rpm and 2-nitrophenylhydrazine in a similar manner as described for preparation of rpm168. MS (API-ES): m/z 418 (M+H)$^+$; HRMS (API-ES) m/z Found: 435.1448 (M+NH$_4$)$^+$; 418.1180 (M+H)$^+$.

5-(Morpholine-4-sulfonyl)-3-[(2-nitrophenyl)hydrazonol-1,3-dihydro-indol-2-one (rpm177)

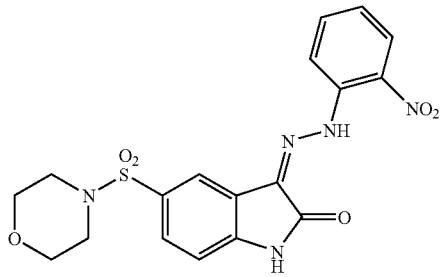 [SMILES: O=C1Nc2ccc(S(=O)(=O)N3CCOCC3)cc2/C1=N/Nc1ccccc1[N+](=O)[O-]]

This was obtained as a yellow solid (56%) yield from rpm163 and 2-nitrophenylhydrazine in a similar manner as described for preparation of rpm168. MS (API-ES): m/z 432

(M+H)⁺, 449 (M+NH₄)⁺; HRMS (API-ES) m/z Found: 449.1240 (M+NH₄)⁺; 432.0974 (M+H)⁺.

HL2-016-8. This was obtained as a yellow solid from rpm163 and 2-chlorophenylhydrazine in a similar manner as described for preparation of rpm168. HL2-016-8: ¹H NMR (DMSO-d₆, 400 MHz) δ 13.10 (s, 1H), 11.64 (s, 1H), 7.91 (d, J=8.4 Hz, 1H), 7.86 (s, 1H), 7.64 (d, J=8.4 Hz, 1H), 7.51 (d, J=8.4 Hz, 1H), 7.42 (appt, 1H), 7.16 (d, J=8.4 Hz, 1H), 7.09 (appt, 1 H), 3.62 (broad s, 4H), 2.86 (broad s, 2H).

1-Benzyl-3-[(2-nitro-phenyl)-hydrazonol-2-oxo-2,3-dihydro-1H-indole-5-sulfonic acid dimethylamide (rpm156).

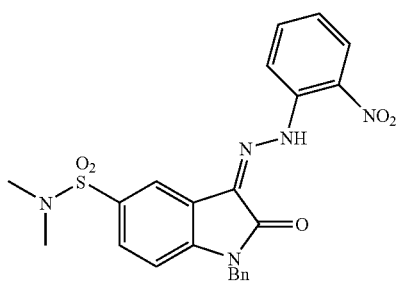

This was obtained as a yellow solid (21%) from rpm and 2-nitrophenylhydrazine in a similar manner as described for preparation of rpm168. MS (API-ES): m/z 480 (M+H)⁺; HRMS (API-ES) m/z Found: 480.1289 (M+H)⁺.

HL2-016-1. This was obtained as a yellow solid from rpm123 and 2-chlorophenylhydrazine in a similar manner as described for preparation of rpm168.

HL2-016-2. This was obtained as a yellow solid from rpm125 and 2-chlorophenylhydrazine in a similar manner as described for preparation of rpm168.

HL2-016-7. This was obtained as a yellow solid from rpm133 and 2-chlorophenylhydrazine in a similar manner as described for preparation of rpm168.

HL2-016-16. This was obtained as a yellow solid from rpm128 and 2-chlorophenylhydrazine in a similar manner as described for preparation of rpm168.

HL2-016-5. This was obtained as a yellow solid from rpm129 and 2-chlorophenylhydrazine in a similar manner as described for preparation of rpm168.

HL2-016-3. This was obtained as a yellow solid from rpm126 and 2-chlorophenylhydrazine in a similar manner as described for preparation of rpm168.

HL2-016-4. This was obtained as a yellow solid from rpm127 and 2-chlorophenylhydrazine in a similar manner as described for preparation of rpm168.

HL2-016-6. This was obtained as a yellow solid from rpm140 and 2-chlorophenylhydrazine in a similar manner as described for preparation of rpm168.

HL2-016-15. This was obtained as a yellow solid from rpm142 and 2-chlorophenylhydrazine in a similar manner as described for preparation of rpm168.

HL2-016-19. This was obtained as a yellow solid from rpm131 and 2-chlorophenylhydrazine in a similar manner as described for preparation of rpm168.

HL2-016-10. This was obtained as a yellow solid from rpm159 and 2-chlorophenylhydrazine in a similar manner as described for preparation of rpm168. L2-016-10: ¹H NMR (400 MHz, DMSO-d₆) δ 13.07 (s, 1H), 11.54 (s, 1H), 7.96 (s, 1H), 7.84 (d, J=8.0 Hz, 1H), 7.71 (d, J=7.20 Hz, 1H), 7.49-7.41 (m, 3H), 7.09 (d, J=7.60 Hz, 1H), 0.94 and 0.92 (2×s, 3H each), the (CH₃)₂CH signal is overlapped with H₂O.

HL2-016-18. This was obtained as a yellow solid from rpm142 and 2-chlorophenylhydrazine in a similar manner as described for preparation of rpm168.

HL2-016-20. This was obtained as a yellow solid from rpm142 and 2-nitrophenylhydrazine in a similar manner as described for preparation of rpm168.

HL2-016-21. This was obtained as a yellow solid from HL1-096-13 and 2-nitrohenylhydrazine in a similar manner as described for preparation of rpm168.

HL2-016-22. This was obtained as a yellow solid from HL1-096-13 and 2-chlorophenylhydrazine in a similar manner as described for preparation of rpm168.

2-[N'-(5-Isopropylsulfamoyl-2-oxo-1,2-dihydro-indol-3-ylidene)-hydrazino]benzoic acid (rpm186)

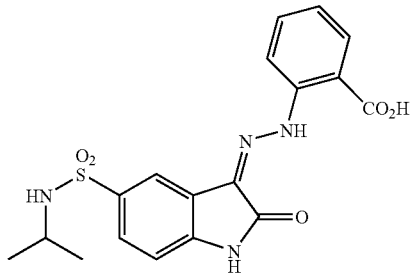 [SMILES: CC(C)NS(=O)(=O)c1ccc2c(c1)/C(=N/Nc1ccccc1C(=O)O)C(=O)N2]

This was obtained as a yellow solid (68%) from rpm159 and 2-carboxylphenylhydrazine in a similar manner as described for preparation of rpm168. MS (API-ES): m/z 403 [M+H]⁺; HRMS (API-ES) m/z Found: 403.1066 (M+H)⁺.

2-[N'-(2-Oxo-5-sulfamoyl-1,2-dihydro-indol-3-ylidene)hydrazino]benzoic acid (rpm188)

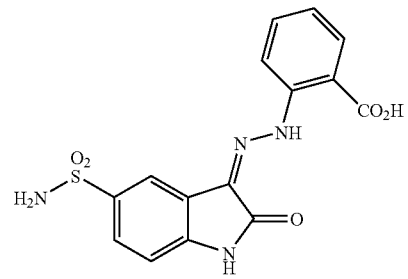 [SMILES: NS(=O)(=O)c1ccc2c(c1)/C(=N/Nc1ccccc1C(=O)O)C(=O)N2]

This was obtained as a yellow solid (30%) from rpm125 and 2-carboxylphenylhydrazine in a similar manner as described for preparation of rpm168. MS (API-ES): m/z 359 [M−H]⁻; HRMS (API-ES) m/z Found: 359.0452 (M−H)⁻

2-[N'-[5-(4-Chloro-benzylsulfamoyl)-2-oxo-1,2-dihydro-indol-3-ylidene]hydrazino}benzoic acid (rpm191)

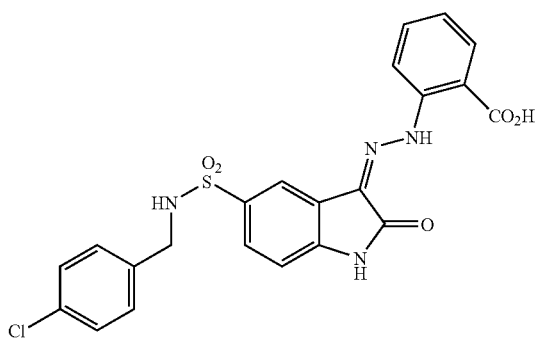 [SMILES: O=C1Nc2ccc(S(=O)(=O)NCc3ccc(Cl)cc3)cc2/C1=N/Nc1ccccc1C(=O)O]

This was obtained as a yellow solid (66%) from rpm127 and 2-carboxylphenylhydrazine in a similar manner as described for preparation of rpm168. MS (API-ES): m/z 483.1 (M$^{35}$Cl—H)$^-$(100%), 486 (M $^{37}$Cl—H)$^-$(70%); HRMS (API-ES) m/z Found: 483.0517 (M–H)$^-$.

3-(Phenylhydrazono)-2-oxo-2,3-dihydro-1H-indole-5-sulfonic acid isopropylamide (rpm275)

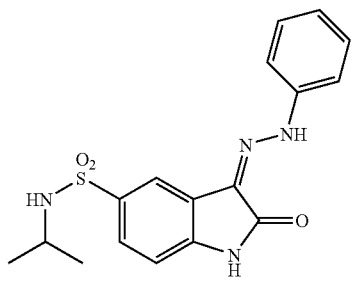 [SMILES: CC(C)NS(=O)(=O)c1ccc2c(c1)/C(=N/Nc1ccccc1)C(=O)N2]

This was obtained as a yellow solid (48%) from rpm159 and phenylhydrazine in a similar manner as described for preparation of rpm168. MS (API-ES): m/z 359 (M+H$^+$; HRMS (API-ES) m/z Found: 359.1169 (M+H)$^{+.}$

3-[N'-(5-Isopropylsulfamoyl-2-oxo-1,2-dihydro-indol-3-ylidene)hydrazino]benzoic acid (rpm297)

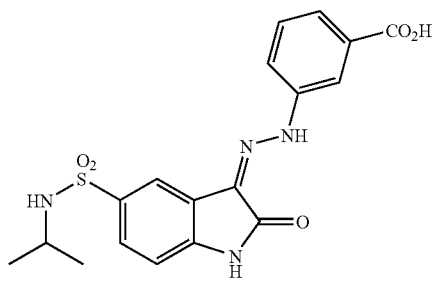

This was obtained as a yellow solid (57%) from rpm159 and 3-carboxylphenylhydrazine in a similar manner as described for preparation of rpm168. mp 275° C. (dec). $^1$H NMR (400 MHz, DMSO-d$_6$) δ 0.93 (6H, d, J 6.8 Hz), 3.21 (1H, sept, J 6.8 Hz), 7.05 (1H, d, J 8.4 Hz), 7.47-7.51 (2H, m, J 7.6 Hz), 7.45 (1H, d, J 8.0 Hz), 7.67-7.70 (3H, m), 7.92 (1H, d, J 2.0 Hz), 8.05-8.06 (1H, m), 11.43 (1H, s), 12.76 (1H, s). MS (API-ES): m/z 403 (M+H)$^+$; HRMS (API-ES) m/z Found: 403.1095 (M+H)$^+$.

2-['-(5-Isopropylsulfamoyl-2-oxo-1,2-dihydro-indol-3-ylidene)hydrazino]benzoic acid pentafluorophenyl ester[3] (rpm278)

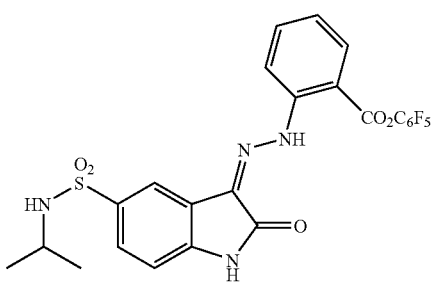

Anhydrous pyridine (0.362 g, 4.59 mmol, 1.5 eq) and pentafluorophenyltrifluoro acetate (1.28 g, 4.59 mmol, 1.5 eq) were added to a solution of rpm186 (1.23 g, 3.06 mmol) in anhydrous in DMF (15 ml) at room temperature under Ar. The reaction mixture was stirred for 1 h at room temperature. PFPTFA (0.325 g, 1.16 mmol) and anhydrous pyridine (0.204 g, 2.58 mmol) were added. The reaction mixture was stirred for 30 min and poured into water (20 ml). The product was extracted with ethyl acetate (3×40 ml), dried over Na$_2$SO$_4$ and the solvent removed under reduced pressure to provide a yellow solid. The pure compound rpm278 was obtained after trituration with a solution ethyl acetate/hexane (3:7, 40 ml) as a yellow solid (1.40 g, 3.38 mmol, 78%), mp 190-192° C. $^1$H NMR (400 MHz, DMSO-d$_6$) δ 0.93 (6H, d, J 6.8 Hz), 3.19-3.24 (1H, m), 7.07 (1H, d, J 8.4 Hz), 7.25 (1H, t, J 7.6 Hz), 7.48 (1H, d, J 6.8 Hz), 7.72 (1H, d, J 8.4 Hz), 7.86 (1H, t, J 7.6 Hz), 8.00 (1H, s), 8.18 (1H, d, J 8.4 Hz), 8.23 (1H, d, J 7.6 Hz), 11.44 (1H, s), 13.97 (1H, s).

3-[N'-(5-Isopropylsulfamoyl-2-oxo-1,2-dihydro-indol-3-ylidene)hydrazino]benzoic acid pentafluorophenyl ester (rpm323)

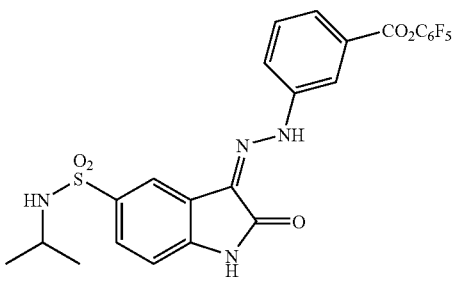

This was obtained as a yellow solid (80%) from rpm297 and pentafluorophenyltrifluoro acetate in a similar manner as described for preparation of rpm278. $^1$H NMR (400 MHz, DMSO-d$_6$) 0.93 (6H, d, J 6.4 Hz), 3.16-3.21 (1H, m), 7.07

(1H, d, J 8.0 Hz), 7.47 (1H, t, J 6.8 Hz), 7.63-7.70 (2H, m), 7.85 (1H, d, J 8.0 Hz), 7.93-7.97 (2H, m), 8.29 (1H, s)11.45 (1H, s), 12.81 (1H, s).

N-Furan-2-ylmethyl-2-[N'-(5-isopropylsulfamoyl-2-oxo-1,2-dihydro-indol-3-ylidene)hydrazino]benzamide[3] (rpm292)

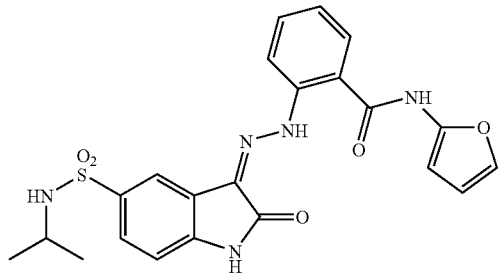 [SMILES: CC(C)NS(=O)(=O)c1ccc2c(c1)/C(=N/Nc1ccccc1C(=O)Nc1ccco1)C(=O)N2]

Anhydrous pyridine (0.030 g, 0.379 mmol, 1.5 eq) and furfurylamine (0.038 g, 0.390 mmol, 1.5 eq) were added to a solution of rpm278 (0.155 g, 0.264 mmol) anhydrous in acetonitrile (20 ml) at room temperature under Ar. The reaction mixture was stirred overnight at room temperature. The solvent was removed under reduced pressure to provide a yellow solid. The pure compound rpm292 was obtained after trituration with acetone (7 ml) as a brown solid (0.060 g, 0.125 mmol, 47%). MS (API-ES): m/z 482 (M+H)$^+$; HRMS (API-ES) m/z Found: 482.1489 (M+H)$^+$.

2-[N'-(5-Isopropylsulfamoyl-2-oxo-1,2-dihydro-indol-3-ylidene)hydrazino]benzamide (rpm283)

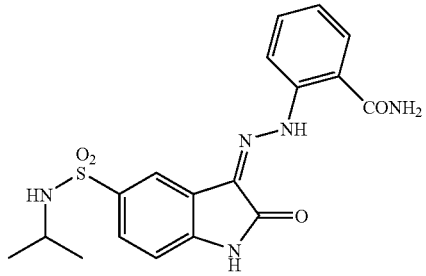 [SMILES: CC(C)NS(=O)(=O)c1ccc2c(c1)/C(=N/Nc1ccccc1C(N)=O)C(=O)N2]

This was obtained as a yellow solid (38%) yield from rpm278 and ammonia (2M solution in ethanol) in a similar manner as described for preparation of rpm292. MS (API-ES): m/z 402 (M+H)$^+$, m/z 385 (M—NH$_2$)$^+$; HRMS (API-ES) m/z Found: 402.1227 (M+H)$^+$.

N-(2-Dimethylaminoethyl)-2-[N'-(5-isopropylsulfamoyl-2-oxo-1,2-dihydro-indol-3-ylidene)hydrazino]benzamide (rpm284)

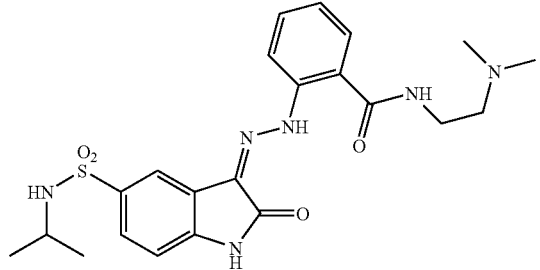 [SMILES: CC(C)NS(=O)(=O)c1ccc2c(c1)/C(=N/Nc1ccccc1C(=O)NCCN(C)C)C(=O)N2]

This was obtained as a yellow solid (37%) yield from rpm278 and N,N-dimethylethylenediamine in a similar manner as described for preparation of rpm292. MS (API-ES): m/z 473.1 (M+H)$^+$; HRMS (API-ES) m/z Found: 473.1975 (M+H)$^+$.

2-[N'-(5-Isopropylsulfamoyl-2-oxo-1,2-dihydro-indol-3-ylidene)-hydrazino]-N-(2-methoxyethyl)benzamide (rpm285)

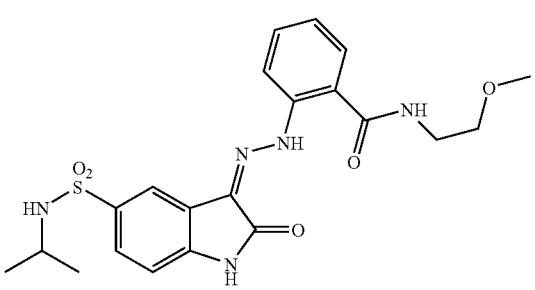 [SMILES: COCCNC(=O)c1ccccc1N/N=C1\C(=O)Nc2ccc(S(=O)(=O)NC(C)C)cc21]

This was obtained as a yellow solid (49%) yield from rpm278 and 2-methoxyethylamine in a similar manner as described for preparation of rpm292. MS (API-ES): m/z 460 (M+H)$^+$; HRMS (API-ES) m/z Found: 460.1652 (M+H)$^+$.

N-Benzyl-2-[N'-(5-isopropylsulfamoyl-2-oxo-1,2-dihydro-indol-3-ylidene)hydrazino]benzamide (rpm287)

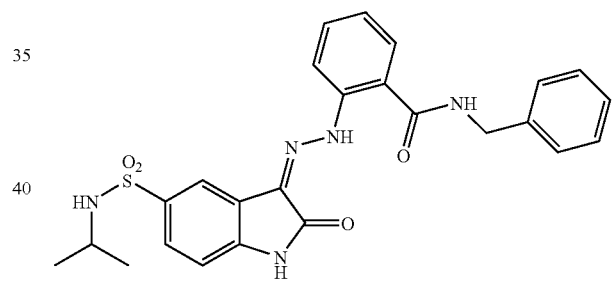

This was obtained as a yellow solid (84%) yield from rpm278 and benzylamine in a similar manner as described for preparation of rpm292. MS (API-ES): m/z 492 (M+H)$^+$; HRMS (API-ES) m/z Found: 492.1698 (M+H)$^+$.

2-[N'-(5-Isopropylsulfamoyl-2-oxo-1,2-dihydro-indol-3-ylidene)hydrazino]-N-pyridin-3-ylmethyl-benzamide (rpm290)

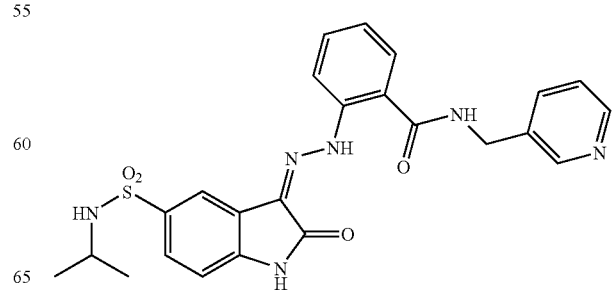

This was obtained as a yellow solid (37%) yield from rpm278 and 3-(aminomethyl)pyridine in a similar manner as described for preparation of rpm292. MS (API-ES): m/z 493 (M+H)⁺; HRMS (API-ES) m/z Found: 493.1649 (M+H)⁺.

2-[N'-(5-Isopropylsulfamoyl-2-oxo-1,2-dihydro-indol-3-ylidene)hydrazino]-N-(2-morpholin-4-yl-ethyl)benzamide (rpm293)

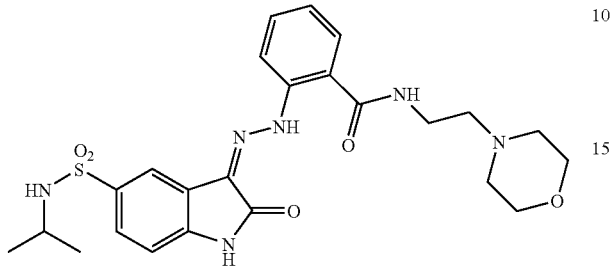

This was obtained as a yellow solid (67%) yield from rpm278 and 2-morpholin-4-yl-ethylamine in a similar manner as described for preparation of rpm292. MS (API-ES): m/z 515 (M+H)⁺; HRMS (API-ES) m/z Found: 515.2070 (M+H)⁺.

2-[N'-(5-Isopropylsulfamoyl-2-oxo-1,2-dihydro-indol-3-ylidene)hydrazino]-N,N-dimethylbenzamide (rpm294)

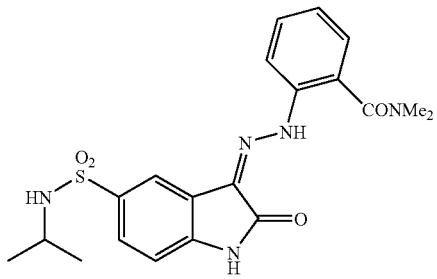

This was obtained as a yellow solid (43%) yield from rpm278 and dimethylamine (2M solution in THF) in a similar manner as described for preparation of rpm292. MS (API-ES): m/z 430 (M+H)⁺; HRMS (API-ES) m/z Found: 430.1540 (M+H)⁺.

2-[N'-(5-Isopropylsulfamoyl-2-oxo-1,2-dihydro-indol-3-ylidene)hydrazino]-N-methylbenzamide (rpm295)

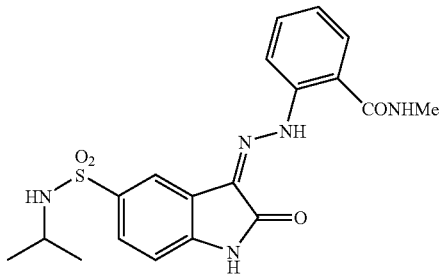

This was obtained as a yellow solid (69%) yield from rpm278 and methylamine (40% solution in water) in a similar manner as described for preparation of rpm292. MS (API-ES): m/z 416 (M+H)⁺; HRMS (API-ES) m/z Found: 416.1385 (M+H)⁺.

N-Ethyl-2-[N'-(5-isopropylsulfamoyl-2-oxo-1,2-dihydro-indol-3-ylidene)hydrazino]benzamide (rpm296)

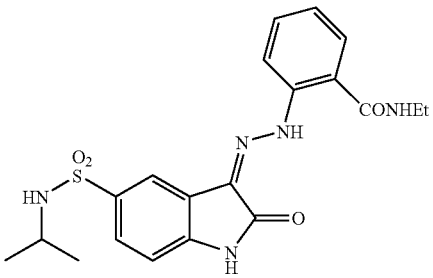

This was obtained as a yellow solid (75%) yield from rpm278 and methylamine (70% solution in water) in a similar manner as described for preparation of rpm292. MS (API-ES): m/z 430 (M+H)⁺; HRMS (API-ES) m/z Found: 430.1538 (M+H)⁺.

3-[N'-(5-Isopropylsulfamoyl-2-oxo-1,2-dihydro-indol-3-ylidene)hydrazino]benzamide (rpm325)

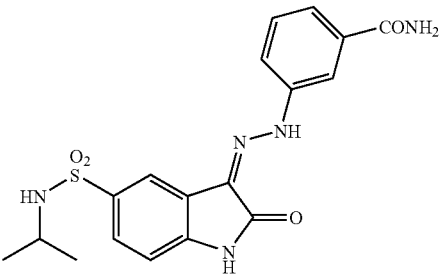 [SMILES: CC(C)NS(=O)(=O)c1ccc2c(c1)/C(=N/Nc1cccc(C(N)=O)c1)C(=O)N2]

This was obtained as a yellow solid (54%) yield from rpm323 and ammonia (2M in ethanol) in a similar manner as described for preparation of rpm292. MS (API-ES): m/z 402 [M+H]⁺, 419 (M+NH₄)⁺, 424 (M+Na)⁺; HRMS (API-ES) m/z Found: 402.1234(M+H)⁺, 419.1490 (M+NH₄)⁺, 424.1050 (M+Na)⁺.

N-(2-Dimethylamino-ethyl)-3-[N'-(5-isopropylsulfamoyl-2-oxo-1,2-dihydro-indol-3-ylidene)hydrazino]benzamide (rpm326)

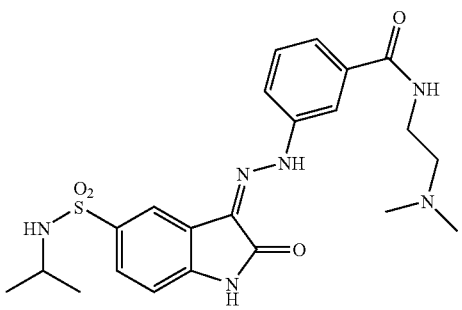 [SMILES: CC(C)NS(=O)(=O)c1ccc2c(c1)/C(=N/Nc1cccc(C(=O)NCCN(C)C)c1)C(=O)N2]

This was obtained as a yellow solid (39%) yield from rpm323 and N,N-dimethylethylenediamine in a similar manner as described for preparation of rpm292. MS (API-ES): m/z 473 (M+H)+; HRMS (API-ES) m/z Found: 473.1976 (M+H)+.

3-[N'-(5-Isopropylsulfamoyl-2-oxo-1,2-dihydro-indol-3-ylidene)hydrazino]-N-(2-methoxyethyl)benzamide (rpm327)

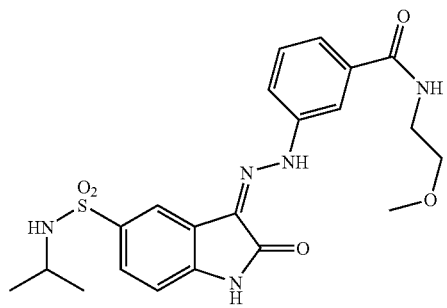 [SMILES: COCCNC(=O)c1cccc(N/N=C2\C(=O)Nc3ccc(S(=O)(=O)NC(C)C)cc32)c1]

This was obtained as a yellow solid (xx%) yield from rpm323 and 2-methoxyethylamine in a similar manner as described for preparation of rpm292. MS (API-ES): m/z 460 (M+H)+; HRMS (API-ES) m/z Found: 460.1649 (M+H+.

N-Benzyl-3-[N'-(5-isopropylsulfamoyl-2-oxo-1,2-dihydro-indol-3-ylidene)hydrazino]benzamide (rpm328)

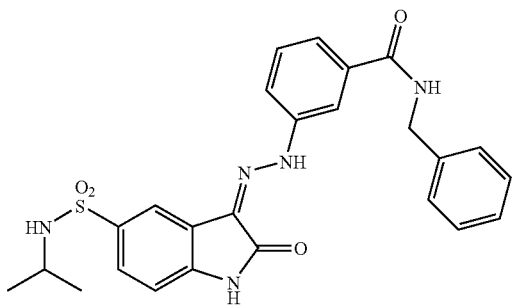 [SMILES: CC(C)NS(=O)(=O)c1ccc2c(c1)/C(=N/Nc1cccc(C(=O)NCc3ccccc3)c1)C(=O)N2]

This was obtained as a yellow solid (70%) yield from rpm323 and benzylamine in a similar manner as described for preparation of rpm292. MS (API-ES): m/z 492 (M+H)+; HRMS (API-ES) m/z Found: 492.1691(M+H)+.

3-[N'-(5-Isopropylsulfamoyl-2-oxo-1,2-dihydro-indol-3-ylidene)hydrazino]-N-pyridin-3-ylmethyl-benzamide (rpm332)

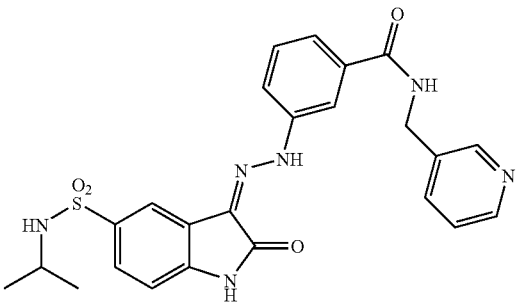 [SMILES: CC(C)NS(=O)(=O)c1ccc2c(c1)/C(=N/Nc1cccc(C(=O)NCc3cccnc3)c1)C(=O)N2]

This was obtained as a yellow solid (70%) yield from rpm323 and 3-(aminomethyl)pyridine in a similar manner as described for preparation of rpm292. MS (API-ES): m/z 493 (M+H)+; HRMS (API-ES) m/z Found: 493.1655 (M+H)+.

N-Furan-2-ylmethyl-3-['-(5-isopropylsulfamoyl-2-oxo-1,2-dihydro-indol-3-ylidene)hydrazino]benzamide (rpm333)

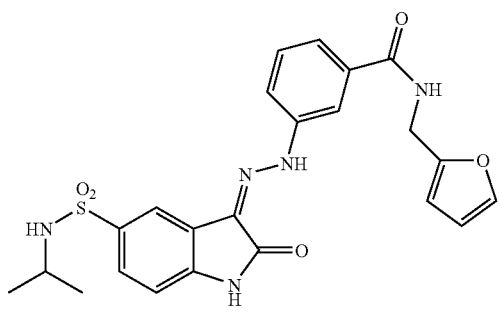 [SMILES: CC(C)NS(=O)(=O)c1ccc2c(c1)/C(=N/Nc1cccc(C(=O)NCc3ccco3)c1)C(=O)N2]

This was obtained as a yellow solid (77%) yield from rpm323 and furfurylamine in a similar manner as described for preparation of rpm292. MS (API-ES): m/z 482 (M+H)+; HRMS (API-ES) m/z Found: 482.1489 (M+H)+.

3-[N'-(5-Isopropylsulfamoyl-2-oxo-1,2-dihydro-indol-3-ylidene)hydrazino]-N-(2-morpholin-4-yl-ethyl)benzamide (rpm334)

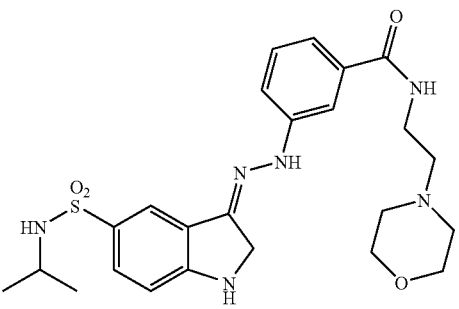 [SMILES: CC(C)NS(=O)(=O)c1ccc2c(c1)/C(=N/Nc1cccc(C(=O)NCCN3CCOCC3)c1)CN2]

This was obtained as a yellow solid (57%) yield from rpm323 and 2-morpholin-4-yl-ethylamine in a similar manner as described for preparation of rpm292. MS (API-ES): m/z 515 (M+H)+; HRMS (API-ES) m/z Found: 515.2071 (M+H)+.

3-[N'-(5-Isopropylsulfamoyl-2-oxo-1,2-dihydro-indol-3-ylidene)hydrazino]-N-methylbenzamide (rpm330)

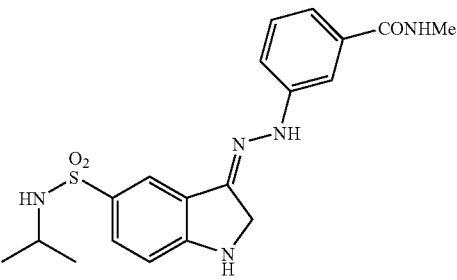

This was obtained as a yellow solid (79%) yield from rpm323 and methylamine (40% solution in water) in a similar manner as described for preparation of rpm292. MS (API-ES): m/z 416 (M+H)⁺; HRMS (API-ES) m/z Found: 416.1389 (M+H)⁺.

N-Ethyl-3-[N'-(5-isopropylsulfamoyl-2-oxo-1,2-dihydro-indol-3-ylidene)hydrazino]benzamide (rpm331)

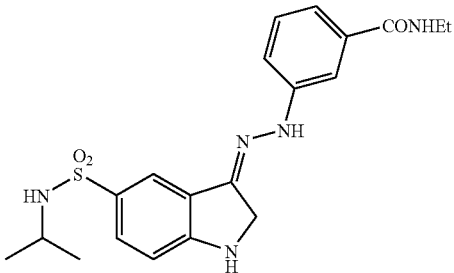

This was obtained as a yellow solid (72%) yield from rpm323 and ethylamine (60% solution in water) in a similar manner as described for preparation of rpm292. MS (API-ES): m/z 430 (M+H)⁺; HRMS (API-ES) m/z Found: 430.1546 (M+H)⁺.

2-Oxo-3-(phenylhydrazono)-2,3-dihydro-1H-indole-5-sulfonic acid (rpm215)

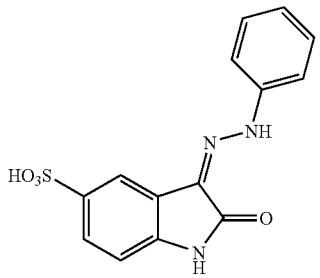 [SMILES: O=C1Nc2ccc(S(=O)(=O)O)cc2/C1=N/Nc1ccccc1]

A mixture of 5-isatinsulfonic acid sodium salt dihydrate (0.092 g, 0.3216 mmol) phenylhydrazine (0.052 g, 0.048 mmol, 1.5 eq) and HCl (aq 4M, 0.8 ml) in ethanol (3 mL) was heated in the CEM microwave at 120° C. for 15 min. The mixture was cooled to room temperature, the yellow precipitate was collected by filtration and dried, to give the pure compound (0.080 g, 0.280 mmol, 87%). MS (API-ES): m/z 316 (M–H)⁻; HRMS (API-ES) m/z Found: 316.0399 (M–H)⁻.

2-Oxo-3-[(2-methylphenylhydrazono)]-2,3-dihydro-1H-indole-5-sulfonic acid (rpm216)

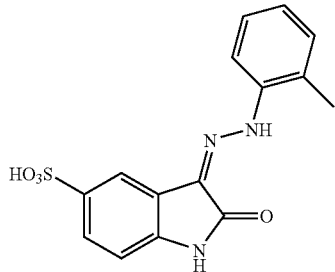 [SMILES: Cc1ccccc1N/N=C1\C(=O)Nc2ccc(S(=O)(=O)O)cc21]

This was obtained as a yellow solid (75%) from 5-isatinsulfonic acid sodium salt dihydrate and 2-methylphenylhydrazine in a similar manner as described for preparation of rpm215. MS (API-ES): m/z 330 (M–H)⁻; HRMS (API-ES) m/z Found: 330.0626, (M–H)⁻.

2-Oxo-3-[(2,6-dichlorophenylhydrazono)]-2,3-dihydro-1H-indole-5-sulfonic acid (rpm218)

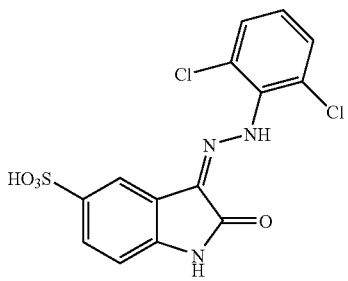 [SMILES: O=C1Nc2ccc(S(=O)(=O)O)cc2/C1=N/Nc1c(Cl)cccc1Cl]

This was obtained as a yellow solid (78%) from 5-isatinsulfonic acid sodium salt dihydrate and 2,6-dichlorophenylhydrazine in a similar manner as described for preparation of rpm215. MS (API-ES): m/z 383.9 (M ³⁵Cl—H)⁻ (100%), 385.9 (M ³⁷Cl—H)⁻ (70%); HRMS (API-ES) m/z Found: 383.9619 (M–H)³¹.

2-Oxo-3-[(2-ethylphenylhydrazono)]-2,3-dihydro-1H-indole-5-sulfonic acid (rpm219)

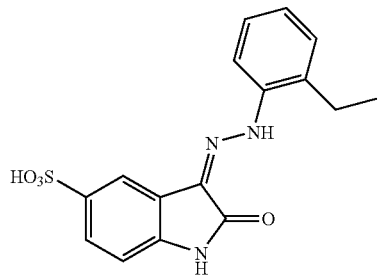 [SMILES: CCc1ccccc1N/N=C1\C(=O)Nc2ccc(S(=O)(=O)O)cc21]

This was obtained as a yellow solid (30%) from 5-isatinsulfonic acid sodium salt dihydrate and 2-ethylphenylhydrazine in a similar manner as described for preparation of rpm215. MS (API-ES): m/z 344 (M–H)⁻; HRMS (API-ES) m/z Found: 344.0717, (M–H)⁻.

2-Oxo-3-[(2-fluorophenylhydrazono)]-2,3-dihydro-1H-indole-5-sulfonic acid (rpm220)

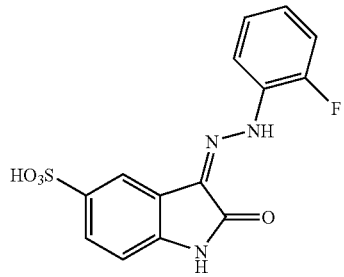 [SMILES: O=C1Nc2ccc(S(=O)(=O)O)cc2/C1=N/Nc1ccccc1F]

This was obtained as a yellow solid (93%) from 5-isatin-sulfonic acid sodium salt dihydrate and 2-fluorophenylhydrazine in a similar manner as described for preparation of rpm215. MS (API-ES): m/z 333.9 (M−H)⁻; HRMS (API-ES) m/z Found: 334.0310, (M−H)⁻.

2-Oxo-3-[(2-trifluoromethylphenylhydrazono)]-2,3-dihydro-1H-indole-5-sulfonic acid (rpm221)

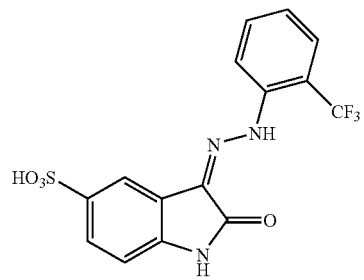 [SMILES: O=C1Nc2ccc(S(=O)(=O)O)cc2/C1=N/Nc1ccccc1C(F)(F)F]

This was obtained as a yellow solid (87%) from 5-isatin-sulfonic acid sodium salt dihydrate and 2-trifluoromethylphenylhydrazine in a similar manner as described for preparation of rpm215. MS (API-ES): m/z 384 (M−H)⁻; HRMS (API-ES) m/z Found: 384.0279 (M−H)⁻.

2-Oxo-3-(pentafluorophenylhydrazono)-2,3-dihydro-1H-indole-5-sulfonic acid (rpm222)

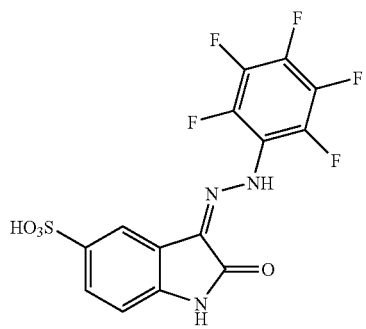 [SMILES: O=C1Nc2ccc(S(=O)(=O)O)cc2/C1=N/Nc1c(F)c(F)c(F)c(F)c1F]

This was obtained as a yellow solid (51%) from 5-isatin-sulfonic acid sodium salt dihydrate and pentafluoromethylphenylhydrazine in a similar manner as described for preparation of rpm215. MS (API-ES): m/z 405.9 (M'H)⁻; HRMS (API-ES) m/z Found: 405.9935 (M−H)⁻.

3-(Naphthalen-1-ylhydrazono)-2-oxo-2,3-dihydro-1H-indole-5-sulfonic acid (rpm223)

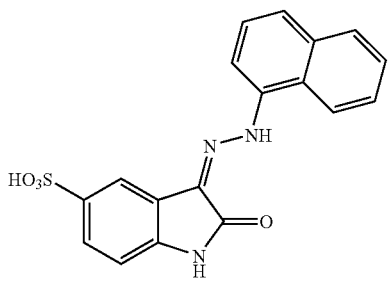 [SMILES: O=C1Nc2ccc(S(=O)(=O)O)cc2/C1=N/Nc1cccc2ccccc12]

This was obtained as a red solid (78%) from 5-isatinsulfonic acid sodium salt dihydrate and 1-naphthylhydrazine in a similar manner as described for preparation of rpm215. MS (API-ES): m/z 366 (M−H)⁻; HRMS (API-ES) m/z Found: 366.0555,(M−H)⁻.

2-Oxo-3-[(2,4-dichlorophenylhydrazono)]-2,3-dihydro-1H-indole-5-sulfonic acid (rpm224)

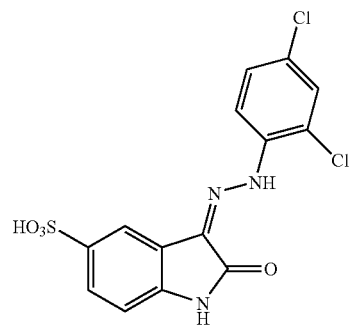 [SMILES: O=C1Nc2ccc(S(=O)(=O)O)cc2/C1=N/Nc1ccc(Cl)cc1Cl]

This was obtained as a yellow solid (69%) from 5-isatin-sulfonic acid sodium salt dihydrate and 2,4-dichlorophenylhydrazine in a similar manner as described for preparation of rpm215. MS (API-ES): m/z 383.9 (M $^{35}$Cl—H)⁻ (100%), 385.9 (M $^{37}$Cl—H)⁻ (70%); HRMS (API-ES) m/z Found: 383.9619(M−H)⁻.

2-Oxo-3-[(2,5-dichlorophenylhydrazono)]-2,3-dihydro-1H-indole-5-sulfonic acid (rpm225)

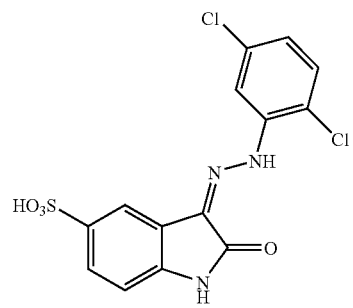 [SMILES: O=C1Nc2ccc(S(=O)(=O)O)cc2/C1=N/Nc1cc(Cl)ccc1Cl]

This was obtained as a yellow solid (76%) from 5-isatin-sulfonic acid sodium salt dihydrate and 2,5-dichlorophenylhydrazine in a similar manner as described for preparation of rpm215. MS (API-ES): m/z 383.9 (M $^{35}$Cl—H)⁻ (100%), 385.9 (M $^{37}$Cl—H)⁻ (70%); HRMS (API-ES) m/z Found: 383.9618 (M—H)⁻.

2-[N'-(2-Oxo-5-sulfo-1,2-dihydro-indol-3-ylidene)hydrazino]benzoic acid (rpm211)

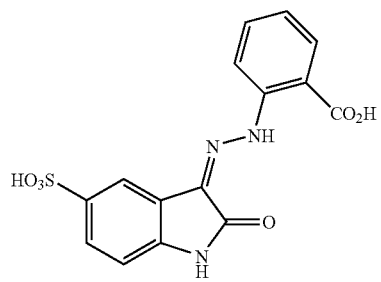

A mixture of 5-isatinsulfonic acid sodium salt dihydrate (0.112 g, 0.391 mmol) 2-carboxylphenylhydrazine (0.052 g, 0.048 mmol, 1.5 eq) and HCl (aq 4M, (0.7 ml) in ethanol (3 mL) was heated in the CEM microwave at 180° C. for 5 min. The reaction mixture was cooled to room temperature, and the yellow precipitate was collected by filtration and dried., to give pure rpm211 (0.116 g, 0.321 mmol, 82%). MS (API-ES): m/z 360 (M–H)⁻; HRMS (API-ES) m/z Found: 360.0297 (M–H)⁻.

2-Oxo-2,3-dihydro-1H-indole-5-sulfonyl chloride² (rpm277)

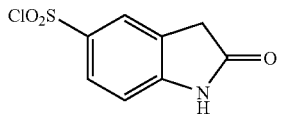 [SMILES: O=C1Cc2cc(S(=O)(=O)Cl)ccc2N1]

Oxindole (5.5 g, 41.30 mmol) was added portionwise to chlorosulfonic acid (50 ml) maintaining the temperature below 30° C. during the addition. After the addition the reaction mixture was stirred at room temperature for 1.5 h and then at 70° C. for 1 h. After cooling to room temperature, the reaction mixture was poured into ice-water (200 ml) and the pink precipitate was filtered, washed with water (50 ml) and dried, to give pure rpm277 (8.4 g, 36.36 mmol, 88%), mp 280-282° C. ¹H NMR (400 MHz, CD₃CN) δ 3.59 (2H, s), 7.10 (1H, d, J 8.7 Hz), 7.92 (1H, s), 7.95 (1H, dd, J 2.2, 8.7 Hz), 8.95 (1H, s, NH).

2-Oxo-2,3-dihydro-1H-indole-5-sulfonic acid isopropylamide (rpm281)

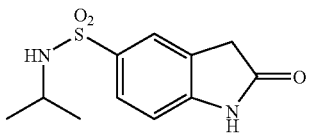 [SMILES: CC(C)NS(=O)(=O)c1ccc2c(c1)CC(=O)N2]

This was obtained from rpm277 and isopropylamine in a similar manner as described for preparation of rpm123. The pure compound was obtained as a pink solid (91%) without further purification (lit Bioorg. and Med. Chem. Lett., 2004, 14, 187.), mp 233-235° C. ¹H NMR (400 MHz, DMSO-d₆) δ 0.92 (6H, d, J .7.6 Hz), 3.15 (1H, sext, J 7.6 Hz), 6.92 (1H, d, J 8.3 Hz), 7.38 (1H, d, J 7.6 Hz), 7.58 (1H, s), 7.61 (1H, dd, J 2.2, 8.3 Hz), 10.74 (1H, s, NH).

2-Oxo-2,3-dihydro-1H-indole-5-sulfonic acid 4-chloro-benzylamide (rpm307)

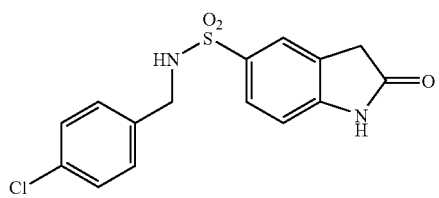 [SMILES: O=C1Cc2cc(S(=O)(=O)NCc3ccc(Cl)cc3)ccc2N1]

This was obtained from rpm277 and 4-chlorobenzylamine in a similar manner as described for preparation of rpm123. The pure compound was obtained as a pink solid (82%) without further purification, mp 145-147° C. ¹H NMR (400 MHz, DMSO-d₆) δ 3.53 (2H, s), 3.92 (2H, s), 6.90 (1H, d, J 8.0 Hz), 7.21 (2H, d, J 8.4 Hz), 7.30 (2H, d, J 8.4 Hz), 7.41 (1H, s), 7.51 (1H, s), 7.61 (1H, d, J 8.0 Hz). ¹³C NMR (100 MHz, DMSO-d₆) δ 177.11, 148.03, 137.52, 133.74, 132.29, 130.13, 128.76, 127.85, 127.22, 123.47, 109.55, 46.07, 36.23. MS m/z (API-ES): 337 [M+H]⁺, 354 (M+NH4)⁺.

3-Dimethylaminomethylene-2-oxo-2,3-dihydro-1H-indole-5-sulfonic acid isopropylamide³ (rpm282).

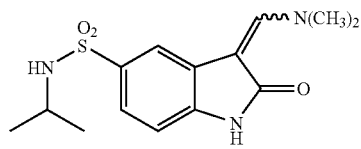 [SMILES: CC(C)NS(=O)(=O)c1ccc2c(c1)C(=CN(C)C)C(=O)N2]

A solution of rpm281 (0.180 g, 0.708 mmol) and N,N-dimethylformamidedimethylacetal (0.125 g, 0.85 mmol, 1.2 eq) in DMF (2 ml) was stirred for 1 h at room temperature. Water (7 ml) was added and the product extracted with ethyl acetate (3×10 ml). The organic extracts were collected, dried over Na₂SO₄ and the solvent evaporated under reduced pressure to give a yellow solid, which was used in the next step without further purification.

3-Dimethylaminomethylene-2-oxo-2,3-dihydro-1H-indole-5-sulfonic acid 4-chlorobenzylamide (rpm309)

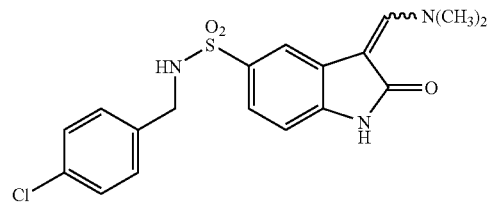 [SMILES: CN(C)C=C1C(=O)Nc2ccc(S(=O)(=O)NCc3ccc(Cl)cc3)cc21]

This was obtained from rpm307 in a similar manner as described for preparation of rpm282. The crude was used in next step without further purification.

2-[(5-Isopropylsulfamoyl-2-oxo-1,2-dihydro-indol-3-ylidenemethyl)amino]benzoic acid methyl ester (rpm335)

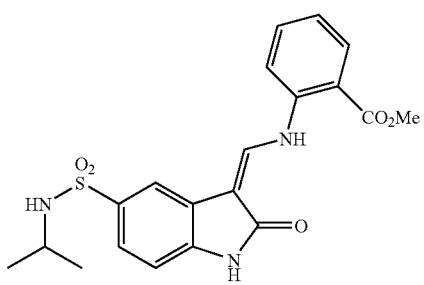 [SMILES: COC(=O)c1ccccc1N/C=C1\C(=O)Nc2ccc(S(=O)(=O)NC(C)C)cc21]

A mixture of rpm282 (0.260 g, 0.841 mmol) methyl-2-aminobenzoate (0.139 g, 0.925 mmol, 1.2 eq) and methansulfonic acid (0.088 g, 0.925 mmol, 1.1 eq) in ethanol (5 mL) was heated in the microwave at 150° C. for 5 min. The reaction mixture was cooled to 0° C., and the orange precipitate was collected by filtration and dried, to give pure rpm335 (0.207 g, 0.498 mmol, 59%). MS (API-ES): m/z 416 (M+H)⁺; HRMS (API-ES) m/z Found: 416.1276 (M+H)⁺.

3-[(5-Isopropylsulfamoyl-2-oxo-1,2-dihydro-indol-3-ylidenemethyl)amino]benzoic acid ethyl ester (rpm302)

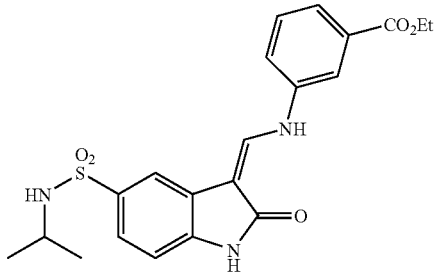 [SMILES: CCOC(=O)c1cccc(N/C=C2\C(=O)Nc3ccc(S(=O)(=O)NC(C)C)cc32)c1]

This was obtained as a yellow solid (47%) from rpm282 and ethyl-3-aminobenzoate in a similar manner as described for preparation of rpm335. MS (API-ES): m/z 430 (M+H)⁺; HRMS (API-ES) m/z Found: 430.1435 (M+H)⁺.

4-[(5-Isopropylsulfamoyl-2-oxo-1,2-dihydro-indol-3-ylidenemethyl)amino]benzoic acid ethyl ester (rpm288)

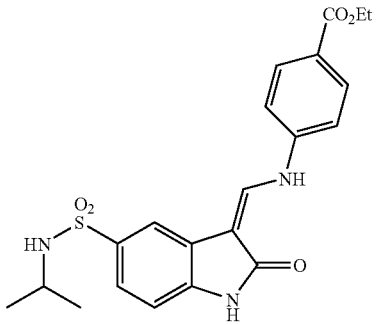 [SMILES: CCOC(=O)c1ccc(N/C=C2\C(=O)Nc3ccc(S(=O)(=O)NC(C)C)cc32)cc1]

This was obtained as a yellow solid (43%) from rpm282 and ethyl-4-aminobenzoate in a similar manner as described for preparation of rpm335. MS (API-ES): m/z 430 [M+H]⁺; HRMS (API-ES) m/z Found 430.1432 (M+H)⁺.

3-[(2-Nitrophenylamino)methylene]-2-oxo-2,3-dihydro-1H-indole-5-sulfonic acid isopropylamide (rpm303)

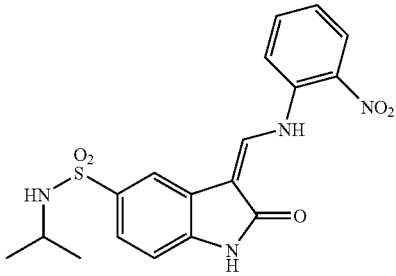

This was obtained as a orange solid (34%) from rpm282 and 2-nitroaniline in a similar manner as described for preparation of rpm335. MS (API-ES): m/z 403 [M+H]⁺; HRMS (API-ES) m/z Found: 430.1070 (M+H)⁺.

3-[(2-Nitrophenylaminomethylenel-2-oxo-2,3-dihydro-1H-indole-5-sulfonic acid 4-chlorobenzylamide (rpm310)

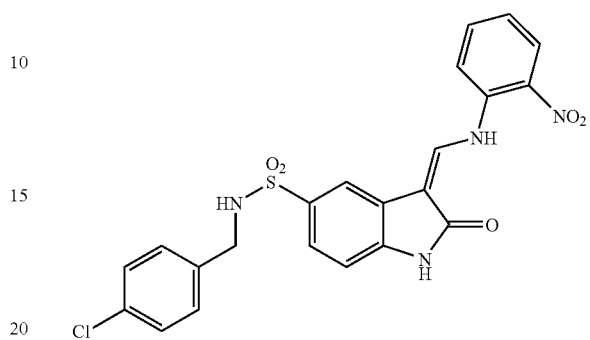

This was obtained as an orange solid (33%) from rpm309 and 2-nitroaniline in a similar manner as described for preparation of rpm335. MS (API-ES): m/z 485 [M+H]⁺; HRMS (API-ES) m/z Found 485.0677 (M+H)⁺.

2-[(5-Isopropylsulfamoyl-2-oxo-1,2-dihydro-indol-3-ylidenemethyl)amino]benzoic acid (rpm336)

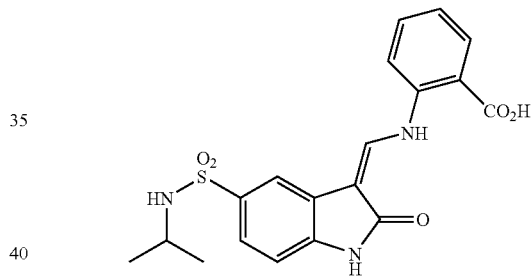

A suspension of rpm335 (0.155 g, 0.3734 mmol) in methanol (1 mL) and NaOH 1M (1 ml) was heated in the microwave at 150° C. for 5 min. The reaction mixture was cooled to 0° C., and the solvent distilled under reduced pressure and HCl (aq 4M, 5 ml) added. The orange precipitate was collected by filtration, washed with water (10 ml) and dried, to give pure rpm336 (0.139 g, 0.346 mmol, 92%). MS (API-ES): m/z 402 (M+H)⁺; HRMS (API-ES) m/z Found: 402.1116 (M+H)⁺.

3-[(5-Isopropylsulfamoyl-2-oxo-1,2-dihydro-indol-3-ylidenemethyl)amino]benzoic acid (rpm304)

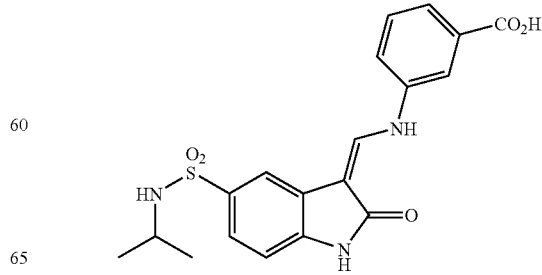

This was obtained as an orange solid (40%) from rpm302 in a similar manner as described for preparation of rpm336. MS (API-ES): m/z 402 (M+H)$^+$; HRMS (API-ES) m/z Found: 402.1114 (M+H)$^+$.

4-[(5-Isopropylsulfamoyl-2-oxo-1,2-dihydro-indol-3-ylidenemethyl)amino]benzoic acid (rpm305)

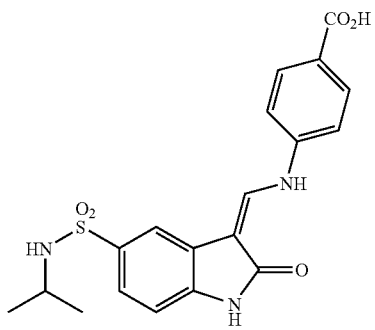 [SMILES: CC(C)NS(=O)(=O)c1ccc2c(c1)/C(=C/Nc1ccc(C(=O)O)cc1)C(=O)N2]

This was obtained as an orange solid (33%) from rpm288 in a similar manner as described for preparation of rpm336. MS (API-ES): m/z 402 (M+H)$^+$; HRMS (API-ES) m/z Found: 402.1119 (M+H)$^+$.

3,3-Dibromo-2-oxo-2,3-dihydro-1H-indole-5-carboxylic acid methyl ester (rpm262)

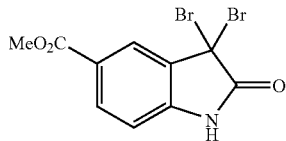 [SMILES: COC(=O)c1ccc2c(c1)C(Br)(Br)C(=O)N2]

To a solution of 5-methylindole-2-carboxylate (4.5 g, 25.71 mmol) in isopropanol (350 ml) NBS (13.41 g, 74.91 mmol, 4 eq) was added portionwise within 45 minutes under Ar. After the addition the solvent was removed under reduced pressure and the solid residue was triturated with cold acetone (150 ml) to give the pure product as a yellow solid (4.9 g, 14.08 mmol, 55%). $^1$H (400 MHz, DMSO-d$_6$) δ 3.86 (3H, s), 7.05 (1H, d, J 8.2 Hz), 7.96 (1H, dd, J 8.2, 1.6 Hz, CH, Ar), 8.05 (1H, s), 11.71 (1H, bs).

3-[(2-Chlorophenyl)hydrazonol-2-oxo-2,3-dihydro-1H-indole-5-carboxylic acid (RPM270)

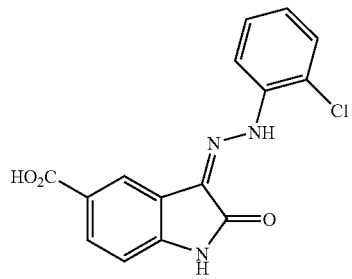 [SMILES: O=C1Nc2ccc(C(=O)O)cc2/C1=N/Nc1ccccc1Cl]

A mixture of rpm262 (0.052 g, 0.149 mmol) in HCl 4 M (2 ml) was heated in the CEM microwave at 150° C. for 5 min. After cooling down to room temperature, 2-chlorohydrazine (0.026 g, 0.149 mmol, 1 eq) was added to the reaction mixture, which was heated in the microwave at 150° C. for 5 min. After cooling down to room temperature, the formed yellow solid was collected by filtration washed with water (5 ml), cold methanol (2 ml) and dried. The pure compound was obtained without further purification (0.039 g, 0.121 mmol, 81). MS (API-ES): m/z 313.9 (M $^{35}$Cl—H)$^-$ (100%), 316 (M $^{37}$Cl—H)$^-$ (70%); HRMS (API-ES) m/z Found: 314.0344, (M–H)$^-$.

3-(Phenylhydrazono)-2-oxo-2,3-dihydro-1H-indole-5-carboxylic acid (rpm272)

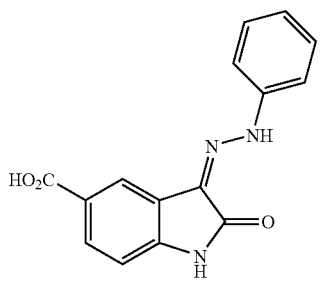

This was obtained as a yellow solid (76%) from rpm262 and phenylhydrazine in a similar manner as described for preparation of rpm270. MS (API-ES): m/z 282 (M+H)$^+$ (100%); HRMS (API-ES) m/z Found: 282.0875 (M+H)$^+$.

3-[(2-Fluorophenyl)hydrazonol-2-oxo-2,3-dihydro-1H-indole-5-carboxylic acid (rpm319)

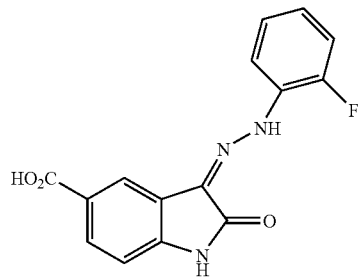 [SMILES: O=C1Nc2ccc(C(=O)O)cc2/C1=N/Nc1ccccc1F]

This was obtained as a yellow solid (72%) from rpm262 and 2-fluorophenylhydrazine in a similar manner as described for preparation of rpm270. MS (API-ES): m/z 298 (M–H)$^-$; HRMS (API-ES) m/z Found: 298.0639(M–H)$^-$.

3-[(2-Ethylphenyl)hydrazono]-2-oxo-2,3-dihydro-1H-indole-5-carboxylic acid (rpm320)

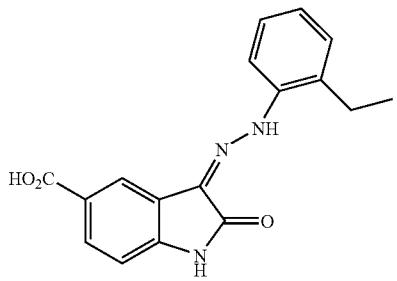 [SMILES: CCc1ccccc1N/N=C1\C(=O)Nc2ccc(C(=O)O)cc21]

This was obtained as a yellow solid (65%) from rpm262 and 2-ethylphenylhydrazine in a similar manner as described for preparation of rpm270. MS (API-ES): m/z 308 (M−H)$^-$; HRMS (API-ES) m/z Found: 308.1044 (M−H)$^-$.

HL2-052-2. This was obtained as a yellow solid from rpm262 and 2-carboxylphenylhydrazine in a similar manner as described for preparation of rpm270. HL2-052-2: $^1$H NMR (DMSO-d$_6$, 400 MHz) δ 14.22 (s, 1H), 11.27 (s, 1H), 8.11 (s, 1H), 8.07 (d, J=8.4 Hz, 1H), 7.94-7.92 (dd, J=7.6 Hz, 1.2 Hz, 1H), 7.89-7.86 (dd, J=8.4 Hz, 1.6 Hz, 1H), 7.65-7.61 (appt, 1H), 7.11-7.07 (appt, 1H), 6.99 (d, J=10.4 Hz, 1H).

HL2-052-3. This was obtained as a yellow solid from rpm262 and 3-carboxylphenylhydrazine in a similar manner as described for preparation of rpm270. HL2-052-3: $^1$H NMR (DMSO-d$_6$, 400 MHz) δ 12.96 (broad s, 1H), 12.70 (s, 1H), 11.37 (s, 1H), 8.06 (s, 1H), 8.00 (s, 1H) 7.87-7.85 (dd, J=8.4 Hz, 1.2 Hz, 1H), 7.72 (d, J=8.0 Hz, 1H), 7.60 (d, J=7.2 Hz, 1H), 7.49-7.45 (appt, 1H), 7.00 (d, J=8.4 Hz, 1H).

HL2-054. This was obtained as a yellow solid from rpm262 and 2-nitrophenylhydrazine in a similar manner as described for preparation of rpm270

2-(5-Isopropylsulfamoyl-2-oxo-1,2-dihydro-indol-3-ylidenemethyl)benzoic acid methyl ester (rpm347)

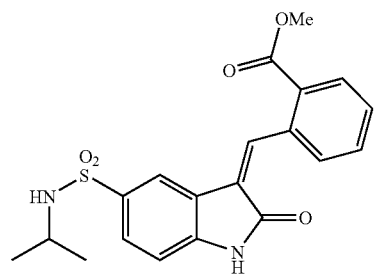 [SMILES: COC(=O)c1ccccc1/C=C1\C(=O)Nc2ccc(S(=O)(=O)NC(C)C)cc21]

A solution of rpm281 (0.149 g, 0.586 mmol) and methyl 2-formylbenzoate (0.105 g, 0.645 mmol, 1.1 eq) in ethanol (10 ml) was stirred in presence of piperidine (1 drop) at 80° C., under Ar for 1 h. After cooling to room temperature, the solvent was removed under reduced pressure. The residue was dissolved in ethyl acetate (15 ml) and washed with HCl 1M (10 ml). The organic extracts were collected, dried over Na$_2$SO$_4$ and the solvent removed under reduced pressure to afford a orange solid. The pure compound rpm347 was obtained after trituration with hexane/ethyl acetate mixture (6:4) (10 ml) as a off-white solid (0.135 g, 0.337 mmol, 60%), mp 271-273° C. MS (API-ES): m/z 401 (M+H)$^+$; HRMS (API-ES) m/z Found: 401.1173 (M+H)$^+$.

3-Benzoyl-1H-indole-5-carboxylic acid methyl ester (rpm341)

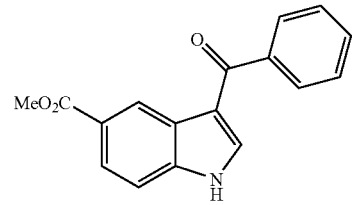 [SMILES: COC(=O)c1ccc2[nH]cc(C(=O)c3ccccc3)c2c1]

Alluminium trichloride (0.550 g, 2.50 mmol, 2.2 eq) was added to a solution of benzoyl chloride (0.319 g, 2.274 mol, 2 eq) in anhydrous DCM (5 ml). After stirring at room temperature under Ar for 30 min, methyl 5-carboxy indole (0.199 g, 1.157 mmol) was added. After stirring for 2 h at room temperature, the reaction mixture was poured into water (5 ml). The product was extracted with DCM (3×10 ml). The organic extracts were collected, dried over Na$_2$SO$_4$ and the solvent removed under reduced pressure to afford a brown solid. The pure compound rpm123 was obtained after trituration with hexane (10 ml) as a off-whte solid (0.205 g, 0.737 mmol, 64%), mp 271-273° C. $^1$H (400 MHz, DMSO-d$_6$) δ 3.87 (3H, s), 7.52-7.61 (4H, m), 7.79-7.31 (2H, m), 7.87 (1H, dd, J 1.4, 8.6 Hz), 8.08 (1H, d, J 3.2 Hz), 8.9 (1H, d, J 1.2 Hz), 12.36 (1H, s). $^{13}$C NMR (100 MHz, DMSO-d$_6$) δ 190.64, 167.70, 140.74, 140.16, 138.34, 132.07, 129.19, 129.14, 126.61, 124.77, 124.51, 123.93, 116.30, 113.13, 52.61.

3-(Naphthalene-2-carbonyl)-1H-indole-5-carboxylic acid methyl ester (rpm350)

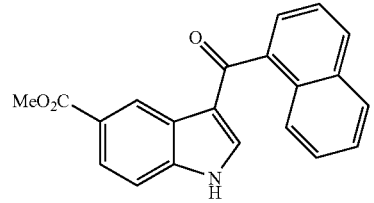 [SMILES: COC(=O)c1ccc2[nH]cc(C(=O)c3cccc4ccccc34)c2c1]

This was obtained as a white solid (71%) yield from methyl 5-carboxyindole and 1-naphthoyl chloride in a similar manner as described for preparation of rpm341, mp>300+ C. $^1$H (400 MHz, DMSO-d$_6$) δ 3.96 (3H, s), 7.44-7.53 (5H, m), 7.66 (1H, dd, J 1.0, 7.0 Hz), 7.90 (1H, d, J 7.2 Hz), 7.97 (1H, d, J 8.4 Hz), 8.06 (1H, dd, J 2.0, 7.6 Hz), 8.18 (1H, d, J 8.4 Hz), 8.96 (1H, bs), 9.26 (1H, d, J 1.6 Hz). $^{13}$C NMR (100 MHz, DMSO-d$_6$) δ 52.64, 113.26, 118.46, 124.40, 124.52, 124.95, 125.61, 125.91, 126.17, 126.65, 127.03, 127.55, 129.03, 130.67, 130.70, 134.03, 138.73, 139.20, 140.32, 167.67, 192.51.

3-Benzoyl-1H-indole-5-carboxylic acid (rpm352)

This was obtained as a white solid (71%) yield from methyl rpm350 in a similar manner as described for preparation of rpm336, mp>300° C. $^1$H (400 MHz, DMSO-$d_6$) δ 7.52-7.63 (4H, m), 7.79 (2H, d, J 6.8 Hz), 7.85 (1H, dd, J 1.2, 8.4 Hz), 8.05 (2H, t, J 2.4 Hz), 8.9 (1H, s), 10.61 (1H, s), 12.33 (1H, bs). $^{13}$C NMR (100 MHz, DMSO-$d_6$) δ 190.66, 168.77, 140.80, 139.89, 137.98, 132.02, 129.17, 129.14, 126.52, 125.06, 124.69, 116.32, 112.80.

3-(Naphthalene-2-carbonyl)-1H-indole-5-carboxylic acid (rpm351)

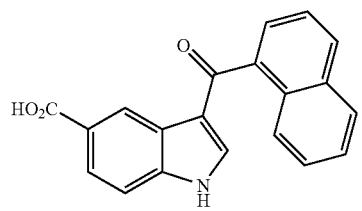 [SMILES: O=C(O)c1ccc2[nH]cc(C(=O)c3cccc4ccccc34)c2c1]

This was obtained as a white solid (71%) yield from methyl rpm350 in a similar manner as described for preparation of rpm336, mp>300° C. $^1$H (400 MHz, DMSO-$d_6$) δ 7.49-7.43 (4H, m), 7.71 (1H, d, J 6.4 Hz), 7.79 (1H, m), 7.88 (1H, dd, J 1.8, 8.6 Hz), 8.01 (2H, t, J 8.2 Hz), 8.09 (1H, d, J 7.6 Hz), 8.98 (1H, s), 12.31 (1H, bs). $^{13}$C NMR (100 MHz, DMSO-$d_6$) δ 113.00, 118.45, 124.66, 125.19, 125.34, 125.62, 125.93, 126.11, 126.62, 127.02, 127.54, 129.03, 130.62, 130.71, 134.02, 138.82, 139.00, 140.16, 168.76, 192.12.

Figure 7:
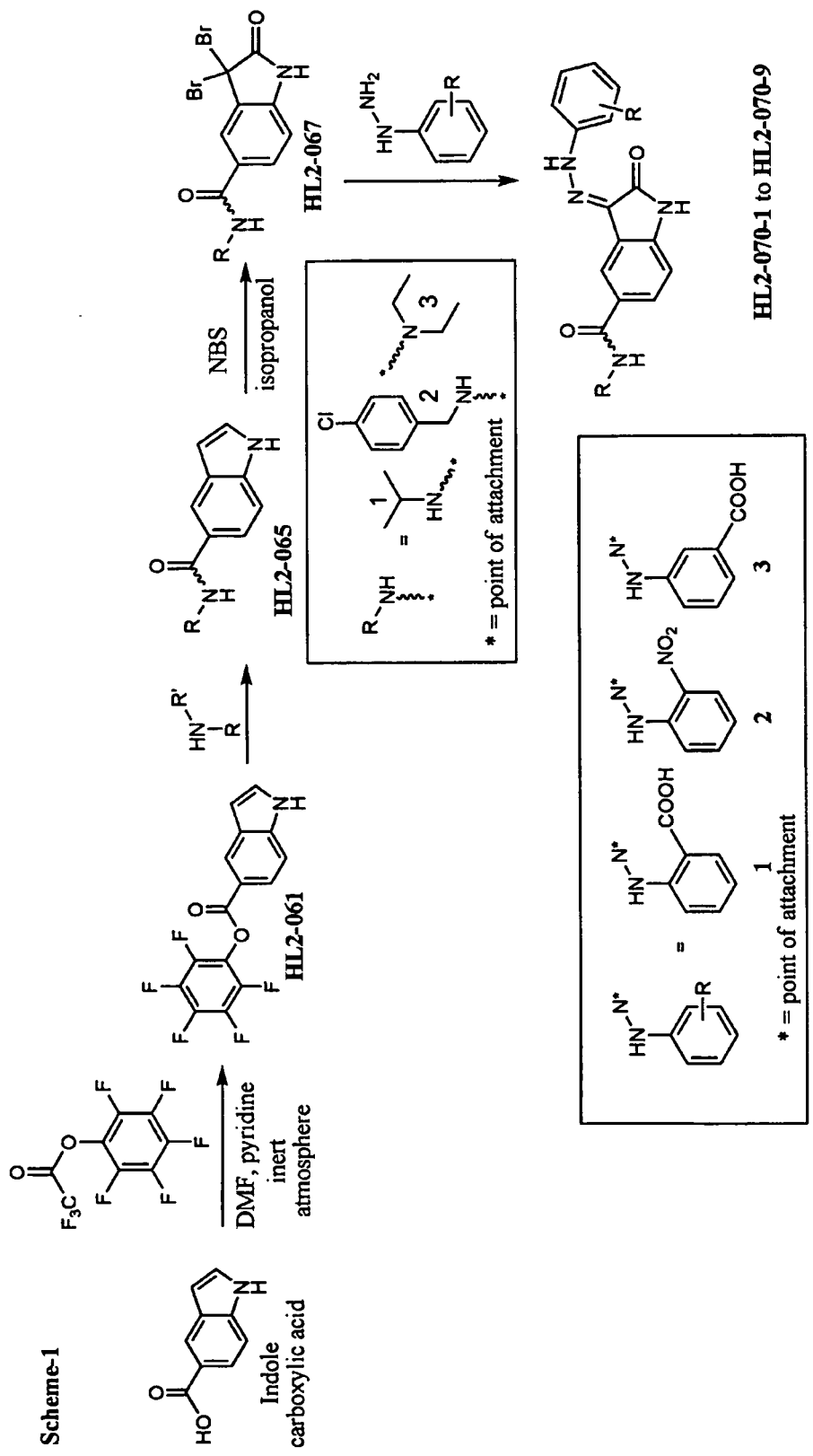
FIG. 7 is an overview of scheme 1 chemical synthesis.

Synthesis of Pentafluorophenyl ester HL2-061 (See FIG. 7)

To a solution of indole carboxylic acid (0.5 g, 3.10 mmol) in DMF (3.00 ml) was added pentafluorophenyl trifluoroacetate (6.2 mmol, 1.068 ml) followed by pyridine (0.281 ml). The reaction mixture (a suspension was obtained at this stage) was stirred at r.t. under inert atmosphere for approximately 30 minutes. The reaction mixture was poured into ether (40 ml) and diluted with ethyl acetate (2×50 ml). The organics were washed with water, dried (Na$_2$SO$_4$) and concentrated to obtain an off white solid (70% yield, 720 mg, t.l.c. R$_f$=0.71 EtOAc : Hexane, 1:1). No purification was necessary: $^1$H NMR (DMSO-$d_6$, 400 MHz) δ 11.7 (s,1H, NH), 8.49 (s, 1H), 7.87-7.84 (dd, J=8 Hz, 4 Hz, 1H), 7.59-7.55 (m, 2H), 6.67-6.66 (s, 1H).

General Procedure for Synthesis of Intermediates; HL2-065-1, HL2-065-2, HL2-065-3

The starting material HL2-061 (200 mg, 0.612 mmol) was suspended in dry acetonitrile under argon, pyridine was added (0.075 ml, 0.85 mmol) followed by the appropriate aniline (0.85 mmol) shown above and stirred overnight (approximately 12 h). The resulting cloudy solution was diluted with EtOAc and washed with 4M HCl (6 ml). The organic phase was separated, washed with water, dried (Na$_2$SO$_4$), and concentrated to obtain HL2-065-1 (203 mg, colourless oil), HL2-065-2 (252 mg, orange solid) and HL2-065-3 (125 mg, pale yellow sold). These compounds were used in the next stage without further purification.

HL2-065-1: $^1$H NMR (DMSO-$d_6$, 400 MHz) δ 11.25 (s, NH), 8.09 (s, 1H), 8.02 (d, J=8.0 Hz, 1H, disappeared on D$_2$O shake), 7.61-7.59 (dd, J=8.8 Hz, 1.2 Hz, 1H), 7.40-7.36 (m, 2H), 6.50-6.49 (s, 1H), 4.12-4.07 (m, 1H), 1.16 and 1.14 (2 ×s, 6H).

HL2-065-2: $^1$H NMR (DMSO-$d_6$, 400 MHz) δ 11.31 (s, 1H), 8.93-8.90 (t, J=8.0 Hz, 1H), 8.14 (s, 1H), 7.64-7.62 (dd, J=8 Hz, 1.2 Hz, 1H)7.40-7.31 (m, 5H) 6.51 (s, 1H), 4.45 (s, 2H).

HL2-065-3: $^1$H NMR (DMSO-$d_6$, 400 MHz) δ 11.25 (s, 1H), 7.52 (s,1H), 7.40-7.38 (m, 2H), 7.06-7.04 (dd, J=8 Hz, 1.6 Hz, 1H), 6.46-6.54 (s, 1H) 3.32 (broad peak overlapped with H$_2$O), 1.13-1.08 (broad s, 6H).

General Procedure for Synthesis of dibromo-oxindole Intermediates; HL2-067-1, HL2-067-2, HL2-067-3

The starting material HL2-065-1 (203 mg, 1.0 mmol), HL2-065-2 (252 mg. 0.88 mmol) and HL2-065-3 (125 mg, 0.557 mmol) was dissolved in aqueous isopropanol (5 ml), and NBS was added (0.533 g, 0.471 g, and 0.307 respectively, portion wise over 30 min. period) with stirring under argon atmosphere. Reaction was monitored by t.l.c (EtOAc: Hexane, 1:1). T.L.C. indicated the disappearance of the starting material. The reaction mixture was concentrated at r.t. The succinimide precipitate was filtered, washed with ether. The ether phase was concentrated to obtain the dibromo-oxindole products HL2-067-1 (220 mg), HL2-067-2 (225 mg) and HL2-067-3 (220 mg). These compounds were used in the next step without purification.

General Procedure for Synthesis of Final oxindole Compounds; HL2-070-1, HL2-070-2, HL2-070-3, HL2-070-4, HL2-070-5, HL2-070-6, HL2-070-7, HL2-070-8, HL2-070-9

The dibromoisatin amide intermediate HL2-067-1 (0.052 mg), HL2-067-2 (70 mg) and HL2-067-3 (72 mg mg) from the above procedure was suspended in MeOH (2.0 ml) in a microwave tube (CEM, 10 ml), and the required hydrazines (1.1 equivalents) were added (as shown in the Scheme 1) and irradiated for 5 minutes at 150° C. in CEM microwave reactor. The reaction tubes were left in an ice bath until a precipitate formed. The solid precipitate was filtered and analyzed by $^1$H NMR, Low Resolution Mass spectroscopy and High resolution Mass Spectroscopy (see Table 1 for mass spectral data). The average yield of the pure product isolated was 15 mg.

HL2-070-1: $^1$H NMR (DMSO-$d_6$, 400 MHz) δ 14.22 (s, 1H, disappeared on D$_2$O shake), 11.08 (s, 1H, disappeared on D$_2$O shake), 8.07 (d, J=8.8 Hz, 1H), 7.94 (appd, 1H), 7.61-

7.56 (m, 2H), 7.26 (d, J=1.6 Hz, 1H), 7.08 (m, 1H), 6.95 (appd, 1H), 1.15 (s, 6H), N—CH$_2$ signals overlapped with residual DMSO.

HL2-070-2: $^1$H NMR (DMSO-d$_6$, 400 MHz) δ 12.75 (s, 1H), 11.19 (s, 1H), 7.98 (s, 1H), 7.70 (d, J=7.2 Hz, 1H), 7.60 (d, J=8 Hz, 1H), 7.50-7.45 (m, 2H), 7.24 (d, J=8.4 Hz, 1H), 6.94 (d, J=7.6 Hz, 1H), 7.07 (s, 6H), N—CH$_2$ signals overlapped with residual DMSO. In CD$_3$-OD NMR displayed following peaks: $^1$H NMR (CD$_3$-OD, 400 MHz) δ (8.07 (s, 1H), 7.26 (d, J=0.8 Hz, 1H), 7.63-7.60 (m, 2H), 7.49-7.47 (m, 1H), 7.29 (d, J=8.0 Hz, 1H), 7.01 (d, J=8 Hz, 1H), 3.57-3.55 (2×m partially overlapped with H$_2$O, 4H), 1.19-1.18 (2×s, 6H).

HL2-070-3: $^1$H NMR (DMSO-d$_6$, 400 MHz) δ 11.23 (s, 1H, disappeared on D$_2$O shake), 11.32 (s, 1H, disappeared on D$_2$O shake), 8.28 (d, J=8 Hz, 1H), 8.22 (d, J=8.4 Hz, 1H), 7.79 (broad s, 1H), 7.64 (s, 1H), 7.32 (d, J=7.6 Hz, 1H), 7.19 (broad t, 1H), 6.98 (d, J=6.8 Hz, 1H), 1.13 (s, 6H), N—CH$_2$-signals are overlapped with H$_2$O signal.

HL2-070-4: $^1$H NMR (DMSO-d$_6$, 400 MHz) δ 14.23 (s, 1H), 11.19 (s, 1H), 9.08 (t, 1H), 8.17 (s, 1H), 7.95-7.84 (dd, J=16 Hz, 1.2 Hz, 2H), 7.65-7.64 (t, J=1.8 Hz, 1H), 7.39-7.35 (m, 5H), 7.11-7.07 (t, J=14 Hz, 1H), 6.98 (d, J=8.4 Hz, 1H), 4.47-4.45 (d, J=5.6 Hz, 3H).

HL2-070-5: $^1$H NMR (DMSO-d$_6$, 400 MHz) δ 12.79 (s, 1H), 11.31 (s, 1H), 9.13 (s, 1H0, 8.12 (s, 1H), 8.04 (s, 1H), 7.84 (d, J=8.0 Hz, 1H), 7.68-7.60 (dd, J=24.0 Hz, 8.0 Hz, 2H), 7.50-7.46 (m, 1H), 7.37-7.33 (m, 4H), 76.99 (d, J=8.0 Hz, 1H), 4.47 (s, 2H).

HL2-070-6: See Table for Low Resolution and High resolution mass spectra.

HL2-070-7: See Table for Low Resolution and High resolution mass spectra.

HL2-070-9: See Table for Low Resolution and High resolution mass spectra.

HL2-052-3: $^1$H NMR (DMSO-d$_6$, 400 MHz) δ 12.96 (broad s, 1H), 12.70 (s, 1H), 11.37 (s, 1H), 8.06 (s, 1H), 8.00 (s, 1H) 7.87-7.85 (dd, J=8.4 Hz, 1.2 Hz, 1H), 7.72 (d, J=8.0 Hz, 1H), 7.60 (d, J=7.2 Hz, 1H), 7.49-7.45 (appt, 1H), 7.00 (d, J=8.4 Hz, 1H).

References

Alonso A, Sasin J, Bottini N, Friedberg I, Friedberg I, Osterman A, Godzik A, Hunter T, Dixon J and Mustelin T (2004) Protein tyrosine phosphatases in the human genome. *Cell* 117(6):699-711.

Andersen J N, Mortensen O H, Peters G H, Drake P G, Iversen L F, Olsen O H, Jansen P G, Andersen H S, Tonks N K and Moller N P (2001) Structural and evolutionary relationships among protein tyrosine phosphatase domains. *Mol Cell Biol* 21(21):7117-7136.

Bennett A M, Hausdorff S F, O'Reilly A M, Freeman R M and Neel B G (1996) Multiple requirements for SHPTP2 in epidermal growth factor-mediated cell cycle progression. *Mol Cell Biol* 16(3):1189-1202.

Bentires-Alj M, Paez J G, David F S, Keilhack H, Halmos B, Naoki K, Maris J M, Richardson A, Bardelli A, Sugarbaker D J, Richards W G, Du J, Girard L, Minna J D, Loh M L, Fisher D E, Velcuescu V V, Vogelstein B, Meyerson M, Sellers W R and Neel B G (2004) Activating mutations of the noonan syndrome-associated SHP2/PTPN11 gene in human solid tumors and adult acute myelogenous leukemia. *Cancer Res* 64(24):8816-8820.

Bialy L and Waldmann H (2005) Inhibitors of protein tyrosine phosphatases: next-generation drugs? *Angew Chem Int Ed Engl* 44(25):3814-3839.

Carroll M P and May W S (1994) Protein kinase C-mediated serine phosphorylation directly activates Raf-1 in murine hematopoietic cells. *J Biol Chem* 269(2):1249-1256.

Chan R J, Leedy M B, Munugalavadla V, Voorhorst C S, Li Y, Yu M and Kapur R (2005) Human somatic PTPN11 mutations induce hematopoietic-cell hypersensitivity to granulocyte-macrophage colony-stimulating factor. *Blood* 105(9): 3737-3742.

Chen, L, Sang, S, Yip, M L R, Lawrence, H R, Ren, Y, Guida, W C, sebti, S M, Lawrence, N J, and Wu, J (2006) Discovery of a novel Shp2 protein tyrosine phosphatase inhibitor. *Mol Pharmacol* 70:562-570.

Cunnick J M, Dorsey J F, Mei L and Wu J (1998) Reversible regulation of SHP-1 tyrosine phosphatase activity by oxidation. *Biochem Mol Biol Int* 45(5):887-894.

Cunnick J M, Mei L, Doupnik C A and Wu J (2001) Phosphotyrosines 627 and 659 of Gab1 constitute a bisphosphoryl tyrosine-based activation motif (BTAM) conferring binding and activation of SHP2. *J Biol Chem* 276(26):24380-24387.

Cunnick J M, Meng S, Ren Y, Desponts C, Wang H G, Djeu J Y and Wu J (2002) Regulation of the mitogen-activated protein kinase signaling pathway by SHP2. *J Biol Chem* 277(11):9498-9504.

Deb T B, Wong L, Salomon D S, Zhou G, Dixon J E, Gutkind J S, Thompson S A and Johnson G R (1998) A common requirement for the catalytic activity and both SH2 domains of SHP-2 in mitogen-activated protein (MAP) kinase activation by the ErbB family of receptors. A specific role for SHP-2 in map, but not c-Jun amino-terminal kinase activation. *J Biol Chem* 273(27):16643-16646.

Fragale A, Tartaglia M, Wu J and Gelb B D (2004) Noonan syndrome-associated SHP2/PTPN11 mutants cause EGF-dependent prolonged GAB1 binding and sustained ER2/MAPK1 activation. *Hum Mutat* 23(3):267-277.

Friesner R A, Banks J L, Murphy R B, Halgren T A, Klicic J J, Mainz D T, Repasky M P, Knoll E H, Shelley M, Perry J K, Shaw D E, Francis P and Shenkin P S (2004) Glide: a new approach for rapid, accurate docking and scoring. 1. Method and assessment of docking accuracy. *J Med Chem* 47(7): 1739-1749.

Gu H and Neel B G (2003) The "Gab" in signal transduction. *Trends Cell Biol* 13(3): 122-130.

Halgren T A, Murphy R B, Friesner R A, Beard H S, Frye L L, Pollard W T and Banks J L (2004) Glide: a new approach for rapid, accurate docking and scoring. 2. Enrichment factors in database screening. *J Med Chem* 47(7):1750-1759.

Hatakeyama M (2004) Oncogenic mechanisms of the Helicobacter pylori CagA protein. *Nat Rev Cancer* 4(9):688-694.

Hof P, Pluskey S, Dhe-Paganon S, Eck M J and Shoelson S E (1998) Crystal structure of the tyrosine phosphatase SHP-2. *Cell* 92(4):441-450.

Huang P, Ramphal J, Wei J, Liang C, Jallal B, McMahon G and Tang C (2003) Structure-based design and discovery of novel inhibitors of protein tyrosine phosphatases. *Bioorg Med Chem* 11(8):1835-1849.

Keilhack H, David F S, McGregor M, Cantley L C and Neel B G (2005) Diverse biochemical properties of Shp2 mutants. Implications for disease phenotypes. *J Biol Chem* 280(35): 30984-30993.

Kolch W, Heidecker G, Kochs G, Hummel R, Vahidi H, Mischak H, Finkenzeller G, Marme D and Rapp U R (1993) Protein kinase C alpha activates RAF-1 by direct phosphorylation. *Nature* 364(6434):249-252.

Kratz C P, Niemeyer C M, Castleberry R P, Cetin M, Bergstrasser E, Emanuel P D, Hasle H, Kardos G, Klein C, Kojima S, Stary J, Trebo M, Zecca M, Gelb B D, Tartaglia M and Loh M L (2005) The mutational spectrum of PTPN11 in juvenile myelomonocytic leukemia and Noonan syndrome/myeloproliferative disease. *Blood* 106(6):2183-2185.

Lazo J S, Nemoto K, Pestell K E, Cooley K, Southwick E C, Mitchell D A, Furey W, Gussio R, Zaharevitz D W, Joo B and Wipf P (2002) Identification of a potent and selective pharmacophore for Cdc25 dual specificity phosphatase inhibitors. *Mol Pharmacol* 61(4):720-728.

Maroun C R, Naujokas M A, Holgado-Madruga M, Wong A J and Park M (2000) The tyrosine phosphatase SHP-2 is required for sustained activation of extracellular signal-regulated kinase and epithelial morphogenesis downstream from the met receptor tyrosine kinase. *Mol Cell Biol* 20(22):8513-8525.

McCain D F, Wu L, Nickel P, Kassack M U, Kreimeyer A, Gagliardi A, Collins D C and Zhang Z Y (2004) Suramin derivatives as inhibitors and activators of protein-tyrosine phosphatases. *J Biol Chem* 279(15):14713-14725.

Mohi M G, Williams I R, Dearolf C R, Chan G, Kutok J L, Cohen S, Morgan K, Boulton C, Shigematsu H, Keilhack H, Akashi K, Gilliland D G and Neel B G (2005) Prognostic, therapeutic, and mechanistic implications of a mouse model of leukemia evoked by Shp2 (PTPN11) mutations. *Cancer Cell* 7(2):179-191.

Neel B G, Gu H and Pao L (2003) The 'Shp'ing news: SH2 domain-containing tyrosine phosphatases in cell signaling. *Trends Biochem Sci* 28(6):284-293.

Nishida K and Hirano T (2003) The role of Gab family scaffolding adapter proteins in the signal transduction of cytokine and growth factor receptors. *Cancer Sci* 94(12):1029-1033.

O'Reilly A M and Neel B G (1998) Structural determinants of SHP-2 function and specificity in Xenopus mesoderm induction. *Mol Cell Biol* 18(1):161-177.

Oka T, Ouchida M, Koyama M, Ogama Y, Takada S, Nakatani Y, Tanaka T, Yoshino T, Hayashi K, Ohara N, Kondo E, Takahashi K, Tsuchiyama J, Tanimoto M, Shimizu K and Akagi T (2002) Gene silencing of the tyrosine phosphatase SHP1 gene by aberrant methylation in leukemias/lymphomas. *Cancer Res* 62(22):6390-6394.

Ren Y, Meng S, Mei L, Zhao Z J, Jove R and Wu J (2004) Roles of Gab1 and SHP2 in paxillin tyrosine dephosphorylation and Src activation in response to epidermal growth factor. *J Biol Chem* 279(9):8497-8505.

Schubbert S, Lieuw K, Rowe S L, Lee C M, Li X, Loh M L, Clapp D W and Shannon K M (2005) Functional analysis of leukemia-associated PTPN11 mutations in primary hematopoietic cells. *Blood* 106(1):311-317.

Shen K, Keng Y F, Wu L, Guo XL, Lawrence D S and Zhang Z Y (2001) Acquisition of a specific and potent PTP1B inhibitor from a novel combinatorial library and screening procedure. *J Biol Chem* 276(50):47311-47319.

Stein C A (1993) Suramin: a novel antineoplastic agent with multiple potential mechanisms of action. *Cancer Res* 53(10 Suppl):2239-2248.

Tartaglia M and Gelb B D (2005) Germ-line and somatic PTPN11 mutations in human disease. *Eur J Med Genet* 48(2):81-96.

Tartaglia M, Niemeyer C M, Fragale A, Song X, Buechner J, Jung A, Hahlen K, Hasle H, Licht J D and Gelb B D (2003) Somatic mutations in PTPN11 in juvenile myelomonocytic leukemia, myelodysplastic syndromes and acute myeloid leukemia. *Nat Genet* 34(2):148-150.

Yamauchi K, Milarski K L, Saltiel A R and Pessin J E (1995) Protein-tyrosine-phosphatase SHPTP2 is a required positive effector for insulin downstream signaling. *Proc Natl Acad Sci U S A* 92(3):664-668.

Yang J, Liang X, Niu T, Meng W, Zhao Z and Zhou G W (1998) Crystal structure of the catalytic domain of protein-tyrosine phosphatase SHP-1. *J Biol Chem* 273(43):28199-28207.

Yang J, Liu L, He D, Song X, Liang X, Zhao Z J and Zhou G W (2003) Crystal structure of human protein-tyrosine phosphatase SHP-1. *J Biol Chem* 278(8):6516-6520.

Zhang Z Y (2002) Protein tyrosine phosphatases: structure and function, substrate specificity, and inhibitor development. *Annu Rev Pharmacol Toxicol* 42:209-234.

TABLE II

| Name<br>MW<br>Structure | % PTP activity (a)[1] | IC$_{50}$ (μM) (N)[2] | MS (API-ES) m/z<br>HRMS<br>(API-ES) m/z | Comments |
|---|---|---|---|---|
| RPM187<br>384.41 (2.05) | 66 ± 4%<br>(3)<br>at 20 uM | >100<br>(5) | | |

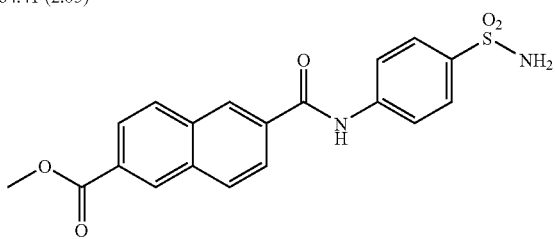

TABLE II-continued

| Name MW Structure | % PTP activity (a)[1] | IC$_{50}$ (μM) (N)[2] | MS (API-ES) m/z HRMS (API-ES) m/z | Comments |
|---|---|---|---|---|
| RPM195 370.98 (2.02) | 54 ± 6% (3) at 20 uM | >100 (5) | | |
| RPM202 365.35 (1.96) | 58 ± 7% (3) at 20 uM | 33-100 (5) | | |
| RPM204 351.31 (2.15) | 68 ± 5% (3) at 20 uM | 33-100 (4) | | |
| RPM185 349.14 (2.05) | 71 ± 3% (3) at 20 uM | >100 (5) | | |
| RPM194 335.14 (2.08) | 69 ± 7.5% (3) at 20 uM | >100 (5) | | |

TABLE II-continued

| Name MW Structure | % PTP activity (a)[1] | IC$_{50}$ (μM) (N)[2] | MS (API-ES) m/z HRMS (API-ES) m/z | Comments |
|---|---|---|---|---|
| HL2-022-1-Intermediate 377.39 (2.00) | 68 ± 20% (7) | >100 (5) | | |
| HL2-022-1 335.31 (2.00) | 53 ± 4% (6) | >100 (5) | | |
| HL2-022-2 371.36 (2.00) | 52 ± 17% (5) | >100 (5) | | |
| HL2-026-Intermediate 421.40 (2.00) | 40 ± 4% (6) | 33-100 (5) | | |
| HL2-026 379.32 (2.00) | 87 ± 14% (6) | >100 (5) | | |

TABLE II-continued
| Name MW Structure | % PTP activity (a)[1] | IC$_{50}$ (μM) (N)[2] | MS (API-ES) m/z HRMS (API-ES) m/z | Comments |
|---|---|---|---|---|
| RPM183 291.3 (2.00) 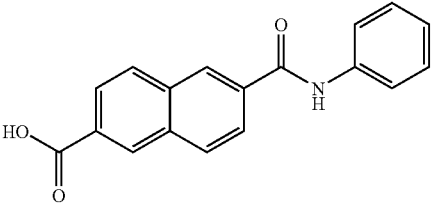 [SMILES: O=C(O)c1ccc2cc(C(=O)Nc3ccccc3)ccc2c1] | 79 ± 16 (7) | >100 (5) | | |
| RPM188 360.05 (2.04) 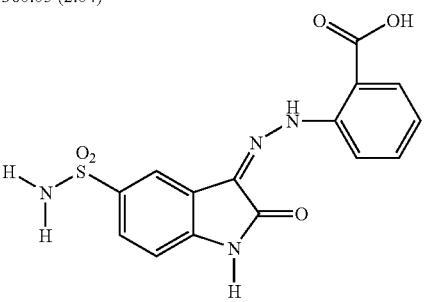 | 65 ± 3% (3) at 20 μM | >100 (5) | 359 359.0452 | |
| RPM216 331.35 (2.03) 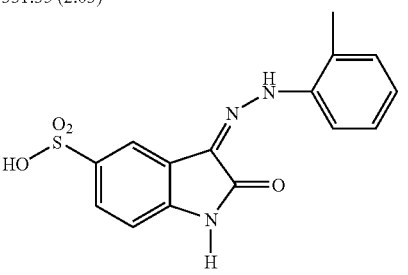 | 50 ± 14% (3) at 20 μM | >100 (5) | 330 330.0626 | |
| RPM219 345.17 (2.01) 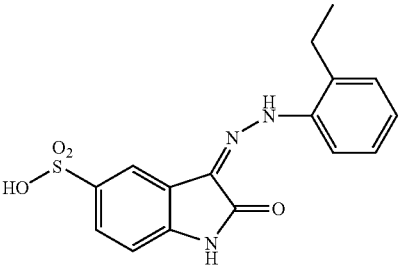 [SMILES: CCc1ccccc1N/N=C1\C(=O)Nc2ccc(S(=O)(=O)O)cc21] | 89 ± 2% (3) at 20 μM | 33-100 (4) | 344 344.0717 | |
| RPM220 335.31 (1.97) 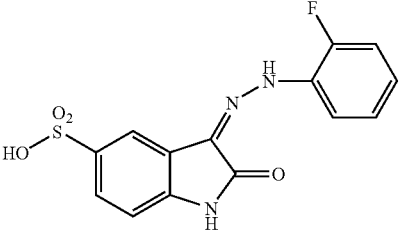 [SMILES: O=C1Nc2ccc(S(=O)(=O)O)cc2/C1=N/Nc1ccccc1F] | 73 ± 10% (3) at 20 μM | >100 (4) | 333.9 334.0310 | |

TABLE II-continued

| Name MW Structure | % PTP activity (a)[1] | IC$_{50}$ (μM) (N)[2] | MS (API-ES) m/z HRMS (API-ES) m/z | Comments |
|---|---|---|---|---|
| RPM221 385.32 (2.02) | 63 ± 4% (3) at 20 μM | 33-100 (3) | 384 384.0279 | |
| RPM215 317.32 (1.99) | 51 ± 3% (3) at 20 μM | >100 (3) | 316 316.0399 | |
| RPM222 407.27 (2.06) | 58 ± 6% (3) at 20 μM | 33-100 (3) | 405.9 405.9935 | |
| RPM186 402.1 (2.10) | 0.8 ± 1% (3) at 20 μM | 7.94 ± 4.56 (9) | 403 403.1066 | IC$_{50}$ for Shp1 10.75 ± 7.81 (6) |

TABLE II-continued
| Name MW Structure | | % PTP activity (a)[1] | IC$_{50}$ (μM) (N)[2] | MS (API-ES) m/z HRMS (API-ES) m/z | Comments |
|---|---|---|---|---|---|
| RPM218 386.21 (2.02) | 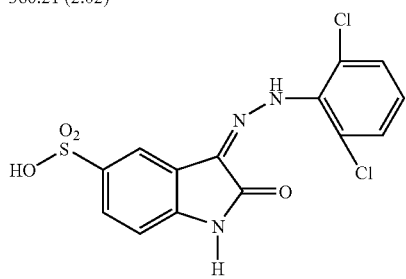 | 53 ± 0.1% (2) at 20 μM | 33-100 (3) | 383.9 385.9 383.9619 | |
| RPM224 386.21 (2.05) | 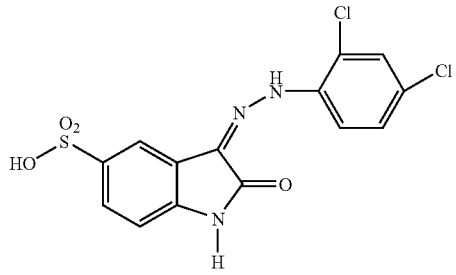 [SMILES: O=C1Nc2ccc(S(=O)(=O)O)cc2/C1=N/Nc1ccc(Cl)cc1Cl] | 81 ± 10% (3) at 20 μM | 33-100 (4) | 383.9 385.9 383.9619 | |
| RPM225 386.21 (2.08) | 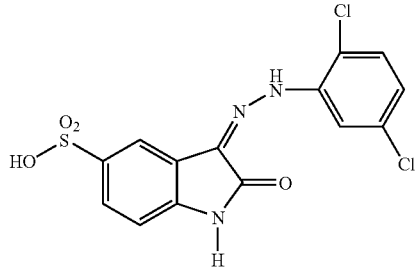 [SMILES: O=C1Nc2ccc(S(=O)(=O)O)cc2/C1=N/Nc1cc(Cl)ccc1Cl] | 73 ± 22% at 20 μM | 33-100 (4) | 383.9 385.9 383.9618 | |
| RPM223 367.38 (2.02) | 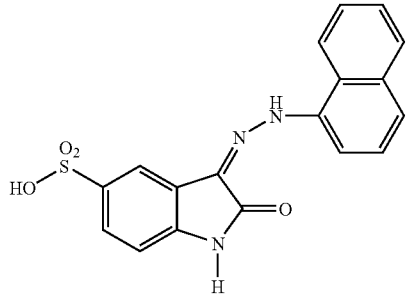 [SMILES: O=C1Nc2ccc(S(=O)(=O)O)cc2/C1=N/Nc1cccc2ccccc12] | 76 + 12% at 20 μM | 33-100 (4) | 366 366.0555 | |

TABLE II-continued

| Name MW Structure | % PTP activity (a)[1] | IC$_{50}$ (μM) (N)[2] | MS (API-ES) m/z HRMS (API-ES) m/z | Comments |
|---|---|---|---|---|
| RPM211 361.33 (1.97) | 67 ± 8% at 20 μM | 33-100 (4) | 360 360.0297 | |
| RPM191 484.91 (1.96) | 65.069630% 53.990500% at 20 μM | 33-100 (5) | 483. 486 483.0517 | |
| RPM134 361.325 (2.05) | 13 ± 5% (12) | 4.99 ± 2.31 (12) | 362 379 379.0818 | IC$_{50}$ for Shp1 93.50 ± 17.41 (5) |
| RPM124 389.379 (2.03) | 52 ± 5% (6) | 33-100 (4) | 390 390.087 407.1139 | |

TABLE II-continued

| Name MW Structure | % PTP activity (a)[1] | IC$_{50}$ (μM) (N)[2] | MS (API-ES) m/z HRMS (API-ES) m/z | Comments |
|---|---|---|---|---|
| RPM154 403.406 (2.03) | 73 ± 3% (6) | >100 (4) | 404 404.1018 | |
| RPM176 417.433 (1.99) | 50% ± 5% (6) | >100 (4) | 418 435.1448 418.1180 | |
| RPM156 479.503 (2.02) | 34 ± 4% (12) | >100 (4) | 480 480.1289 | |
| RPM177 431.416 (2.06) | 36 ± 8% (6) | >100 (4) | 432 449 449.1240 432.0974 | |

TABLE II-continued
| Name MW Structure | % PTP activity (a)[1] | IC$_{50}$ (μM) (N)[2] | MS (API-ES) m/z HRMS (API-ES) m/z | Comments |
|---|---|---|---|---|
| RPM146 432.447 (2.00) 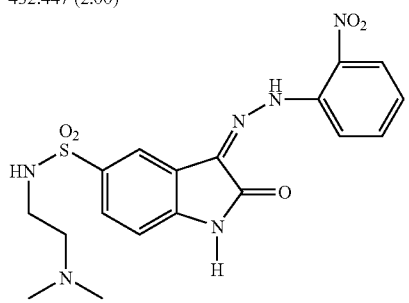 | 57 ± 6% (6) | >100 (4) | 433 433.1293 | |
| RPM170 403.406 (2.02) 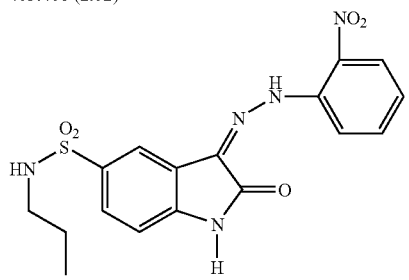 | 43 ± 8% (12) | >100 (4) | 421 404 421.1287 404.1014 | |
| RPM169 403.406 (2.01) 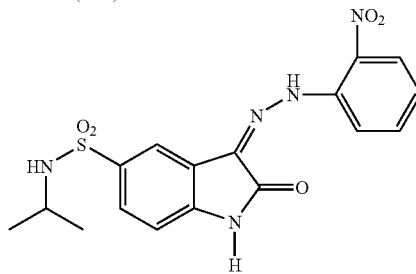 | 8 ± 3% (12) | 49.6 ± 25.5 (6) | 421 404 421.1285 404.1016 | IC$_{50}$ for Shp1 110.01 ± 40.85 (5) |
| RPM171 419.405 (2.03) 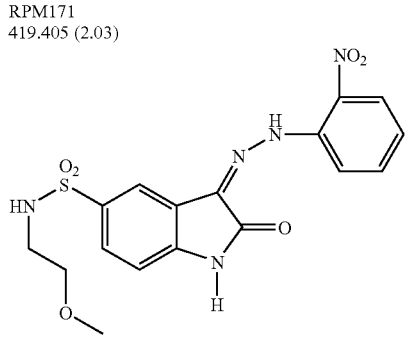 | 44 ± 8% (12) | >100 (4) | 420 437 437.1243 420.0979 | |

TABLE II-continued

| Name MW Structure | % PTP activity (a)[1] | IC$_{50}$ (μM) (N)[2] | MS (API-ES) m/z HRMS (API-ES) m/z | Comments |
|---|---|---|---|---|
| RPM173 417.433 (2.04) | 33 ± 7% (12) | >100 (4) | 418 435 435.1448 418.1181 | |
| RPM172 445.443 (2.02) | 35 ± 5% (12) | >100 (4) | 446 463.1398 446.1138. | |
| RPM168 441.411 (2.02) | 42 + 4% (6) | >100 (4) | 459 459.1082 | |
| RPM140 457.472 (2.04) | 37 ± 4% (6) | >100 (4) | 475 480 475.0852 | |

TABLE II-continued

| Name MW Structure | % PTP activity (a)[1] | IC$_{50}$ (μM) (N)[2] | MS (API-ES) m/z HRMS (API-ES) m/z | Comments |
|---|---|---|---|---|
| RPM137 481.446 (2.03) | 31 ± 4% (12) | >100 (4) | 481.2 499 504 499.1392 | |
| RPM138 481.446 (2.04) | 36 ± 4% (6) | >100 (4) | 499 504 499.1387 | |
| RPM136 465.447 (2.03) | 39 ± 8% (12) | >100 (4) | 466 488 466.1180 | |
| RPM145 452.437 (2.03) | 37 + 11% (12) | >100 (4) | 453 453.0978 | |

TABLE II-continued

| Name MW Structure | % PTP activity (a)[1] | IC$_{50}$ (μM) (N)[2] | MS (API-ES) m/z HRMS (API-ES) m/z | Comments |
|---|---|---|---|---|
| RPM135 452.437 (2.02) | 47 ± 10% (12) | 33-100 (4) | 453 475 453.0980 | |
| RPM139 485.90 (2.04) | 12 ± 5% (12) | 10.12 ± 6.78 (5) | 486 504 508 503.0894 486.062 | IC$_{50}$ for Shp1 42.16 ± 15.16 (4) |
| HL2-016-1 378.83 (2.00) | 36 ± 11% (12) | >100 (4) | 378.9 379.0627 | |
| HL2-016.2 350.78 (2.00) | 40 ± 8% (12) | >100 (4) | 351.0 [M + NH4], 368.0576 | |

TABLE II-continued

| Name<br>MW<br>Structure | % PTP<br>activity (a)[1] | IC$_{50}$ (μM) (N)[2] | MS (API-ES) m/z<br>HRMS<br>(API-ES)<br>m/z | Comments |
|---|---|---|---|---|
| HL2-016-3<br>470.93 (2.00) | 84 ± 24%<br>(6) | >100<br>(4) | 469.09<br>471.0873 | |
| HL2-016-4<br>475.35 (2.00) | 32 ± 17%<br>(12) | >100<br>(4) | 474.9<br>475.0378 | |
| HL2-016-5<br>470.93 (2.00) | 51 ± 4%<br>(6) | >100<br>(4) | 471.0<br>471.0882 | |
| HL2-016-6<br>446.93 (2.00) | 51 ± 3%<br>(6) | >100<br>(4) | 446.9<br>447.0346 | |

TABLE II-continued
| Name MW Structure | % PTP activity (a)[1] | IC$_{50}$ (μM) (N)[2] | MS (API-ES) m/z HRMS (API-ES) m/z | Comments |
|---|---|---|---|---|
| HL2-016-7 441.89 (2.00) 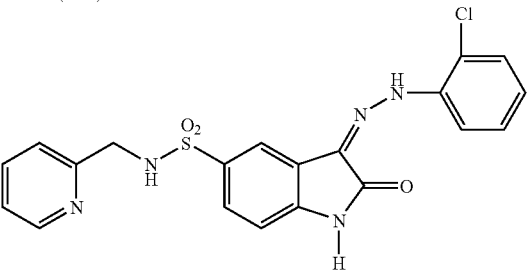 | 41 ± 23% (12) | >100 (4) | 442.0 442.0740 | |
| HL2-016-8 449.91 (2.00) 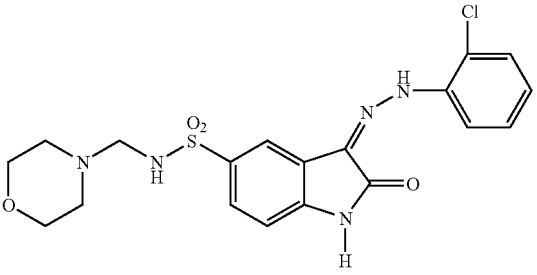 [SMILES: O=C1Nc2ccc(S(=O)(=O)NCN3CCOCC3)cc2/C1=N/Nc1ccccc1Cl] | 41 ± 4% (6) | >100 (4) | | $^1$H NMR |
| HL2-016-9 392.86 (2.00) 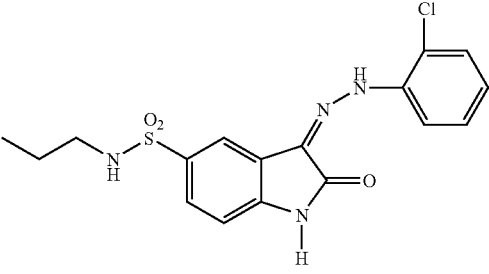 [SMILES: CCCNS(=O)(=O)c1ccc2c(c1)/C(=N/Nc1ccccc1Cl)C(=O)N2] | 48 ± 1% (6) | >100 (4) | 393.0 393.0788 | |
| HL2-016-10 406.89 (2.00) 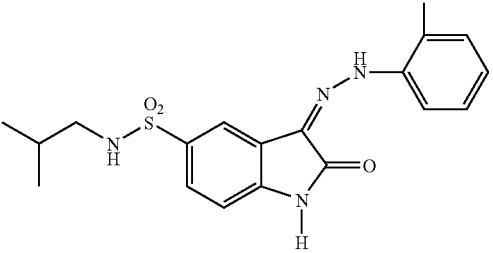 | 36 ± 17 (12) | >100 (4) | | $^1$H NMR |

TABLE II-continued

| Name MW Structure | % PTP activity (a)[1] | IC$_{50}$ (μM) (N)[2] | MS (API-ES) m/z HRMS (API-ES) m/z | Comments |
|---|---|---|---|---|
| HL2-016-11 430.86 (2.00) | 55 ± 7% (6) | >100 (4) | 431.05 431.0563 | |
| HL2-016-12 408.86 (2.00) | 32 ± 3% (6) | >100 (4) | 409.0 409.0738 | |
| HL2-016-13 406.89 (2.00) | 35 ± 4% (6) | >100 (4) | 407.0 407.0946 | |
| HL2-016-14 434.90 (2.00) | 42 ± 5% (6) | >100 (4) | 435.1 435.0901 | |

TABLE II-continued
| Name<br>MW<br>Structure | % PTP<br>activity (a)[1] | $IC_{50}$ (μM) (N)[2] | MS (API-ES) m/z<br>HRMS (API-ES)<br>m/z | Comments |
|---|---|---|---|---|
| HL2-016-15<br>441.89 (2.00)<br>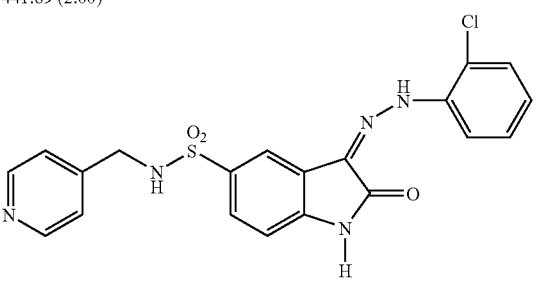 | 48 ± 5%<br>(6) | >100<br>(4) | 442.0<br>442.0753 | |
| HL2-016-16<br>454.93 (2.00)<br>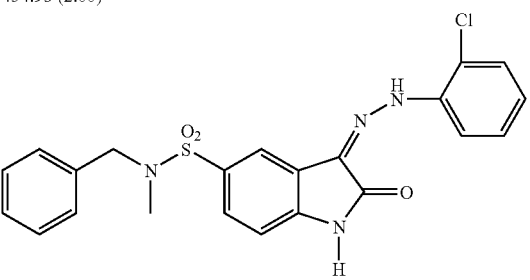 | 64 ± 12%<br>(6) | >100<br>(4) | 455.1<br>455.0954 | |
| HL2-016-18<br>441.89 (2.00)<br>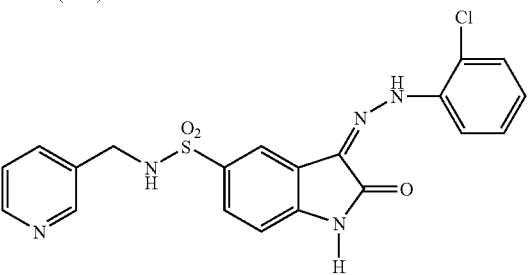 | 78 ± 10%<br>(6) | >100<br>(4) | 442.0<br>442.0736 | |
| HL2-016-19<br>421.90 (2.00)<br>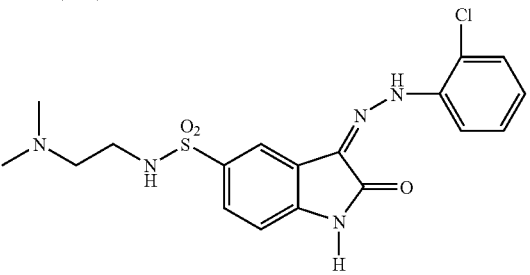 [SMILES: CN(C)CCNS(=O)(=O)c1ccc2c(c1)/C(=N/Nc1ccccc1Cl)C(=O)N2] | 89 ± 3%<br>(6) | Activation | 442.0<br>422.1070 | |

TABLE II-continued
| Name MW Structure | % PTP activity (a)[1] | IC$_{50}$ (μM) (N)[2] | MS (API-ES) m/z HRMS (API-ES) m/z | Comments |
|---|---|---|---|---|
| HL2-016-20 452.44 (2.00) 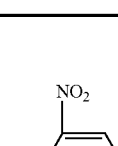 | 68 ± 8% (6) | >100 (4) | 453.0 453.0983 | |
| HL2-016-21 446.48 (2.00) 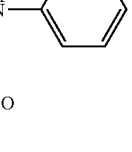 | 77 ± 2% (6) | Activation | 447.1 447.1454 | |
| HL2-016-22 435.93 (2.00)  | 80 ± 0.7% (6) | Activation | 436.1 436.1221 | |
| HL1-047 282 (2.00) 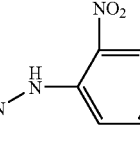 | 93 ± 9% (3) | 33-100 (4) | 283.1 283.0827 | |

TABLE II-continued

| Name MW Structure | % PTP activity (a)[1] | IC$_{50}$ (μM) (N)[2] | MS (API-ES) m/z HRMS (API-ES) m/z | Comments |
|---|---|---|---|---|
| HL1-050-1 271 (2.00) | 99 ± 2% (3) | 33-100 (3) | 272.0 272.0581 | |
| HL1-050-2 282 (2.00) | 32 ± 3% (3) | >100 (4) | 283.09 383.0827 | |
| HL1-056 (NSC-117199) 362 (2.00) | 86 ± 3% (6) | 47.26 ± 10.23 (8) | 361.04 363.0397 | IC$_{50}$ for Shp1 68.10 ± 17.11 (4) |
| HL1-058-1 351 (2.00) | 69 ± 9% (2) | 33-100 (4) | 352.0 352.0158 | |

TABLE II-continued

| Name MW Structure | % PTP activity (a)[1] | IC$_{50}$ (μM) (N)[2] | MS (API-ES) m/z HRMS (API-ES) m/z | Comments |
|---|---|---|---|---|
| HL1-058-2<br>362 (2.00) | 73 ± 7%<br>(3) | 33-100<br>(4) | 361.04<br>361.0432 | |
| HL1-058-3<br>374 (2.00) | 46 ± 4%<br>(3) | 33-100<br>(4) | 375.0<br>375.0121 | |
| Bromopyrogallol<br>558 | | 1.085 ± 0.40<br>(2) | | Commercially available |
| PyrogallolRed<br>400 | | 2.44 ± 1.37<br>(2) | | Commercially available |

TABLE II-continued
| Name<br>MW<br>Structure | % PTP activity (a)[1] | IC$_{50}$ (μM) (N)[2] | MS (API-ES) m/z<br>HRMS (API-ES) m/z | Comments |
|---|---|---|---|---|
| Hematin<br>300 | | 6.50 ± 0.48<br>(2) | | Commercially available |
| 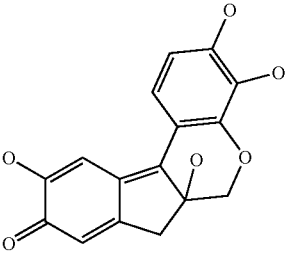 | | | | |
| NSC-87877<br>459.45 | | 0.318 ± 0.049<br>(11) | | Commercially available<br>IC$_{50}$ for Shp1<br>0.355 ± 0.073 |
| 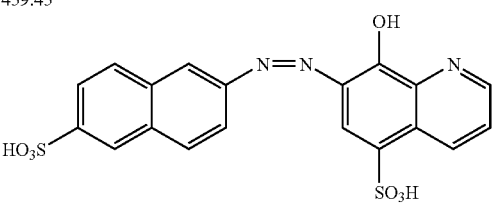 | | | | |
| NSC-119910<br>372.36 | 0.56 ± 0.1%<br>(3) | | | |
| 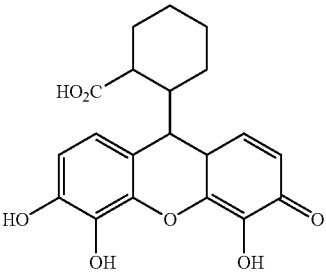 [SMILES: O=C1C=CC2C(=C1O)Oc1c(ccc(O)c1O)C2C1CCCCC1C(=O)O] | | | | |
| HL2-052-2<br>325.27, 1.38 mg | 46 ± 3%<br>(2)<br>at 20 μM | 3.55 ± 1.94<br>(11) | 324.07<br>326.0767 | IC$_{50}$ for Shp1<br>21.41 ± 9.58<br>(4) |
| 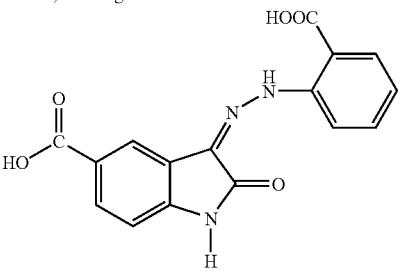 | | | | |
| HL2-052-3<br>325.27, 1.08 mg | 56.94%<br>(1)<br>at 20 μM | 16.07 ± 6.90<br>(10) | 326.0<br>326.0776 | IC$_{50}$ for Shp1<br>72.52 ± 19.26<br>(4) |
| 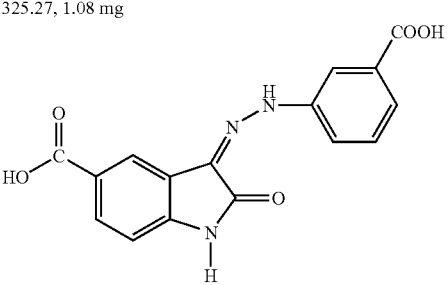 | | | | |

TABLE II-continued

| Name MW Structure | % PTP activity (a)[1] | IC$_{50}$ (μM) (N)[2] | MS (API-ES) m/z HRMS (API-ES) m/z | Comments |
|---|---|---|---|---|
| HL2-054 326.26, 1.26 mg | 60.57% (1) at 20 μM | >100 (5) | 327.0 327.0727 | |
| HL2-070-1 380.14, 1.21 mg | 100.18% (1) at 20 μM | >100 (5) | 381.1 381.1563 | |
| HL2-070-2 380.14, 1.34 mg | 57.16% (1) at 20 μM | >100 (5) | 381.1 381.1562 | |
| HL2-070-3 381.14, 1.59 mg | 14 ± 2% (2) at 20 μM | >100 (5) | 382.1 382.1521 | |

TABLE II-continued

| Name<br>MW<br>Structure | % PTP activity (a)[1] | IC$_{50}$ (μM) (N)[2] | MS (API-ES) m/z<br>HRMS (API-ES) m/z | Comments |
|---|---|---|---|---|
| HL2-070-4<br>448.85, 1.17 mg | 30 ± 4%<br>(2)<br>at 20 μM | >100<br>(5) | 449.1<br>449.1015 | |
| HL2-070-5<br>448.85, 1.08 mg | 62.32%<br>(1)<br>at 20 μM | 21.67 ± 5.19<br>(6) | 449.1<br>449.1013 | IC$_{50}$ for Shp1<br>19.45 ± 1.79<br>(4) |
| HL2-070-6<br>366.13, 1.41 mg | 78.87%<br>(1)<br>at 20 μM | >100<br>(5) | 367.1<br>367.1397 | |
| HL2-070-7<br>366.13, 1.52 mg | 53.62%<br>(1)<br>at 20 μM | >100<br>(5) | 367.1<br>367.1396 | |

TABLE II-continued

| Name<br>MW<br>Structure | % PTP<br>activity (a)[1] | IC$_{50}$ (μM) (N)[2] | MS (API-ES) m/z<br>HRMS<br>(API-ES)<br>m/z | Comments |
|---|---|---|---|---|
| HL2-070-9<br>449.85, 1.16 mg | 25 ± 2%<br>(2)<br>at 20 μM | >100<br>(5) | 450.1<br>450.0971<br>448.0962 | |
| RPM275<br>358.11, 1.22 mg | 58.53%<br>(1)<br>at 20 μM | >100<br>(5) | 359<br>359.1169 | |
| RPM283<br>401.12, 1.22 mg | 52 ± 7%<br>(2)<br>At 20 μM | >100<br>(5) | 402<br>385<br>402.1227 | |
| RPM284<br>472.19, 1.34 mg | 47 ± 6%<br>(2)<br>At 20 μM | >100<br>(5) | 473.1<br>473.1975 | |

TABLE II-continued

| Name MW Structure | % PTP activity (a)[1] | IC$_{50}$ (μM) (N)[2] | MS (API-ES) m/z HRMS (API-ES) m/z | Comments |
|---|---|---|---|---|
| RPM285 459.16, 1.37 mg | 51 ± 7% (2) At 20 μM | >100 (5) | 460 460.1652 | |
| RPM287 491.19, 1.06 mg | 48 ± 10% (2) At 20 μM | >100 (5) | 492 492.1698 | |
| RPM288 429.14, 1.12 mg | 30 ± 2% (2) at 20 μM | >100 (5) | 430 430.1432 | |

TABLE II-continued

| Name MW Structure | % PTP activity (a)[1] | IC$_{50}$ (μM) (N)[2] | MS (API-ES) m/z HRMS (API-ES) m/z | Comments |
|---|---|---|---|---|
| RPM290 492.16, 1.11 mg | 46 ± 2% (2) At 20 μM | 33-100 (5) | 493 493.1649 | |
| RPM292 481.14, 1.05 mg | 47 ± 7% (20 At 20 μM | 33-100 (4) | 482 482.1489 | |
| RPM293 514.20, 1.17 mg | 49 ± 6% (2) At 20 μM | >100 (5) | 515 515.2070. | |

TABLE II-continued

| Name MW Structure | % PTP activity (a)[1] | IC$_{50}$ (μM) (N)[2] | MS (API-ES) m/z HRMS (API-ES) m/z | Comments |
|---|---|---|---|---|
| RPM294 429.15, 1.02 mg | 48 ± 0% (2) At 20 μM | >100 (5) | 430 430.1540. | |
| RPM295 415.13, 1.11 mg | 43 ± 2% (2) At 20 μM | >100 (5) | 416 416.1385 | |
| RPM296 429.15, 1.20 mg | 48 ± 2% (2) At 20 μM | >100 (5) | 430 430.1538. | |
| RPM297 402.10, 1.18 mg | 54 ± 8% (2) At 20 μM | 7.58 ± 3.68 (9) | 403 403.1095 | IC50 for Shp1 15.66 ± 1.66 (4) |

TABLE II-continued

| Name MW Structure | % PTP activity (a)[1] | IC$_{50}$ (μM) (N)[2] | MS (API-ES) m/z HRMS (API-ES) m/z | Comments |
|---|---|---|---|---|
| RPM302 429.14, 1.09 mg | 51 ± 7% (2) at 20 μM | 33-100 (3) | 430 430.1435 | |
| RPM303 402.10, 1.29 mg | 46 ± 1% (2) 20 μM | >100 (4) | 403 430.1070 | |
| RPM304 401.10, 1.27 mg | 82.31% (1) At 20 μM | 33-100 (4) | 402 402.1114 | |
| RPM305 401.10, 1.14 mg | 56.77% (1) at 20 μM | 33-100 (4) | 402 402.1119 | |

TABLE II-continued
| Name MW Structure | % PTP activity (a)[1] | IC$_{50}$ (μM) (N)[2] | MS (API-ES) m/z HRMS (API-ES) m/z | Comments |
|---|---|---|---|---|
| RPM307 336.03, 1.11 mg 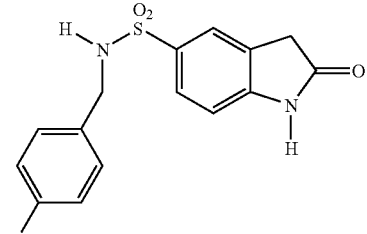 | 39 ± 10% (20) at 20 μM | >100 (4) | 337 354 | $^1$H NMR |
| RPM310 484.06, 1.04 mg 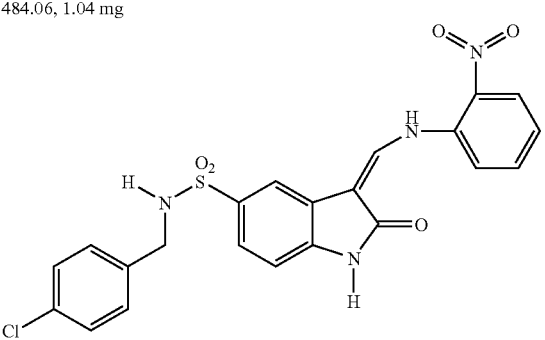 | 66.20% (1) At 20 μM | >100 (4) | 485 485.0677 | |
| RPM325 401.12, 1.11 mg 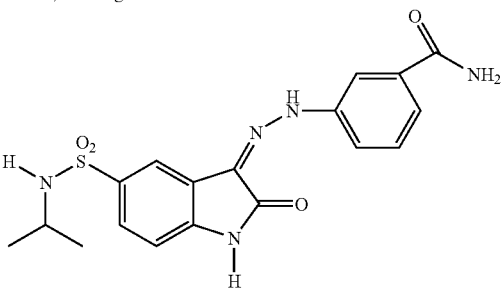 | 40 + 4% (2) at 20 μM | 33-100 (4) | 402 419 424 402.1234 419.1496 424.1050 | |
| RPM326 472.19, 1.26 mg 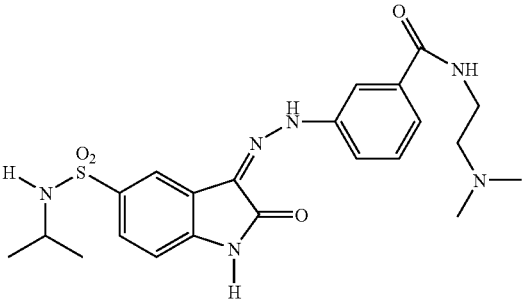 [SMILES: CC(C)NS(=O)(=O)c1ccc2c(c1)/C(=N/Nc1cccc(C(=O)NCCN(C)C)c1)C(=O)N2] | 57 + 13% (2) at 20 μM | Activation | 473 473.1976 | |

TABLE II-continued

| Name MW Structure | % PTP activity (a)[1] | IC$_{50}$ (μM) (N)[2] | MS (API-ES) m/z HRMS (API-ES) m/z | Comments |
|---|---|---|---|---|
| RPM327 459.16, 1.21 mg | 44 + 7% (2) at 20 μM | 42.38 ± 21.02 (3) | 460 460.1649 | |
| RPM328 491.16, 1.17 mg | 47 ± 3% (2) at 20 μM | >100 (5) | 492 492.1691 | |
| RPM330 415.13, 1.17 mg | 47 ± 1% (2) at 20 μM | >100 (5) | 416 416.1389 | |
| RPM331 429.15, 1.05 mg | 45 + 2% 92) at 20 μM | >100 (5) | 430 430.154 | |

TABLE II-continued

| Name MW Structure | % PTP activity (a)[1] | IC$_{50}$ (μM) (N)[2] | MS (API-ES) m/z HRMS (API-ES) m/z | Comments |
|---|---|---|---|---|
| RPM332 492.16, 1.05 mg | 54 ± 7% (2) at 20 μM | 33-100 (5) | 493 493.1655 | |
| RPM333 481.14, 1.16 mg | 48 ± 9% (2) at 20 μM | 33-100 (5) | 482 482.1489 | |
| RPM334 514.20, 1.07 mg | 39 ± 5% (2) at 20 μM | >100 (5) | 515 515.2071 | |
| RPM335 415.12, 1.21 mg | 54.19% (1) At 20 μM | 33-100 (5) | 416 416.1276 | |

TABLE II-continued

| Name MW Structure | % PTP activity (a)[1] | IC$_{50}$ (μM) (N)[2] | MS (API-ES) m/z HRMS (API-ES) m/z | Comments |
|---|---|---|---|---|
| RPM336 401.10, 1.07 mg | 48 ± 7% (2) at 20 μM | 33-100 (5) | 402 402.1116 | |
| RPM347 400.12, 1.19 mg | 48 ± 9% (2) At 20 μM | >100 (5) | 401 401.1173 | |
| RPM270 315.71, 1.05 mg | 45 ± 18% (2) At 20 μM | 33-100 (4) | 313.9 316 314.0344 | |
| RPM320 309.32, 1.07 mg | 44 ± 5% (2) At 20 μM | >100 (4) | 308 308.1044 | |

TABLE II-continued

| Name MW Structure | % PTP activity (a)[1] | IC$_{50}$ (μM) (N)[2] | MS (API-ES) m/z HRMS (API-ES) m/z | Comments |
|---|---|---|---|---|
| RPM272 281.08, 1.20 mg | 43 ± 4% at 20 μM | >100 (5) | 282 282.0875 | |
| RPM351 315.32, 1.18 mg | 40 ± 11% (2) At 20 μM | >100 (5) | $^1$H NMR $^{13}$C NMR | |
| RPM350 329.35, 1.14 mg | 45 ± 7% (2) at 20 μM | >100 (5) | $^1$H NMR $^{13}$C NMR | |
| RPM352 265.26, 1.20 mg | 57 ± 9% (2) at 20 μM | >100 (5) | $^1$H NMR $^{13}$C NMR | |
| RPM341 279.29, 1.17 mg | 42 ± 10% (2) at 20 μM | >100 (5) | $^1$H NMR $^{13}$C NMR | |

TABLE II-continued

| Name MW Structure | % PTP activity (a)[1] | IC$_{50}$ (μM) (N)[2] | MS (API-ES) m/z HRMS (API-ES) m/z | Comments |
|---|---|---|---|---|
| RPM319 299.98, 1.01 mg 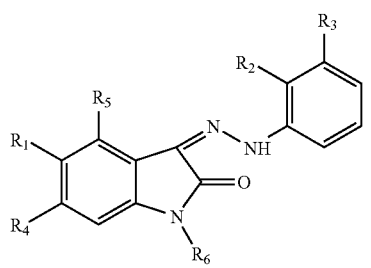 | 49 ± 4% (2) At 20 μM | >100 (5) | 298 298.0639 | |

The disclosure of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A compound having the formula (I):

(I)

[structure with substituents $R_1$, $R_2$, $R_3$, $R_4$, $R_5$, $R_6$]

wherein $R_1$ is $CO_2H$, $SO_2NHCH_2(C_6H_4)$—X, $SO_2NHCH_2(C_6H_5)$, $SO_2N(CH3)_2$, or $SO_2NHCH_2(C_6H_4)OCH_3$,
wherein X is one or more moieties selected from the group consisting of chlorine, oxymethyl, fluorine, methyl and morpholine;
wherein $R_4$ and $R_5$ are hydrogen;
wherein each of $R_2$ and $R_3$ are hydrogen, nitro, or $CO_2H$;
$R_6$ is hydrogen; and
wherein one of $R_2$ and $R_3$ is hydrogen and $R_2$ and $R_3$ are not concurrently the same functional group.

2. The compound according to claim 1 wherein $R_2$ or $R_3$ is nitro.

3. A compound having the formula (II):

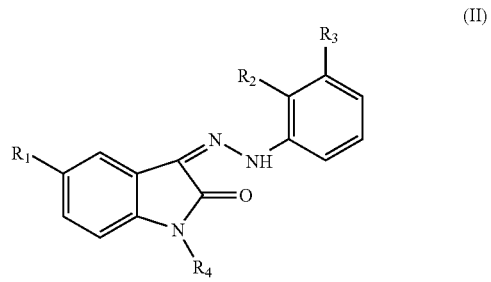

(II)

wherein $R_1$ is $CO_2H$, $SO_2NHCH_2(C_6H_5)$, or $SO_2NHCH_2C_6H_4Cl$;
wherein each of $R_2$ and $R_3$ are independently hydrogen, nitro, or $CO_2H$;
wherein $R_4$ is hydrogen, or benzyl; and
wherein one of $R_2$ and $R_3$ is hydrogen and $R_2$ and $R_3$ are not concurrently the same functional group.

4. The compound according to claim 3 wherein $R_1$ is $SO_2NHCH_2C_6H_4Cl$.

5. The compound according to claim 4 wherein $R_2$ is selected from the group consisting of nitro, and $CO_2H$.

6. The compound according to claim 3 wherein $R_4$ is hydrogen.

7. A compound having the formula (III):

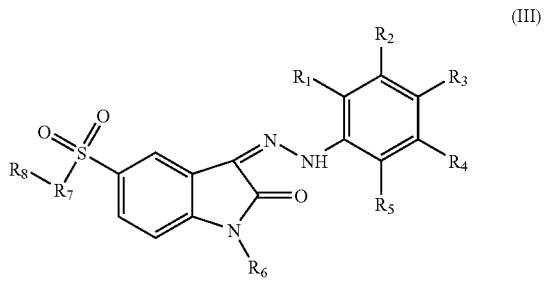

(III)

wherein each of $R_1$ through $R_5$ are independently hydrogen, nitro, or $CO_2H$;

$R_6$ is hydrogen; and $R_7$ is $NHCH_2(C_6H_4)$—X, wherein X is one or more moieties selected from the group consisting of hydrogen, fluorine, chlorine, and oxymethyl;

wherein at least one of $R_1$ through $R_5$ is not hydrogen.

8. The compound according to claim 7 wherein $R_3$ through $R_6$ are hydrogen and each of $R_1$ and $R_2$ is selected from the group consisting of nitro and $CO_2H$.

9. A compound having the formula (IV):

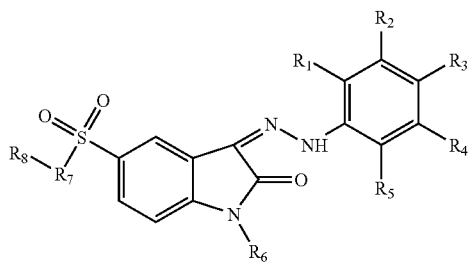

(IV)

wherein each of $R_1$ and $R_2$ are independently hydrogen, nitro, $CO_2H$, or $CO_2CH_3$;

$R_3$ through $R_5$ are hydrogen;

$R_6$ is hydrogen;

$R_7$ is $NHCH_2(C_6H_4)$—X, $SO_2NHCH_2(C_6H_5)$; or $SO_2NHCH_2(C_6H_4)OCH_3$;

wherein X is one or more moieties selected from the group consisting of chlorine, and oxymethyl; and wherein at least one of $R_1$ through $R_5$ is not hydrogen.

10. The compound according to claim 1 wherein $R_2$ is nitro when $R_1$ is $SO_2NHCH_2(C_6H_4)$—X, $SO_2NHCH_2(C_6H_5)$, $SO_2N(CH_3)_2$, or $SO_2NHCH_2(C_6H_4)OCH_3$.

11. The compound according to claim 3 wherein $R_2$ is nitro when $R_1$ is $SO_2NHCH_2(C_6H_5)$, or $SO_2NHCH_2C_6H_4Cl$.

* * * * *